United States Patent
Nishiuchi et al.

(10) Patent No.: US 10,537,128 B2
(45) Date of Patent: Jan. 21, 2020

(54) YEAST, YEAST EXTRACT CONTAINING GAMMA-GLU-ABU, AND A METHOD FOR PRODUCING THE SAME

(71) Applicant: AJINOMOTO CO., INC., Chuo-ku (JP)

(72) Inventors: Hiroaki Nishiuchi, Kawasaki (JP); Misato Morita, Kawasaki (JP); Wataru Hoshino, Kawasaki (JP); Junko Yamazaki, Kawasaki (JP); Takayuki Ito, Kawasaki (JP); Kazuo Yamagishi, Kawasaki (JP)

(73) Assignee: AJINOMOTO CO., INC., Chuo-ku (JP)

( * ) Notice: Subject to any disclaimer, the term of this patent is extended or adjusted under 35 U.S.C. 154(b) by 118 days.

(21) Appl. No.: 15/352,928

(22) Filed: Nov. 16, 2016

(65) Prior Publication Data

US 2017/0067085 A1 Mar. 9, 2017

Related U.S. Application Data

(60) Division of application No. 13/838,065, filed on Mar. 15, 2013, now abandoned, which is a continuation of
(Continued)

(30) Foreign Application Priority Data

Oct. 5, 2010 (JP) .................................. 2010-225479

(51) Int. Cl.
*C12P 13/14* (2006.01)
*A23L 31/15* (2016.01)
(Continued)

(52) U.S. Cl.
CPC ............... *A23L 31/15* (2016.08); *A23L 27/22* (2016.08); *A23L 27/24* (2016.08); *A23L 33/145* (2016.08);
(Continued)

(58) Field of Classification Search
None
See application file for complete search history.

(56) References Cited

U.S. PATENT DOCUMENTS 6,258,559 B1 * 7/2001 Zamost ................... C12N 1/16
435/69.1
6,902,749 B1 * 6/2005 Lortal ................ A23C 19/0325
426/37
(Continued)

FOREIGN PATENT DOCUMENTS

EP 2 251 413 11/2010
JP 54-157890 12/1979
(Continued)

OTHER PUBLICATIONS

International Search Report issued in PCT/JP2011/072875 dated Dec. 20, 2011.
(Continued)

*Primary Examiner* — Felicia C Turner
(74) *Attorney, Agent, or Firm* — Oblon, McClelland, Maier & Neustadt, L.L.P.

(57) ABSTRACT

A yeast extract containing 0.2% or more of γ-Glu-Abu based on dry weight of the yeast extract is produced by culturing a yeast, such as *Saccharomyces cervisiae* or *Candida utilis*, in a medium containing a compound selected from Abu (L-2-aminobutyric acid) and γ-Glu-Abu (L-γ-glutamyl-L-2-aminobutyric acid), and preparing a yeast extract from the obtained cells.

15 Claims, 4 Drawing Sheets

Specification includes a Sequence Listing.

Related U.S. Application Data application No. PCT/JP2011/072875, filed on Oct. 4, 2011.

(51) Int. Cl.
| | |
|---|---|
| *A23L 27/22* | (2016.01) |
| *A23L 27/24* | (2016.01) |
| *C12P 13/04* | (2006.01) |
| *A23L 33/145* | (2016.01) |
| *A23L 5/00* | (2016.01) |

(52) U.S. Cl.
CPC ............... *C12P 13/04* (2013.01); *C12P 13/14* (2013.01); *C12Y 203/02002* (2013.01); *C12Y 603/02002* (2013.01); *C12Y 603/02003* (2013.01); *A23L 5/00* (2016.08); *A23V 2002/00* (2013.01)

(56) References Cited

U.S. PATENT DOCUMENTS

| | | |
|---|---|---|
| 7,297,513 B2 | 11/2007 | Nishiuchi et al. |
| 7,553,638 B2 | 6/2009 | Nishiuchi et al. |
| 7,569,360 B2 | 8/2009 | Nishiuchi et al. |
| 2003/0124684 A1 | 7/2003 | Nishiuchi et al. |
| 2009/0130282 A1 | 5/2009 | Hofmann et al. |
| 2010/0120698 A1 | 5/2010 | Nagasaki et al. |
| 2010/0183792 A1 | 7/2010 | Nagasaki et al. |
| 2011/0097805 A1 | 4/2011 | Ohsu et al. |
| 2012/0034364 A1 | 2/2012 | Futaki et al. |
| 2013/0045305 A1 | 2/2013 | Nishiuchi et al. |

FOREIGN PATENT DOCUMENTS

| | | |
|---|---|---|
| JP | 60-75279 | 4/1985 |
| JP | 6-16702 | 3/1994 |
| JP | 8-332081 | 12/1996 |
| JP | 2004-298014 | 10/2004 |
| JP | 2008-99578 | 5/2008 |
| WO | 2007/042288 | 4/2007 |
| WO | 2007/055393 | 5/2007 |
| WO | 2008/139945 | 11/2008 |
| WO | 2008/139946 | 11/2008 |
| WO | 2009/110624 | 9/2009 |
| WO | WO 2010/114022 A1 | 10/2010 |
| WO | WO 2010-116833 A1 | 10/2010 |

OTHER PUBLICATIONS

Ohmori, S. et al., Biochim. Biophys. Acta., vol. 1472, No. 3, (1999) pp. 587-594.
Extended European Search Report dated May 22, 2014 in Patent Application No. 11830663.8.
International Preliminary Report on Patentability and Written Opinion dated May 8, 2013, in International Application No. PCT/JP2011/072875.
Yoichi Ueda, et al., "Characteristic Flavor Constituents in Water Extract of Garlic", Agric. Biol. Chem. 54 (1), 1990, pp. 163-169.
Yoichi Ueda, et al., "Flavor Characteristics of Glutathione in Raw and Cooked Foodstuffs", Biosci. Biotech. Biochem., 61(12), 1997, pp. 1977-1980.
Minghua Wang, et al., "Activation of Family C G-protein-coupled Receptors by the Tripeptide Glutathione", The Journal of Biological Chemistry, vol. 281, No. 13, Mar. 31, 2006, pp. 8864-8870.
Ana San Gabriel, et al., "The calcium-sensing receptor in taste tissue", Biochemical and Biophysical Research Communications 378, 2009, pp. 414-418.
Takeaki Ohsu, et al., "Involvement of the Calcium-sensing Receptor in Human Taste perception", The Journal of Biological Chemistry, vol. 285, No. 2, Jan. 8, 2010, pp. 1016-1022.
Naoyuki Taniguchi, Y-glutamyl cycle (III. Metabolism of Glutathione and Enzymes), Protein Nucleic acid Enzyme, vol. 33, No. 9, Special issue "Epoch of glutathione research", 1988, pp. 1432-1433 (with Partial English translation).
Ronald A. Vitali, et al., "The Isolation of $_\gamma$—$_L$—Glutamyl Peptides from a Fermentation Broth", The Journal of Biological Chemistry, vol. 240, No. 6, Jun. 6, 1965, pp. 2508-2511.
Reiko Nakayama, et al., "Synthesis of Y-Glutamylpeptides by Y-Glutamylcysteine Synthetase from Proteus mirabilis", Agric.Biol. Chem., 45 (12), 1981, pp. 2839-2845.
B. Volesky, et al., "Biosorption of heavy metals by Saccharomyces cerevisiae", Appl. Microbiol Biotechnol, 42, 1995, (Springer-Verlag 1995), pp. 797-806.
Kobayashi et al. (JP2891296) Sep. 16, 1997 AIPN Japanese Machine Translation pp. 1-8.
Toelstede et al. Kokumi Active Glutamyl Peptide in Cheese and Their Biogeneration by P. roquefortii 2009 Journal of Agricultual Food Chemistry vol. 57 pp. 3738-3748.

* cited by examiner

YEAST, YEAST EXTRACT CONTAINING GAMMA-GLU-ABU, AND A METHOD FOR PRODUCING THE SAME

CROSS-REFERENCE TO RELATED APPLICATIONS

This application is a divisional of U.S. patent application Ser. No. 13/838,065, filed Mar. 15, 2013, which is a continuation of International Patent Application No. PCT/JP2011/072875, filed Oct. 4, 2011, the disclosures of which are incorporated herein by reference in their entireties. This application claims priority to Japanese Patent Application No. 2010-225479, filed Oct. 5, 2010, the disclosure of which is incorporated herein by reference in its entirety.

TECHNICAL FIELD

The present invention relates to a yeast and yeast extract containing γ-Glu-Abu (L-γ-glutamyl-L-2-aminobutyric acid), as well as a method for producing the same. The yeast extract of the present invention is useful in the field of foodstuffs such as seasonings and health foods.

BACKGROUND ART

Yeast extracts have a function of imparting atsumi (thickness), umami, etc. to foodstuffs, and have been widely used as seasonings in the field of foodstuffs. Especially, glutathione (henceforth also referred to as "GSH"), which is a tripeptide consisting of glutamic acid, cysteine and glycine, is known to impart kokumi to foodstuffs (Non-patent documents 1 and 2), and seasonings containing GSH have been developed.

Meanwhile, although the calcium sensing receptor (CaSR), which is a G-protein classified into the class C, has been reported to respond to GSH (Non-patent document 3), the physiological significance thereof has not been clarified. Moreover, this CaSR is present also in the lingual cells, and it was considered to show a certain taste response (Non-patent document 4). Then, it has recently been clarified that this CaSR participates in recognition of kokumi in humans (Non-patent document 5). This reference reported that not only GSH that has been recognized as a kokumi substance, but also several γ-glutamyl compounds similarly respond to CaSR. Furthermore, it has been reported that peptides represented by the general formula γ-Glu-X or γ-Glu-X-Gly (X can represent an amino acid or amino acid derivative other than Cys), for example, γ-Glu-Met, γ-Glu-Thr, γ-Glu-Val-Gly, etc. have a kokumi-imparting effect (Patent document 1). Moreover, the group of esters including S- or O-carboxyalkylated γ-glutamyl or β-asparagyl peptides, and so forth are also reported as kokumi substances (Patent document 2). Although these peptides impart kokumi to foodstuffs like GSH, they do not have a reduced SH group unlike GSH. It is known that a substance having the reduced SH group such as GSH is generally unstable, and titer thereof is reduced with formation of disulfide bond (Patent document 2). However, γ-Glu-X, γ-Glu-X-Gly etc. are considered useful from the viewpoint that the kokumi-imparting peptides not having the reduced SH group are stable.

Tastes sensed after eating change with time, and the tastes are called initial taste, middle taste, and aftertaste in the order from the taste sensed immediately after eating. Although tastes imparted by various substances change with time in various patterns, concerning especially kokumi, a kokumi-imparting substance showing a taste-imparting pattern that imparts strong initial taste is highly desired. It is known that the γ-glutamyl compound, γ-Glu-Abu-Gly, has a kokumi-imparting action that mainly imparts initial-middle taste (Patent documents 3 and 4).

It is known that the synthesis and decomposition of glutathione, which is one of the γ-glutamyl compounds, is catalyzed by several enzymes which make up the γ-glutamyl cycle. In particular, γ-glutamyl transpeptidase is known to transfer the glutamate of GSH at the γ-position to another compound having an amino group, resulting in decomposition of GSH to cysteinylglycine (Non-patent document 6). It is considered that, if the compound having an amino group in this reaction is an amino acid, a dipeptide of γ-Glu-X can be generated as a by-product. However, research about producing these compounds effectively using microorganisms has not been positively performed to date, partially because they are by-products.

An analysis of the fermentation broth of *Micrococcus glutamicus* can be noted as findings about the dipeptide γ-Glu-X (Non-patent document 7). This reference reported that the fermentation broth was loaded onto various columns to separate peptides and the like, resulting in the isolation of γ-Glu-Glu, γ-Glu-Val, and γ-Glu-Leu. However, these were found as a result of separation with various columns, and the amounts of these peptides contained in the broth were not determined. In addition, there was not reported in all the above examples that γ-Glu-Abu was contained.

GSH is biosynthesized by two kinds of enzymes called γ-glutamylcysteine synthetase, which binds Glu and Cys to generate γ-Glu-Cys, and glutathione synthetase, which binds the generated γ-Glu-Cys and Gly to generate GSH. The substrate specificities of the enzymes were investigated in in vitro enzymatic reactions, and it was reported that γ-Glu-Abu was generated from Glu and Abu as the substrates (Non-patent document 8). However, this report concerns an example using a bacterium, *Proteus mirabilis*, and does not concern investigation using yeast. Furthermore, although Abu can be used as a substrate in an in vitro enzymatic reaction, any Abu synthetic pathway is not known for yeasts.

Yeast extracts produced from yeast cells as a raw material are seasonings that have been widely used in the field of foodstuffs, and are highly accepted by consumers. Therefore, a yeast extract is more preferred as a carrier of taste substances. Yeast strains containing minerals can be exemplified as the investigation concerning the use of yeast as a carrier of taste substances. It is known that if a metal is added to a medium, yeasts uptake the metal into the cells (Non-patent document 9). In particular, if trace elements such as zinc, iron, copper, manganese, selenium, molybdenum and chromium are added to the medium, yeasts can be used as a supply source of the desired enriched elements as foodstuffs (Patent document 5). From this point of view, methods for producing mineral-containing yeast have been developed (Patent documents 6 to 8).

Furthermore, yeast incorporating such minerals may also enjoy a merit concerning on taste. For example, there can be mentioned the yeast containing a large amount of magnesium (Patent document 9). This reference describes that although magnesium-enriched foodstuffs containing inorganic magnesium salt were also marketed, a strong bitterness and astringency was noted due to the mineral salt. As a result, it was quite more difficult to routinely eat the magnesium-enriched foodstuffs containing inorganic magnesium salt as compared to foodstuffs containing naturally occurring magnesium. In that context, Patent document 9 discloses a method to produce a foodstuff containing magnesium in natural form by letting yeast uptake magnesium.

As for nutritional merit of yeast that uptakes minerals, the technique disclosed in Patent document 10 can be exemplified. According to this reference, although zinc contributes to improvement of taste disorder and generative function, etc., zinc is still not taken in sufficient amounts. If zinc is added during the yeast cultivation process, yeast uptakes zinc into cells. In this case zinc is not accumulated in the cells as water-soluble form, but zinc is highly accumulated in the cells as amorphous zinc form which binds with a protein or an amino acid. When the amorphous zinc is taken into the human body, the amorphous zinc is more efficiently absorbed into the body compared with crystalline zinc. As a result, absorption of zinc into the body can be improved by taking zinc-containing yeast, as compared to simply taking zinc itself.

As described above, a method comprised by making yeast uptake a target substance and adding either the yeast or a yeast extract to foodstuffs can enjoy various advantages as compared to simply adding the target substance itself to foodstuffs. However, unlike minerals, which are essential nutrients, the ability of yeast to uptake an amino acid or a peptide is strictly controlled, and simply applying the technique for incorporating minerals into yeast to the techniques for uptake of amino acid or peptides was considered to be difficult.

As described above, although yeast cells or yeast extracts are preferred as a carrier of a γ-glutamyl compound such as γ-Glu-X as a kokumi-imparting agent, there have been substantially no reports about yeast cells containing such a γ-glutamyl compound, and a method for producing an extract prepared from the cells.

PRIOR ART REFERENCES

Patent Documents

Patent document 1: WO2007/055393
Patent document 2: WO2007/042288
Patent document 3: WO2008/139945
Patent document 4: WO2008/139946
Patent document 5: Japanese Patent Laid-open (Kokai) No. 2004-298014
Patent document 6: Japanese Patent Laid-open (Kokai) No. 54-157890
Patent document 7: Japanese Patent Laid-open (Kokai) No. 60-75279
Patent document 8: Japanese Patent Publication (Kokoku) No. 6-16702
Patent document 9: Japanese Patent Laid-open (Kokai) No. 8-332081
Patent document 10: Japanese Patent Laid-open (Kokai) No. 2008-099578

Non-Patent Documents

Non-patent document 1: Ueda et al., Agric. Biol. Chem., 54, 163-169 (1990)
Non-patent document 2: Ueda et al., Biosci. Biotechnolo. Biochem., 61, 1977-1980 (1997)
Non-patent document 3: Wang et al., Journal of Biological Chemistry, 281, 8864-8870 (2006)
Non-patent document 4: Gabriel et al., Biochemical and Biophysical Research Communications, 378, 414-418 (2009)
Non-patent document 5: Ohsu et al., Journal of Biological Chemistry, 285, 1016-1022 (2010)
Non-patent document 6: Protein Nucleic acid Enzyme, 1988-7, VOL. 33, NO. 9, ISSN 003909450, Special Issue "Epoch of glutathione research", pp. 1432-1433
Non-patent document 7: Ronald et al., Journal of Biological Chemistry, 240, p 2508-2511 (1965)
Non-patent document 8: Nakayama et al., Agric. Biol. Chem., 45(12), 2839-2845 (1981)
Non-patent document 9: B. Volesky, H. A., Appl. Microbiol. Biotechnol., 42; 797-806 (1995)

SUMMARY OF THE INVENTION

Object to be Achieved by the Invention

An object of the present invention is to provide a yeast extract having a kokumi-imparting effect of initial taste-imparting type, and a method for producing it.

Means for Achieving the Object

The inventors of the present invention previously found that γ-Glu-Abu (L-γ-glutamyl-L-2-aminobutyric acid) had high CaSR agonist activity and extremely excellent kokumi-imparting effect, and in particular, it had a taste-imparting pattern of initial taste-imparting type. Then, they found that yeasts took up Abu (α-aminobutyric acid) or γ-Glu-Abu into cells thereof, and by preparing a yeast extract from yeast cultured in a medium containing Abu or γ-Glu-Abu, a yeast extract containing γ-Glu-Abu could be produced. Moreover, they also found that if the aminotransferase activity or/and the α-ketobutyric acid synthetase activity were increased, intracellular Abu production advanced. Further, they also found that by allowing γ-glutamyltransferase to act on a yeast extract raw material to which Abu had been added, a yeast extract containing γ-Glu-Abu could be produced. The present invention was accomplished on the basis of these findings.

The present invention thus relates to the followings.

(1) A yeast extract containing 0.2% or more of γ-Glu-Abu based on dry weight of the yeast extract.

(2) A yeast extract containing 0.5% or more of γ-Glu-Abu based on dry weight of the yeast extract.

(3) A yeast extract containing 1.0% or more of γ-Glu-Abu based on dry weight of the yeast extract.

(4) The yeast extract as mentioned above, wherein the yeast belongs to the genus *Saccharomyces* or *Candida*.

(5) The yeast extract as mentioned above, which is obtained from *Saccharomyces cervisiae*.

(6) The yeast extract as mentioned above, which is obtained from *Candida utilis*.

(7) A method for producing a yeast extract containing γ-Glu-Abu, which comprises culturing a yeast in a medium to which a compound selected from Abu and γ-Glu-Abu is added, and preparing a yeast extract from the obtained cells.

(8) The method as mentioned above, wherein the compound is added to the medium in an amount of 10 ppm or more in the case of Abu, or 1 ppm or more in the case of γ-Glu-Abu, and the yeast extract contains 0.2% or more of γ-Glu-Abu based on dry weight of the yeast extract.

(9) The method as mentioned above, wherein the yeast belongs to the genus *Saccharomyces* or *Candida*.

(10) The method as mentioned above, wherein the yeast is *Saccharomyces cervisiae*.

(11) The method as mentioned above, wherein the yeast is *Candida utilis*.

(12) The method as mentioned above, wherein the yeast has one or both of the following characteristics:

(a) γ-glutamylcysteine synthetase activity is enhanced,
(b) glutathione synthetase activity is attenuated.

(13) A yeast having an increased γ-Glu-Abu content, which has been modified so that activity of aminotransferase or/and activity of α-ketobutyric acid synthetase are enhanced, and, activity of γ-glutamylcysteine synthetase is enhanced, or/and activity of glutathione synthetase is attenuated.

(14) The yeast as mentioned above, wherein the aminotransferase is an enzyme encoded by the BAT1 gene.

(15) The yeast as mentioned above, wherein the aminotransferase is an enzyme encoded by the UGA1 gene.

(16) The yeast as mentioned above, wherein the α-ketobutyric acid synthetase is an enzyme encoded by the CHA1 gene.

(17) The yeast as mentioned above, wherein a peptidase activity is further attenuated.

(18) A yeast extract produced from the yeast as mentioned above.

(19) A method for producing a yeast extract containing γ-Glu-Abu, which comprises allowing a γ-glutamyltransferase to act on a yeast extract raw material to which Abu has beeb added.

(20) The method as mentioned above, wherein Abu is added in an amount of 0.1% or more based on dry weight of the yeast extract raw material, and the yeast extract contains 0.2% or more of Abu based on dry weight of the yeast extract.

EMBODIMENTS FOR CARRYING OUT THE INVENTION

Figure 1:
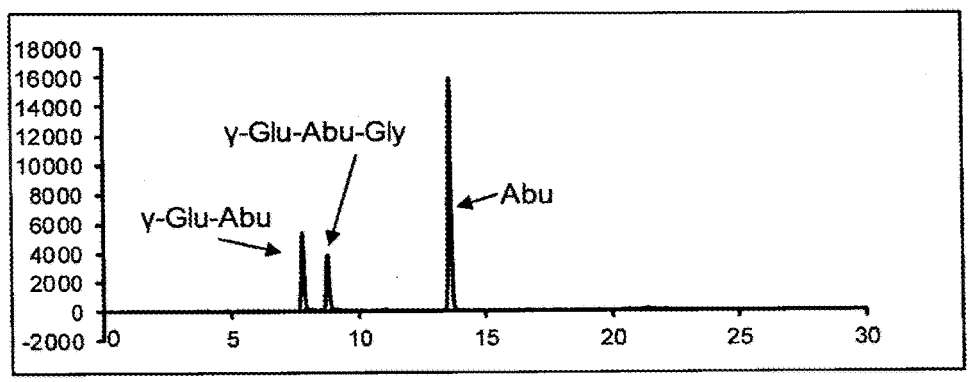
FIG. 1 shows mass chromatograms of Abu, γ-Glu-Abu, and γ-Glu-Abu-Gly samples.

Hereafter, the present invention will be explained in detail.

The yeast extract of the present invention is a yeast extract containing 0.2% or more of γ-Glu-Abu based on dry weight of the yeast extract.

The yeast extract of the present invention contains γ-Glu-Abu in an amount of 0.2% or more, preferably 0.5% or more, more preferably 1.0% or more, particularly preferably 2.0% or more, based on dry weight of the yeast extract.

The yeast used as the raw material of the yeast extract of the present invention is the same as the yeast used for the method of the present invention described later.

The form of the yeast extract of the present invention is not particularly limited, and it may be in the form of powder or solution. The yeast extract can have the same uses as that of conventional yeast extracts, for example, seasonings, food additives, health foods, and so forth. The yeast extract of the present invention is excellent in its kokumi-imparting effect. Since the kokumi-imparting effect is more strongly reinforced in the presence of umami or salty taste, an umami substance such as sodium L-glutamate and tasty nucleotides, and/or a salty substance such as sodium chloride may be added to the yeast extract. Further, since the yeast extract of the present invention has especially a superior effect of imparting kokumi as the initial taste, it may be mixed with a kokumi-imparting substance showing a different kokumi-imparting pattern, such as GSH or γ-Glu-Val-Gly, or a yeast extract containing such a substance. Moreover, an umami substance and/or a salty substance may be added to seasonings, food additives or health foods together with the yeast extract of the present invention. The tastes are classified into initial taste, middle taste, and aftertaste. Although these are relative concepts, they are usually defined as tastes sensed in the periods of 0 to 2 seconds, 2 to 5 seconds, and after 5 seconds after eating, respectively. The "initial-middle taste" mentioned above is a taste sensed in the period of 0 to 5 seconds after eating, and the "middle-after taste" mentioned later is a taste sensed in the period of 2 second to about 30 seconds after eating.

The yeast extract of the present invention can be produced by, for example, the method of the present invention described below.

The first method of the present invention is a method for producing a yeast extract containing γ-Glu-Abu, which includes the steps of culturing a yeast in a medium to which a compound selected from Abu and γ-Glu-Abu is added, and preparing a yeast extract from the obtained cells.

Any yeast from any wild-type strains, or various mutant strains or recombinant strains can be used for this invention, so long as the chosen yeast can intracellularly uptake Abu and/or γ-Glu-Abu and accumulate γ-Glu-Abu in the cells. Examples of the mutant strains or recombinant strains include a strain with enhanced activity of γ-glutamylcysteine synthetase (GSH1), a strain with attenuated activity of glutathione synthetase (GSH2), and a strain having two of the foregoing characteristics. Examples of the mutant strains or recombinant strains also include a strain with attenuated activity of a peptidase that decompose intracellular peptides, for example, an enzyme encoded by the DUG1 gene, DUG2 gene, DUGS gene, or ECM38 gene. Further, in addition to the enhanced activity of GSH1 and/or attenuated activity of GSH2, a peptidase activity of the yeast may be attenuated. The nucleotide sequences of the aforementioned genes are disclosed in the *Saccharomyces* Genome Database (http://www.yeastgenome.org/).

The yeast is not particularly limited, so long as the chosen yeast can accumulate γ-Glu-Abu in the cells thereof. Examples include yeasts belonging to the genus *Saccharomyces* such as *Saccharomyces cerevisiae*, those belonging to the genus *Candida* such as *Candida utilis*, those belonging to the genus *Pichia* such as *Pichia pastoris*, and those belonging to the genus *Schizosaccharomyces* such as *Schizosaccharomyces pombe*. Among these, *Saccharomyces cerevisiae* and *Candida utilis* are preferred, which are frequently used for production of yeast extracts. The yeast may be a monoploid, or may have diploidy or a further higher polyploidy.

Methods for enhancing activity of an enzyme or protein such as GSH1 include a method of enhancing expression of a gene coding for it. Methods for enhancing expression of a gene include a method of replacing the promoter of the gene on the chromosome with a stronger promoter, a method of inserting the target gene into the chromosome to increase copy number thereof, a method of incorporating a plasmid containing the target gene into the yeast, a method of activating a transcription factor of the gene coding for the target enzyme, and so forth.

As the promoter, a highly active conventional promoter may be obtained by using various reporter genes, or a known high expression promoter such as ADH1, PGK1, PDC1, TDH3, TEF1 and HXT7 may be used. Alternatively, for increasing copy number of a target gene, for example, a plasmid having the replication origin of CEN4, or a multi-copy plasmid having the replication origin of 2 μm DNA, to which a target gene is inserted, may be used. Furthermore, a transposon may be used in order to introduce a target gene into an arbitrary region of the chromosome, or the target gene may be introduced by using rDNA sequences as a target, which is present in a copy number of 150 in the cell.

Methods for attenuating activity of an enzyme or protein such as GSH2 and peptidase include a method of replacing the promoter of the gene coding for any of these on the chromosome with a weaker promoter to attenuate the expression, a method of introducing a mutation into the target enzyme to reduce the activity thereof, a method of deleting a part of or the entire gene of the target enzyme from the chromosome, a method of inactivating the target enzyme gene by inserting another sequence into the gene, and so forth.

The attenuated enzyme activity include the activity lower than that of a wild-type strain and complete deficiency of the enzyme activity.

Enhancement of the activity of γ-glutamylcysteine synthetase is disclosed in, for example, U.S. Pat. No. 7,553,638; Otake Y. et al., Bioscience and Industry, volume 50, No. 10, pp. 989-994, 1992, and so forth. Although disruption of the glutathione synthetase gene is disclosed in U.S. Pat. No. 7,553,638, the glutathione synthetase activity can also be reduced by inactivating YAP1, which is a transcription factor of the gene coding for γ-glutamylcysteine synthetase.

The nucleotide sequences of the genes coding for GSH1, GSH2, and YAP1 of *Saccharomyces cerevisiae* are disclosed in *Saccharomyces* Genome Database (http://www.yeastgenome.org/). The nucleotide sequences of the genes coding for GSH1 and GSH2 of *Candida utilis* are disclosed in U.S. Pat. No. 7,553,638. The nucleotide sequence of the gene coding for YAP1 of *Candida utilis* is disclosed in Japanese Patent Laid-open (Kokai) No. 2006-75122.

Such a yeast as mentioned above may be a yeast obtained by screening from nature, breeding based on mutagenesis, or breeding based on genetic engineering. For the mutagenesis, various agents such as EMS, DAPA, and NTG can be used, and an objective mutant strain can be isolated by spreading yeast cells subjected to a mutation treatment on an optimal medium, and choosing a strain of which GSH1 activity is enhanced or a strain of which GSH2 activity is attenuated from the grown strains.

The method for breeding by genetic engineering is not particularly limited, and conventional methods can be used. In particular, genetic engineering methods for *Saccharomyces cervisiae* are specifically described in many books. Moreover, various kinds of methods have been reported also for *Candida utilis* in recent years, and they may be used. Specific methods are described in such prior references as, for example, Norihiko Misawa, Chemical Engineering, June, 1999, pp. 23-28; Luis Rodriguez et al., FEMS Microbiology Letters, 165, 335-340 (1998); WO98/07873; Japanese Patent Laid-open (Kokai) No. 8-173170; WO95/32289; Keiji Kondo et al., Journal of Bacteriology, December 1995, Vol. 177, No. 24, pp. 7171-7177; WO98/14600; Japanese Patent Laid-open (Kokai) Nos. 2006-75122, 2006-75123, 2007-089441, and 2006-101867, and these can be appropriately referred to.

The method for producing the yeast extract is explained below.

First, a yeast is cultured in a medium. The medium is not particularly limited, so long as a medium in which the yeast can proliferate is chosen, and is not limited to the SD medium described in the examples. A medium usually used for industrial purposes can be used. Examples of the medium include, for example, media containing glucose, sucrose, molasses, ethanol, acetic acid, spent sulfite liquor, or the like as a carbon source, urea, ammonia, ammonium sulfate, ammonium chloride, nitrate, or the like, or corn steep liquor, casein, yeast extract, peptone, soybean protein decomposition product, or the like as a nitrogen source, phosphoric acid, potassium phosphate, ammonium phosphate, superphosphate of lime, potassium chloride, potassium hydroxide, magnesium sulfate, magnesium chloride, and so forth as phosphoric acid, potassium, and magnesium sources, and an appropriate combination of mineral salts of copper, manganese, zinc, iron ion, etc. as trace elements.

When the yeast is cultured, Abu, γ-Glu-Abu, or both of these is/are added to the aforementioned medium. Abu represents α-aminobutyric acid, and Glu represents glutamic acid. Abu and Glu are L-forms. These compounds may be present in the medium from the start of the culture, or may be added to the medium at an arbitrary time during the culture. When the compounds are added to the medium during the culture, they can be preferably added at 0 to 50 hours before the end of the culture (0 hour means that the culture is terminated immediately after the addition), more preferably 0.1 to 24 hours before the end of the culture, particularly preferably 0.5 to 6 hours before the end of the culture. Furthermore, when the peptides are added during the culture, they may be continuously added.

Abu and/or γ-Glu-Abu to be added to the medium may be a purified product (pure substance), or may be a composition containing such a compound or compounds, so long as the composition contains required amounts of these compounds.

Prior to the culture in the medium containing the compound(s), a preculture may be performed. The medium used for the preculture may or may not contain the compound(s).

When the compound is added to the medium at the start of the culture, Abu is added in an amount of usually 10 ppm or more, preferably 25 ppm or more, more preferably 50 ppm or more, further preferably 100 ppm, and γ-Glu-Abu is added in an amount of usually 1 ppm or more, preferably 5 ppm or more, more preferably 10 ppm or more, in terms of the final concentration in the culture broth at the time of the addition. When both Abu and γ-Glu-Abu are added, concentrations thereof can be determined to be within the aforementioned ranges. Although the maximum amount of the compound is not particularly limited, it is, for example, 100,000 ppm or less from an aspect of production cost, and it is usually 10,000 ppm or less, preferably 1,000 ppm or less, more preferably 500 ppm or less. When the compound is added during an arbitrary period in the middle of the culture, or it is continuously added, it may be added in a total amount equivalent to an amount that can provide the final concentration mentioned above when the compound is added in such an amount at the time of the start of the culture.

As the culture conditions, the same conditions as those used for usual production of yeast extracts can be used, and they may be suitably changed according to the chosen yeast. Arbitrary methods such as batch culture, fed-batch culture, and continuous culture may be used. When the yeast is *Saccharomyces cerevisiae* or *Candida utilis*, it is preferably aerobically cultured by shaking or the like at 25 to 35° C., more preferably 27 to 33° C., still more preferably 28 to 32° C.

If the yeast is cultured as described above, γ-Glu-Abu accumulates in the cells of the yeast. When Abu is added to the medium, Abu accumulates in the cells, and in addition, γ-Glu-Abu also accumulates. This is because Abu taken up into the cells is converted into γ-Glu-Abu by the action of intracellular γ-glutamylcysteine synthetase as shown in the example section mentioned later. As shown in the example section, the content of γ-Glu-Abu or γ-Glu-Abu-Gly in the yeast did not correlate with the content of GSH in the cells, and therefore it is considered that yeast extracts produced by the conventional methods do not contain γ-Glu-Abu at a high concentration, even if they are produced from a yeast containing GSH at a high concentration. It is estimated that this is because generation of Abu is limited in the cells as described in the example section mentioned later. According to a preferred embodiment, the yeast cultured as mentioned above contains γ-Glu-Abu in an amount of 0.04% or more, preferably 0.1% or more, more preferably 0.15% or more, still more preferably 0.2% or more, particularly preferably 0.4% or more, based on dry weight of the cells.

The yeast extract can be prepared from the obtained yeast in the same manner as that used for conventional production of yeast extracts. The yeast extract may be obtained by subjecting the yeast cells to hot water extraction and processing the extract, or by digesting the yeast cells by self-digestion or with an enzyme and processing the digestion product. Furthermore, the obtained yeast extract may be concentrated, may be in the form of paste, or may be dried and thereby made into powdered form, as required.

In such a manner as described above, a yeast extract containing an increased amount of γ-Glu-Abu can be obtained. According to a preferred embodiment, the yeast extract contains γ-Glu-Abu in an amount of 0.2% or more, more preferably 0.5% or more, still more preferably 1.0% or more, particularly preferably 2.0% or more, based on dry weight of the yeast extract.

The second method of the present invention will be explained. The second method relates to a yeast of which Abu synthesis ability is enhanced within the yeast cell. Although Abu synthetic pathway in a yeast cell had not conventionally been known, it was found that it was produced from α-ketobutyric acid with aminotransferase in yeast as shown in the example section. Therefore, if Abu synthesis ability is enhanced in a yeast cell, the γ-Glu-Abu accumulation ability is improved. The Abu synthesis ability can be enhanced by enhancing the aminotransferase activity or the α-ketobutyric acid synthetase activity. The activity of aminotransferase or α-ketobutyric acid synthetase can be enhanced in the same manner as that used for GSH1 and so forth.

One embodiment of the yeast of the present invention is a yeast of which aminotransferase activity is enhanced. Another embodiment of the yeast of the present invention is a yeast of which α-ketobutyric acid synthetase activity is enhanced. Still another embodiment of the yeast of the present invention is a yeast both of which aminotransferase activity and α-ketobutyric acid synthetase activity are enhanced. In such a yeast of which aminotransferase activity or/and α-ketobutyric acid synthetase activity are enhanced, the activity of γ-glutamylcysteine synthetase (GSH1) may be enhanced, or the activity of glutathione synthetase (GSH2) may be attenuated as in the first method of the present invention. Alternatively, the yeast may have two of these characteristics. Furthermore, a peptidase that decomposes intracellular peptides, for example, an enzyme encoded by the DUG1 gene, DUG2 gene, DUG3 gene, or ECM38 gene, may be attenuated.

A yeast of which Abu synthesis ability is enhanced, for example, a yeast modified so that the γ-glutamylcysteine synthetase activity and the aminotransferase activity, or/and the α-ketobutyric acid synthetase activity are enhanced accumulates a marked amount of γ-Glu-Abu, even when it is cultured in a medium to which Abu and γ-Glu-Abu are not added. The yeast of a preferred embodiment, for example, such a yeast of which activity of aminotransferase encoded by the BAT1 mentioned below, and the GSH1 activity are enhanced, and of which GSH2 activity is attenuated, preferably contains γ-Glu-Abu in an amount of 0.04% or more, more preferably 0.1% or more, still more preferably 0.15% or more, further preferably 0.2% or more, particularly preferably 0.4% or more, based on dry weight of the cells. A yeast extract prepared from such a yeast contains 0.2% or more of γ-Glu-Abu based on dry weight of the yeast extract.

According to another embodiment, for example, the aforementioned yeast of which activity of serine (threonine) deaminase encoded by CHA1 is further enhanced preferably contains γ-Glu-Abu in an amount of 0.1% or more, more preferably 0.15% or more, still more preferably 0.2% or more, further preferably 0.4% or more, particularly preferably 0.5% or more, based on dry weight of the cells. When a yeast of which Abu synthesis ability is enhanced is cultured, Abu and/or γ-Glu-Abu may be added to the medium.

The yeast is not particularly limited, so long as the chosen yeast can accumulate γ-Glu-Abu in the cells thereof. Examples include yeasts belonging to the genus *Saccharomyces* such as *Saccharomyces cerevisiae*, those belonging to the genus *Candida* such as *Candida utilis*, those belonging to the genus *Pichia* such as *Pichia pastoris*, and those belonging to the genus *Schizosaccharomyces* such as *Schizosaccharomyces pombe*. Among these, *Saccharomyces cerevisiae* and *Candida utilis* are preferred, which are frequently used for production of yeast extracts. The yeast may be a monoploid, or may have diploidy or a further higher polyploidy.

Examples of aminotransferase of yeast include alanine:glyoxylate aminotransferase, branched-chain amino acid transaminase, aspartate aminotransferase, γ-aminobutyrate transaminase, and so forth. The genes coding for these enzymes in *Saccharomyces cervisiae* have already been specified, and they are encoded by AGX1 (systematic name: YFL030W), BAT1 (systematic name: YHR208W), BAT2 (systematic name: YJR148W), AAT1 (systematic name: YKL106W), AAT2 (systematic name: YLR027C), and UGA1 (systematic name: YGR019W), respectively. Moreover, various genes have been also reported for *Candida utilis* in recent years, and homologue genes thereof can also be easily specified by identifying the total genome sequence using recent advanced sequencers, and used. Among these, BAT1 and UGA1 are preferred, and BAT1 is particularly preferred, since it shows a marked effect as described in the example section described later. Although activity of one kind of aminotransferase may be enhanced, activities of arbitrary two or more kinds of aminotransferases may also be enhanced.

Examples of the α-ketobutyric acid synthetase of yeast include the serine (threonine) deaminase encoded by the CHA1 gene (systematic name: YCL064C), and the threonine deaminase encoded by the ILV1 gene (systematic name: YER086W). Although activity of one kind of α-ketobutyric acid synthetase may be enhanced, activities of arbitrary two or more kinds of α-ketobutyric acid synthetases may also be enhanced.

The activities of aminotransferase and α-ketobutyric acid synthetase can be enhanced by enhancing expression of genes coding for the enzymes as in the case of enhancement of the GSH1 activity.

Production of a yeast extract using a yeast having enhanced activity of aminotransferase or/and enhanced activity of α-ketobutyric acid synthetase, and containing γ-Glu-Abu can be performed in the same manner as that explained for the first method.

The third method of the present invention is a method for producing a yeast extract containing γ-Glu-Abu, which includes the step of allowing a γ-glutamyltransferase to act on a yeast extract raw material to which Abu has been added.

If a γ-glutamyltransferase is allowed to act on Abu, γ-Glu-Abu is generated. Therefore, a yeast extract containing γ-Glu-Abu can also be obtained by allowing a γ-glutamyltransferase to act on a yeast extract containing Abu. The yeast extract containing Abu may be prepared from a yeast cultured in a medium containing Abu, or may be obtained by adding Abu to a yeast extract raw material.

As the yeast extract raw material, a yeast extract obtained by a conventional method can be used.

Abu is usually added to the yeast extract in an amount of 0.1% or more, preferably 1% or more, more preferably 5% or more, still more preferably 10% or more, based on dry weight of the yeast extract raw material.

The reaction catalyzed by the γ-glutamyltransferase is performed in an aqueous solvent such as water or buffers. Specifically, for example, the yeast extract raw material is dissolved in the aqueous solvent, and the γ-glutamyltransferase is added. The reaction conditions can be suitably determined according to the γ-glutamyltransferase to be used. The reaction is usually allowed at pH 3 to 9 and 15 to 70° C. for 1 to 300 minutes, preferably at pH 5 to 8 and 30 to 70° C. for 5 to 150 minutes.

Concentration of the yeast extract raw material in the aqueous solvent may be determined in view of ease of handling. The concentration is usually 0.1 to 50%, preferably 0.5 to 20%, in terms of dry weight of the yeast extract raw material.

Examples of the γ-glutamyltransferase include glutaminase, γ-glutamyl transpeptidase (γ-GTP), and so forth. As for the amount of the enzyme, in the case of γ-GTP, it is usually 0.001 to 1000 units/ml, preferably 0.005 to 100 units/ml, more preferably 0.01 to 25 units/ml, most preferably 0.05 to 10 units/ml, wherein 1 unit is defined to be the activity of liberating 1.0 μmole of p-nitroaniline from γ-glutamyl-p-nitroanilide per 1 minute in a solution at pH 8.5 and 25° C. (definition described in Sigma General Catalogue, 2008-2009 Edition, p. 917). The amount of glutaminase can also be determined in a manner similar to that for γ-GTP.

After the enzymatic reaction, a treatment for inactivating the γ-glutamyltransferase, for example, a heat treatment at 80 to 100° C., may be performed, or may not be performed.

As a substrate of the γ-glutamyltransferase, a γ-glutamyl compound, for example, GSH, may be added to the reaction mixture. GSH contained in the yeast extract may also be used as a substrate. In this case, a yeast extract prepared from a yeast in which the content of GSH is increased, for example, a yeast in which activities or activity of GSH1 and/or GSH2 is enhanced, can be used. Although a greater GSH content in the yeast extract is more preferred, it is usually 1 to 50%, preferably 1 to 30%, more preferably 5 to 20%, based on dry weight of the yeast extract. Alternatively, glutamine can also be used like GSH.

In such a manner as described above, a yeast extract in which the amount of γ-Glu-Abu is increased is obtained. According to a preferred embodiment, the yeast extract contains γ-Glu-Abu in an amount of 0.02% or more, more preferably 0.5% or more, still more preferably 1.0% or more, particularly preferably 2.0% or more, based on dry weight of the yeast extract.

The obtained yeast extract may be concentrated, or may be in the form of paste, or may be dried and thereby made into powdered form, as required.

Another kokumi substance may be added to a yeast extract obtained by any of the aforementioned first to third methods of the present invention. Examples of such a kokumi substance include, for example, a peptide such as γ-Glu-X and γ-Glu-X-Gly (X represents an amino acid or an amino acid derivative), specifically GSH and γ-Glu-Val-Gly, and a yeast extract containing these. As described above, a yeast extract that has kokumi for a broad range from the initial taste to aftertaste can be produced. In the case of GSH, in particular, in view of the balance of kokumi of the initial taste and the aftertaste, the ratio of GSH with respect to γ-Glu-Abu is preferably 0.3 or more, more preferably 0.5 or more, still more preferably 1.0 or more, particularly preferably 3.0 or more.

EXAMPLES

Hereafter, the present invention will be more specifically explained with reference to examples. However, the present invention is no way limited by the following examples. Unless specially mentioned, the amino acids and amino acid derivatives mentioned in the examples are L-forms.

Reference Example 1: Evaluation of Kokumi-Imparting Activity of γ-Glu-Abu

Degree of kokumi-imparting activity of γ-Glu-Abu was investigated through a quantitative organoleptic evaluation test.

The quantitative organoleptic evaluation test was carried out as follows. Strength of the kokumi-imparting activity of a test compound was measured by using a mixture containing the test compound at 0.001 to 0.5 g/dl in distilled water containing sodium glutamate (0.05 g/dl), inosine monophosphate (0.05 g/dl), and sodium chloride (0.5 g/dl). A sample of the distilled water containing sodium glutamate, inosine monophosphate, and sodium chloride to which any test compound was not added was used as a no addition control. Samples that became acidic relative to the no addition control after dissolution of the test compound were used after pH of them was adjusted with NaOH to be within the range of ±0.2 from that of the no addition control.

The test was performed with organoleptic scores of 0 for the control, 3 for strong effect, and 5 for extremely strong effect, and n=4. Moreover, in order to make the criteria more definite, the scores of 0.001 g/dl of γ-Glu-Val-Gly for the initial taste and the middle-after taste were defined to be 3.0. The "middle-after taste" is a taste sensed in the periods for the middle taste and the aftertaste. Specifically, the initial taste, middle taste, and aftertaste are tastes sensed in the periods of 0 to 2 seconds, 2 to 5 seconds, and after 5 seconds, after eating, respectively, and the "middle-after taste" is a taste sensed in the period from 2 seconds to around 30 seconds. For the scoring, the linear scale method was used, in which determined scores were noted on a straight line on which positions of scores of from −5 to 5 were indicated. The panelists were consisted of persons who had experience of development of seasonings for foodstuffs for one year or longer in total, and could judge the difference of the titers of γ-Glu-Cys-Gly and γ-Glu-Val-Gly added to the tasty and salty solution to be about 10 times (this ability was periodically confirmed). Although γ-Glu-Abu showed kokumi-imparting activity in a broad range within the aforementioned addition concentration range, the result for a typical concentration is shown in Table 1.

The result of similar evaluation for γ-Glu-Ala is also shown in Table 2. The both are initial taste-imparting type substances giving high scores for the initial taste, but it was found that γ-Glu-Abu was a dipeptide showing an extremely high titer.

TABLE 1

| Compound | Concentration (g/dl) | Intensity of kokumi | | Organoleptic evaluation profile |
|---|---|---|---|---|
| | | Initial taste | Middle-after taste | |
| γ-Glu-Abu | 0.005 | 3.8 | 3.2 | Atsumi (total taste and harmony) was enhanced from initial taste. |
| γ-Glu-Ala | 0.2 | 4.5 | 4.3 | Tastes belonging to acidic and sweet tastes were enhanced from initial taste. |

Kokumi-imparting activities of γ-Glu-Cys and other dipeptides were determined by the same quantitative organoleptic evaluation test as mentioned above. The results are shown in Table 2.

TABLE 2

| Compound | Concentration (g/dl) | Intensity of kokumi | | Organoleptic evaluation profile |
|---|---|---|---|---|
| | | Initial taste | Middle-after taste | |
| γ-Glu-Cys | 0.01 | 3.1 | 3.1 | Middle-after taste was mainly enhanced, and slight sulfur smell was sensed. |
| γ-Glu-Ser | 0.2 | 3.6 | 3.0 | Strong initial taste was obtained, but strange taste was sensed. |
| γ-Glu-Val | 0.01 | 3.1 | 2.4 | Aftertaste was extremely weak. |

It was found that γ-Glu-Abu had superior kokumi-imparting activity, and showed marked rise of the initial taste in the taste pattern. This rise of the initial taste is one of the extremely advantageous characteristics of γ-Glu-Abu compared with γ-Glu-Cys. Moreover, γ-Glu-Abu shows superior storage stability, and this is also one of the advantageous characteristics compared with γ-Glu-Cys. Further, since the number of residues contained in γ-Glu-Abu is as small as two, it can be more easily produced at lower cost compared with tripeptides containing three amino acid residues, and this is industrially extremely advantageous.

Example 1: Detection of Abu, γ-Glu-Abu and γ-Glu-Abu-Gly in Various Yeast Extracts Abu, γ-Glu-Abu and γ-Glu-Abu-Gly contents in various yeast extracts were measured by fluorescence derivatization of the compounds with 6-aminoquinolyl-N-hydroxysuccinimidyl carbamate (AQC), and detection by LC-MS/MS according to the method described below. Specifically, to 2.5 μL of a sample diluted to an appropriate concentration, or 2.5 μL each of standard solutions containing 1 μM Abu, γ-Glu-Abu or γ-Glu-Abu-Gly, 2.5 μL of Milli-Q water, 5 μL of a 5 μM internal standard substance solution (3-methyl-His-d2 (Sigma) or Gly-d2 (Sigma), both are labeled with stable isotope), and 30 μL of a borate buffer (attached to AccQ-Fluor (registered trademark) Reagent Kit, Nihon Waters) were added. To each mixture, 10 μL of an AQC reagent solution (prepared by dissolving the reagent powder of the aforementioned reagent kit in 1 mL of acetonitrile) was added. This mixture was heated at 55° C. for 10 minutes, and then 100 μL of 0.1% formic acid aqueous solution was added to the mixture to prepare a sample for analysis.

Then, the sample for analysis prepared as described above was subjected to separation by the reverse phase liquid chromatography described below, and then introduced into a mass spectrometer. The separation conditions were as follows.
(1) HPLC: Agilent 1200 Series
(2) Separation column: Unison UK-Phenyl; internal diameter, 2.0 mm; length, 100 mm; particle size, 3 μm (Imtakt)
(3) Column oven temperature: 40° C.
(4) Mobile phase A: 25 mM Ammonium formate (pH 6.0, adjusted with aqueous ammonia)
(5) Mobile phase B: methanol
(6) Flow rate: 0.25 mL/min
(7) Elution conditions: Elution was performed by using mixtures of the mobile phase A and the mobile phase B. The ratios of the mobile phase B to the mixtures are as follows: 0 minute (5%), 0 to 17 minutes (5 to 40%), 17 to 17.1 minutes (40 to 80%), 17.1 to 19 minutes (80%), 19 to 19.1 minutes (80 to 5%), 19.1 to 27 minutes (5%).

Then, derivatized compounds of Abu, γ-Glu-Abu, and γ-Glu-Abu-Gly eluted under the aforementioned separation conditions were introduced into a mass analyzer, and quantified by mass chromatography. The analysis conditions were as follows.
(1) Mass analyzer: AB Sciex API3200 QTRAP
(2) Detection mode: Selected Ion Monitoring (positive ion mode)
(3) Selected ion: Table 3

TABLE 3

| Derivatized compound | First mass analyzer (Q1) | Second mass analyzer (Q3) |
|---|---|---|
| Abu | 274.2 | 171.1 |
| γ-Glu-Abu | 403.4 | 171.1 |
| γ-Glu-Abu-Gly | 460.4 | 171.1 |
| 3-methyl-His-d2 | 343.4 | 171.1 |
| Gly-d2 | 248 | 171.1 |

Figure 2:
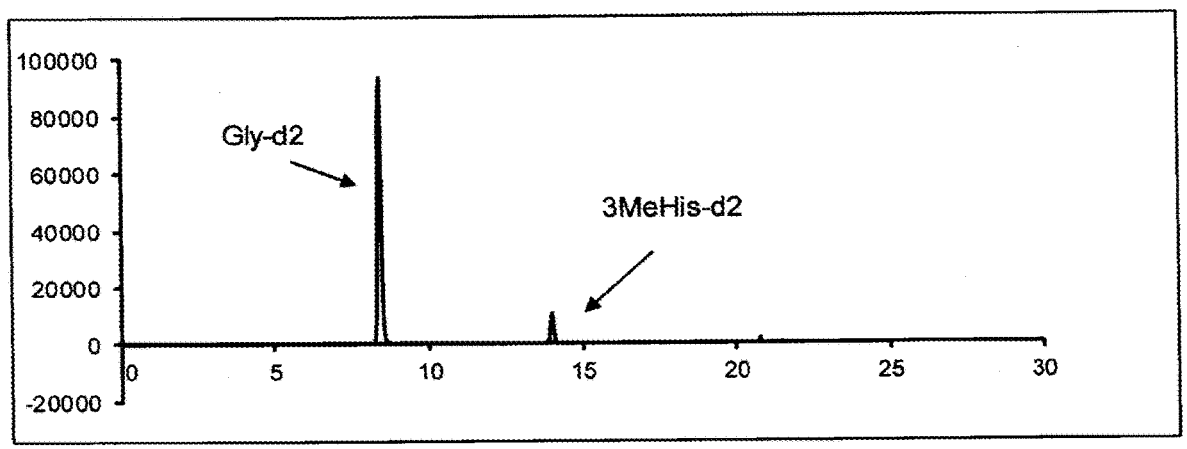
FIG. 2 shows mass chromatograms of internal standard substances (3-methyl-His-d2, Gly-d2). In the mass chromatogram, 3MeHis-d2 represents 3-methyl-His-d2.

The derivatized compounds of Abu, γ-Glu-Abu, and γ-Glu-Abu-Gly were quantified by using analysis software, Analyst ver. 1.4.2 (AB Sciex). As the internal standard substance for performing the quantification, a derivatized compound of 3-methyl-His-d2 was used in the case of the derivatized compound of Abu, and a derivatized compound of Gly-d2 was used in the case of the derivatized compounds of γ-Glu-Abu and γ-Glu-Abu-Gly. The analysis results (mass chromatograms) of Abu, γ-Glu-Abu, and γ-Glu-Abu-Gly as well as the derivatized internal standard amino acid are shown in FIGS. 1 and 2. It was found that, by using this method, Abu, γ-Glu-Abu, and γ-Glu-Abu-Gly in various samples could be measured.

At the time of the quantification of γ-Glu-Abu, a contaminated peak was very rarely observed, and in such a case, the quantification was performed by using selected ion of 145.2 or 104.1 for the second mass analyzer.

Example 2: Measurement of γ-Glu-Abu Content in Various Commercially Available Yeast Extracts γ-Glu-Abu contents in various commercially available yeast extracts (based on dry weight of the yeast extracts) were measured by using the method of Example 1. GSH contents were also measured in a conventional manner. The results are shown in Table 4.

TABLE 4

|  | γ-Glu-Abu | γ-Glu-Abu-Gly | GSH | γ-Glu-Abu/GSH |
| --- | --- | --- | --- | --- |
| Brand A | 109 ppm | 348 ppm | 1461 ppm | 0.075 |
| Brand B | 15 ppm | 50 ppm | 186 ppm | 0.080 |
| Brand C | 95 ppm | 440 ppm | 874 ppm | 0.108 |
| Brand D | 424 ppm | 249 ppm | 11478 ppm | 0.037 |
| Brand E | 920 ppm | 316 ppm | 66521 ppm | 0.014 |

As shown in Table 4, the γ-Glu-Abu contents in various yeast extracts were in the range of 15 to 920 ppm. Further, the γ-Glu-Abu/GSH ratio was not constant, and in particular, there was observed a tendency that the ratio was more decreased in a yeast extract having a higher GSH content. It is considered that this is because GSH1 and GSH2 responsible for the GSH biosynthetic pathway can recognize Abu and γ-Glu-Abu as a substrate, but first of all, the intracellular generation amount of Abu is limited, and even if the generation pathway of GSH is enhanced, a large amount of γ-Glu-Abu cannot be accumulated due to lack of Abu, as shown in the following examples. This suggests that the γ-Glu-Abu content in the known high GSH content yeasts is not so high.

Example 3: Effect of Addition of Abu to *Saccharomyces* Cervisiae Type Strain, S288C Strain Then, γ-Glu-Abu content in the S288C strain, which is a type strain of *Saccharomyces* cervisiae, was measured. Moreover, effect of addition of the precursor, Abu, to the medium was also investigated. The S288C strain is deposited at the independent administrative agency, National Institute of Technology and Evaluation, Biological Resource Center (NBRC, NITE Biological Resource Center, 2-5-8 Kazusakamatari, Kisarazu-shi, Chiba-ken, 292-0818, Japan) with the number of NBRC 1136, and can be provided therefrom. This strain is also deposited at the American Type Culture Collection (12301 Parklawn Drive, Rockville, Md. 20852, United States of America) with the number of ATCC 26108, and can be provided therefrom.

One loop of the S288C strain was inoculated into the SD medium (50 ml in 500 ml-volume Sakaguchi flask), and cultivated at 30° C. for 24 hours with shaking at a velocity of 120 rpm.

Composition of SD Medium:

| Glucose | 2% |
| --- | --- |
| Nitrogen Base | 1-fold concentration |

(Nitrogen Base of 10-fold concentration was obtained by dissolving a mixture of 1.7 g of Bacto Yeast Nitrogen Base w/o Amino Acids and Ammonium Sulfate (Difco) and 5 g of ammonium sulfate in 100 ml of sterilized water, adjusting the solution to about pH 5.2, and sterilizing the solution by filter filtration.)

Absorbance of the obtained culture broth was measured, the culture broth was inoculated into the SD medium or the SD medium containing 10, 50 or 100 ppm of Abu as the final concentration (400 ml in a 2 L-volume conical flask with baffle fins), so that OD660 was 0.01 at the start of the culture (absorbance was measured by using DU640 SPECTROPHTOMETER, BECKMAN COULTER), and the yeast cells were cultivated at 30° C. for 19 hours with shaking by rotation at a velocity of 120 rpm. From the obtained culture broth, 400 OD units of the cells (1 OD unit is defined as cells contained in 1 ml of culture broth of which OD660 is 1) were collected by centrifugal separation. The supernatant was removed as much as possible, and the residual cells were suspended in 45 ml of Milli-Q water. The cells were collected again by centrifugal separation, and resuspended in 45 ml of Milli-Q water. By repeating this operation 3 times in total, the medium was completely removed from the cells. The washed cells were suspended in about 1.5 ml of Milli-Q water, and the suspension was heated at 70° C. for 10 minutes. By this step, the extractable components contained in the cells were extracted. Then, the extract and the cell residue were separated by centrifugation.

Cell debris were removed from the extract using a centrifugal filtration membrane of 10 kDa cutoff (Amicon Ultra—0.5 mL 10K, MILLIPORE, Catalogue Number UFC501096)), the obtained fraction was derivatized with the AQC reagent in the same manner as that used in Example 1, and Abu, γ-Glu-Abu, and γ-Glu-Abu-Gly were measured by LC-MS/MS. Furthermore, dry cell weight was measured after the washed cells were dried at 104° C. for 4 hours. From the amounts of Abu, γ-Glu-Abu, and γ-Glu-Abu-Gly contained in a certain volume of culture broth and dry cell weight measured as described above, the contents of Abu, γ-Glu-Abu, and γ-Glu-Abu-Gly based on weight of dried cells were calculated. The results are shown in Table 5.

TABLE 5

|  | Abu (ppm) | γ-Glu-Abu (ppm) | γ-Glu-Abu-Gly (ppm) |
| --- | --- | --- | --- |
| SD medium | 2 | 22 | 28 |
| Medium containing Abu (10 ppm) | 33 | 170 | 51 |
| Medium containing Abu (50 ppm) | 564 | 1025 | 155 |
| Medium containing Abu (100 ppm) | 450 | 1828 | 615 |

As shown in Table 5, it was found that, by adding Abu to the medium, the γ-Glu-Abu content in the cells was increased. Moreover, since not only γ-Glu-Abu but also γ-Glu-Abu-Gly accumulated, it was found that a part of γ-Glu-Abu was converted into γ-Glu-Abu-Gly by a certain enzymatic reaction using γ-Glu-Abu as a substrate in the yeast cells.

In addition, Abu in the washing solution obtained in the cell washing step was measured, but Abu was not contained in the final washing solution. The cell washing operation was performed further once again, and therefore it was confirmed that Abu in the medium was fully removed by the four-step separation in the washing step, and was not carried over into the cell extract. Further, γ-Glu-Abu was not detected in the final washing solution also in the γ-Glu-Abu addition experiments described in the examples mentioned below.

Example 4: Effect of Addition of γ-Glu-Abu to S288C Strain (1)

Then, effect of addition of γ-Glu-Abu to the medium at the time of culturing the S288C strain was investigated. One loop of the S288C strain was inoculated into the SD medium (50 ml in a 500 ml-volume Sakaguchi flask), and cultivated at 30° C. for 24 hours with shaking at a velocity of 120 rpm. Absorbance of the obtained culture broth was measured (absorbance was measured by using DU640 SPECTROPHTOMETER, BECKMAN COULTER), the culture broth was inoculated into the SD medium or the SD medium containing 10 or 100 ppm of γ-Glu-Abu as the final concentration (400 ml in a 2 L-volume conical flask with baffle fins), so that OD660 was 0.01 at the start of the culture, and the yeast cells were cultivated at 30° C. for 19 hours with shaking by rotation at a velocity of 120 rpm. Extract was obtained from the obtained culture broth in the same manner as that of Example 3, and contents of the compounds in the cells were measured.

As shown in Table 6, it was found that when the S288C strain was cultured in a medium containing γ-Glu-Abu, the S288C strain took up γ-Glu-Abu in the medium and accumulated it in the cells. Moreover, not only γ-Glu-Abu, but also γ-Glu-Abu-Gly was accumulated, as in Example 3.

TABLE 6

|  | γ-Glu-Abu (ppm) | γ-Glu-Abu-Gly (ppm) |
|---|---|---|
| SD medium | 21 | 39 |
| Medium containing γ-Glu-Abu (10 ppm) | 1796 | 657 |
| Medium containing γ-Glu-Abu (100 ppm) | 23338 | 2986 |

Example 5: Effect of Addition of γ-Glu-Abu to S288C Strain (2)

Then, effect of delayed addition of γ-Glu-Abu to the medium at the time of culturing the S288C strain was investigated. One loop of the S288C strain was inoculated into the SD medium (50 ml in a 500 ml-volume Sakaguchi flask), and cultivated at 30° C. for 24 hours with shaking at a velocity of 120 rpm. Absorbance of the obtained culture broth was measured (absorbance was measured by using DU640 SPECTROPHTOMETER, BECKMAN COULTER), the culture broth was inoculated into the SD medium (400 ml in a 2 L-volume conical flask with baffle fins), so that OD660 was 0.01 at the start of the culture, and the yeast cells were cultivated at 30° C. for 18 hours with shaking by rotation at a velocity of 120 rpm. Then, γ-Glu-Abu was added at 10 ppm or 100 ppm as the final concentration for the experiment utilizing delayed addition of γ-Glu-Abu to the medium, or no substance was added for the control, and the culture was continued for further 1 hour (total culture time was 19 hours). Extract was obtained from the obtained culture broth in the same manner as that of Example 3, and contents of the compounds in the cells were measured.

As shown in Table 7, it was found that γ-Glu-Abu in the medium could be uptaken into the cells and accumulated in the cells as in Example 4, even when γ-Glu-Abu was added afterward. Moreover, not only γ-Glu-Abu, but also γ-Glu-Abu-Gly accumulated, as in Examples 3 and 4.

TABLE 7

|  | γ-Glu-Abu (ppm) | γ-Glu-Abu-Gly (ppm) |
|---|---|---|
| SD medium | 21 | 39 |
| Medium added γ-Glu-Abu (10 ppm) afterward | 2330 | 1430 |
| Medium added γ-Glu-Abu (50 ppm) afterward | 12545 | 3106 |
| Medium added γ-Glu-Abu (100 ppm) afterward | 10241 | 2055 |

Example 6: γ-Glu-Abu Content Based on Solid Content of Yeast Extract

Solid contents of the extracts obtained in Examples 3 to 5 were measured, and γ-Glu-Abu contents based on the solid contents of the extracts were calculated from the γ-Glu-Abu contents based on dry cell weight. As a result, it was found that the γ-Glu-Abu content markedly increased compared with commercially available yeast extracts.

TABLE 8

|  | γ-Glu-Abu (ppm) |
|---|---|
| SD medium | 123 |
| Medium containing Abu (10 ppm) | 1013 |
| Medium containing Abu (50 ppm) | 5068 |
| Medium containing Abu (100 ppm) | 8250 |
| Medium containing γ-Glu-Abu (10 ppm) | 8970 |
| Medium containing γ-Glu-Abu (100 ppm) | 97316 |
| Medium added γ-Glu-Abu (10 ppm) afterward | 11639 |
| Medium added γ-Glu-Abu (50 ppm) afterward | 62104 |
| Medium added γ-Glu-Abu (100 ppm) afterward | 55382 |

Example 7: Effect of Addition of Abu to *Candida utilis* Type Strains, NBRC 10707 Strain and NBRC 0988 Strain Then, effect of addition of Abu to the *Candida utilis* type strains, NBRC 10707 strain and NBRC 0988 strain, was investigated. These strains are deposited at the independent administrative agency, National Institute of Technology and Evaluation, Biological Resource Center (NBRC, NITE Biological Resource Center, 2-5-8 Kazusakamatari, Kisarazu-shi, Chiba-ken, 292-0818, Japan) with the number of NBRC 10707 and NBRC 0988, and can be provided therefrom.

One loop each of the NBRC 10707 strain and NBRC 0988 strain was inoculated into the SD medium (50 ml in a 500 ml-volume Sakaguchi flask), and cultivated at 30° C. for 24 hours with shaking at a velocity of 120 rpm. Absorbance of the obtained culture broth was measured (absorbance was measured by using DU640 SPECTROPHTOMETER, BECKMAN COULTER), the culture broth was inoculated into the SDP medium (400 ml in a 2 L-volume conical flask with baffle fins, corresponding to the SD medium described in Example 3, provided that 5 g of ammonium sulfate was replaced with 1 g of proline at the time of preparing Yeast Nitrogen Base of 10-fold concentration), so that OD660 was 0.01 at the start of the culture, and the yeast cells were cultivated at 30° C. with shaking by rotation at a velocity of 120 rpm. The NBRC 10707 strain was cultivated for 46.5 hours, and the NBRC 0988 strain was cultivated for 22.5 hours to attain the logarithmic phase for each strain. Then, Abu was added at a final concentration of 100 ppm, and the culture was continued for further 1 hour. As a control group, cultivation was continued for 1 hour without adding the compound. The absorbance of the culture broth to which Abu was added afterward was about 4.5 after the culture, and residual saccharides were also detected. An extract was obtained from the obtained culture broth in the same manner as that of Example 3, and contents of the compounds in the cells were measured. The results are shown in Tables 9 and 10. As a result, without the addition of Abu, γ-Glu-Abu was not detected in the cells, but with addition of Abu, γ-Glu-Abu was detected in the cells. Also from these results, it was found that supply of Abu was important for accumulation of γ-Glu-Abu.

TABLE 9

NBRC 10707 strain

| | Abu content (ppm) | γ-Glu-Abu content (ppm) | γ-Glu-Abu-Gly content (ppm) |
|---|---|---|---|
| Abu not added | 0 | 0 | 3 |
| Abu added | 2004 | 247 | 1094 |

TABLE 10

NBRC 0988 strain

| | γ-Glu-Abu content (ppm) | γ-Glu-Abu-Gly content (ppm) |
|---|---|---|
| Abu not added | 0 | 2 |
| Abu added | 107 | 601 |

Example 8: Analysis of Substrate Specificity of Yeast GSH1

Since it was found that γ-Glu-Abu was produced by a certain enzymatic reaction using Abu as a substrate in the yeast cells on the basis of the results of Example 3, possibility of side reaction with γ-glutamylcysteine synthetase was investigated.
1) Construction of Plasmid pET-GSH1 for Expression of Yeast-Derived γ-Glutamylcysteine Synthetase Gene (GSH1)
A plasmid pET-GSH1 for expression of the GSH1 gene coding for γ-glutamylcysteine synthetase of the *Candida utilis* ATCC 22023 strain was constructed by the following procedures, and introduced into *Escherichia coli*. This strain is deposited at the American Type Culture Collection (12301 Parklawn Drive, Rockville, Md. 20852, United States of America) with the number of ATCC 22023, and can be provided therefrom.
(1-1) Construction of Plasmid pAUR-GSH1 for Expression of Yeast GSH1
First, a plasmid pAUR-GSH1 for expression of yeast GSH1 was constructed by the following procedure. The construction was entrusted to Takara Bio.

By PCR using Primer G (SEQ ID NO: 3) and Primer H (SEQ ID NO: 4), which were produced on the basis of the nucleotide sequence (SEQ ID NO: 1) of the GSH1 gene of the *Candida utilis* ATCC 22023 strain, as well as the chromosomal DNA of the ATCC 22023 strain as the template, the sequence containing the GSH1 gene was amplified. Primer G consisted of a region containing the start codon of the GSH1 gene in the chromosomal DNA of the ATCC 22023 strain, to which the KpnI recognition sequence and a partial sequence of the yeast expression plasmid pAUR123 (Takara Bio) were added at the 5' end. Primer H consisted of a nucleotide sequence complementary to the C-terminal nucleotide sequence of the GSH1 gene, to which a nucleotide sequence complementary to the sequence coding for the His-tag, a nucleotide sequence complementary to the stop codon (TAA), the XbaI recognition sequence, and a partial sequence of pAUR123 were added. PCR was performed by using PrimeSTAR Max DNA Polymerase (Takara Bio) according to the protocol described in the attached manual. The amplified fragment was introduced into pAUR123 (Takara Bio) at the KpnI-XbaI site by using In-Fusion Advantage PCR Cloning Kit (Takara Bio) to construct the plasmid pAUR-GSH1 for expression of yeast GSH1.
(1-2) Construction of Plasmid pET-GSH1 for Expression of GSH1 of *Escherichia coli*
Then, a GSH1 expression plasmid pET-GSH1 for *Escherichia coli* was constructed by the following procedure.
Primer I (SEQ ID NO: 5) and Primer J (SEQ ID NO: 6) were purchased from Japan Bio Service, which were prepared on the basis of the nucleotide sequence of the GSH1 gene of the *Candida utilis* ATCC 22023 strain (SEQ ID NO: 1). Primer I consisted of a region containing the start codon of the GSH1 gene in the chromosomal DNA of the *Candida utilis* ATCC 22023 strain, to which a nucleotide sequence containing the SpeI recognition sequence was added at the 5' end. Primer J consisted of a nucleotide sequence complementary to the nucleotide sequence outside from the stop codon of the GSH1 gene in pAUR-GSH1 mentioned above, to which a nucleotide sequence containing the XhoI recognition sequence was added at the 5' end.
By PCR using Primer I and Primer J, as well as the aforementioned pAUR-GSH1 as the template, the sequence containing the GSH1 gene was amplified. PCR was performed by preparing 50 μl of a reaction mixture containing the plasmid DNA, 0.2 μmol/L each of the primers, 1.25 units of PrimeSTAR HS DNA Polymerase (Takara Bio), 10 μL of the 5× PrimeSTAR buffer (Takara Bio), and 2.5 mmol/L each of dNTPs (dATP, dGTP, dCTP, and dTTP), and subjecting the reaction mixture to warming at 98° C. for 10 seconds, then 30 cycles of 98° C. for 10 seconds, 56° C. for 5 seconds and 72° C. for 2 minutes, and further warming at 72° C. for 1 minute.
The reaction mixture after PCR (3 μl) was subjected to agarose gel electrophoresis to confirm that a DNA fragment of about 2.0 kb corresponding to the GSH1 gene fragment was amplified, and then the DNA fragment was purified from the remaining reaction mixture by using Ethachinmate (NIPPON GENE), and dissolved in 25 μl of dH$_2$O. Then, the DNA fragment in the whole volume of the obtained DNA solution was digested with the restriction enzymes SpeI and XhoI, then purified by using MinElute Reaction Cleanup Kit (QIAGEN), and dissolved in 15 μl of Buffer EB (10 mM Tris-HCl, pH 8.5, QIAGEN).
The expression plasmid pET-21a(+) (1 μg, Novagen) was digested with the restriction enzymes NheI and XhoI, then purified by using MinElute Reaction Cleanup Kit, and dissolved in 15 μl of Buffer EB. Then, the DNA fragment in the whole volume of the obtained DNA solution was dephosphorylated with an alkaline phosphatase (calf intestine alkaline phosphatase, CIAP), then purified by using MinElute Reaction Cleanup Kit, and dissolved in 10 μl of Buffer EB.

The DNA fragment of about 2.0 kb containing the GSH1 gene obtained above, and the DNA fragment of about 5.4 kb of the expression plasmid pET-21a(+) (Novagen) obtained above were reacted at 16° C. for 30 minutes by using TaKaRa Ligation Kit Ver. 2.1 (Takara Bio), and thereby ligated. Competent cells of the *Escherichia coli* DH5α strain (Takara Bio) were transformed by the heat shock method using the above reaction mixture, and the transformants were applied on the LB [10 g/L of Bacto tryptone (Difco), 5 g/L of yeast extract (Difco), and 5 g/L of sodium chloride (Wako)] agar medium containing 100 μg/ml of ampicillin, and cultured overnight at 37° C.

From the grown colonies of the transformants, a plasmid was extracted by a known method, and the nucleotide sequence thereof was determined by a known method. The obtained plasmid was a plasmid consisting of the GSH1 gene derived from the *Candida utilis* ATCC 22023 strain having the sequence coding for the His-tag at the 3' end, which was ligated to T7 promoter on the downstream side, and this plasmid was designated pET-GSH1. The nucleotide sequence of the GSH1 gene derived from the *Candida utilis* ATCC 22023 strain and the amino acid sequence encoded thereby are shown in SEQ ID NOS: 1 and 2, respectively.

Then, competent cells of the *Escherichia coli* Rosetta2 (DE3)pLysS strain (Novagen) were transformed with pET-GSH1 by the heat shock method, and the transformants were applied on the LB agar medium containing 100 μg/ml of ampicillin and 30 μg/ml of chloramphenicol, and cultured overnight at 37° C. Plasmids were extracted from the grown colonies of the transformants in a known manner, and the structures thereof were analyzed by using restriction enzymes to confirm that the transformants harbored pET-GSH1. The *Escherichia coli* Rosetta2(DE3)pLysS strain harboring pET-GSH1 was designated *Escherichia coli* Rosetta2(DE3)pLysS/pET-GSH1.

2) Purification of C-Terminal his-Tag-Added Recombinant Gsh1

*Escherichia coli* Rosetta2(DE3)pLysS/pET-GSH1 obtained as described above was inoculated into 3 mL of the LB medium containing 100 μg/ml of ampicillin and 30 μg/ml of chloramphenicol contained in a test tube, and cultured at 37° C. for 16 hours with shaking. The obtained culture broth (2 ml) was inoculated into 100 ml of the LB medium contained in a Sakaguchi flask. Culture was performed at 37° C. for 2 hours with shaking, then isopropyl-β-D-thiogalactopyranoside (IPTG) was added at a final concentration of 0.5 mmol/L, and culture was further continued at 30° C. for 4 hours. The culture broth was centrifuged to obtain wet cells.

The wet cells were suspended in 10 ml of a 100 mmol/L Tris-hydrochloric acid buffer (pH 8.0) containing 300 mM sodium chloride, the cells were disrupted by ultrasonication, and the suspension was centrifuged. From the obtained supernatant, His-tag added recombinant Gsh1 was purified by using a His-tag-added protein purification kit, Ni Sepharose 6 Fast Flow (GE Healthcare), according to the protocol described in the attached manual, and then desalted by using PD-10 column (GE Healthcare) according to the protocol described in the attached manual. This purified and desalted Gsh1 was used for the following experiments as purified Gsh1.

3) Analysis of Substrate Specificity of GSH1

A reaction mixture (pH 8.0, 200 μl) containing the purified recombinant GSH1 obtained above (24.6 μg), 100 mmol/L of Tris-HCl (pH 8.0), 12.5 mmol/L of Abu, 12.5 mmol/L of glutamic acid, 12.5 mmol/L of adenosine triphosphate (ATP), 12.5 mmol/L of magnesium sulfate, and 2 mmol/L of dithiothreitol (DTT) was prepared, and the reaction was performed at 37° C. for 16 hours.

After completion of the reaction, the reaction product was analyzed by HPLC. The analysis conditions were as follows.
(1) HPLC: HITACHI L-2000 Series
(2) Isolation column: Synergi 4μ Hydro-RP 80A; internal diameter, 4.6 mm; length, 250 mm; particle size, 4 μm (Phenomenex)
(3) Column temperature: 40° C.
(4) Mobile phase A: 50 mM phosphate buffer (pH 2.5)
(5) Mobile phase B: acetonitrile
(6) Flow rate: 1.0 ml/minute
(7) Elution conditions: Elution was performed by using a mixture of the mobile phase A and the mobile phase B. The ratio of the mobile phase B in the mixture was as follows: 0 minute (0%), 0 to 5 minutes (0 to 2.5%), 5 to 15 minutes (2.5%), 15 to 30 minutes (2.5 to 40%), 30 to 30.1 minutes (40 to 0%), and 30.1 to 50 minutes (0%).
(8) Detection: UV 210 nm As a result of the aforementioned measurement, the retention time of the peak of the reaction product agreed with that of a γ-Glu-Abu sample, and it was judged that the product was γ-Glu-Abu. As a result of quantification, γ-Glu-Abu concentration was found to be 10.6 mM.

These results revealed that GSH1 of yeast recognized Abu as a substrate.

Example 9: Effect of Addition of Abu to *Saccharomyces* Cervisiae GSH1 Expression-Enhanced Strain Since it was revealed by the investigation performed in Example 8 mentioned above based on in vitro enzymatic reaction that GSH1 was responsible for an enzymatic reaction using Abu and Glu as substrates, it was then investigated whether this reaction would actually occur in the yeast cells.

1) Acquisition of Uracil Auxotrophic Strain (Ura3 Mutant)

A uracil auxotrophic strain was obtained by introducing an URA3-neighboring DNA except for the URA3 gene into a *Saccharomyces cervisiae* wild-type strain monoploid (Matα type), and disrupting the URA3 gene, as shown below.

First, a 500-bp upstream region of URA3 was amplified by PCR using the primers of SEQ ID NO: 7 (gataaggaga atccatacaa) and SEQ ID NO: 8 (gtgagtttag tatacatgca tttacttata atacagtttt gatttatctt cgtttcctgc), and the chromosomal DNA of the aforementioned wild-type strain as the template. Furthermore, a 500-bp downstream region of URA3 was also amplified using the primers of SEQ ID NO: 9 (aaaactgtat tataagtaaa) and SEQ ID NO: 10 (cacttatttg cgatacagaa). As for PCR conditions, a cycle consisting of thermal denaturation at 94° C. for 10 seconds, annealing at 55° C. for 10 seconds, and extension at 72° C. for 1 minute was repeated 25 times. Then, overlap PCR was performed by using the above two kinds of DNA fragments purified by ethanol precipitation as templates and the primers of SEQ ID NO: 11 (gataaggaga atccatacaa) and SEQ ID NO: 12 (cacttatttg cgatacagaa) to obtain a 1-kb DNA fragment consisting of the 500-bp upstream region and 500-bp downstream region of the URA3 gene ligated together. The wild-type strain was transformed with this DNA fragment, and then cultured overnight in the SD medium to which uracil was added, and the cells were applied to 5-FOA plate medium. The ura3Δ0 strain was obtained from the resulting transformants. This strain was given a private number AJ14956, and was deposited at the independent administrative agency, Agency of Industrial Science and Technology, International Patent Organism Depository (Tukuba Central 6, 1-1, Higashi 1-chome, Tsukuba-shi, Ibaraki-ken, 305-8566, Japan) on Aug. 18, 2010, and assigned an accession number of FERM P-22000. Then, the deposit was converted to an international deposit under the provisions of the Budapest Treaty, and assigned an accession number of FERM BP-11299.

2) Preparation of Template Plasmid for Promoter Substitution

First, the URA3 locus was amplified by PCR using primers of SEQ ID NO: 13 (atgcatgct cataaaattg ataaggaga) and SEQ ID NO: 14 (atagaattca ggacgtcatt agtggcgaa) and the chromosomal DNA of a Saccharomyces cerevisiae wild-type strain as the template (thermal denaturation: 94° C. for 10 seconds, annealing: 50° C. for 10 seconds, extension: 72° C. for 1 minute, 25 cycles). The resulting DNA fragment was purified by ethanol precipitation, and then digested with SphI and EcoRI, and the product was inserted into the plasmid pUC19 at the SphI-EcoRI sites to obtain pUC19-URA3. Then, the ADH1 promoter region was amplified from the chromosomal DNA of the Saccharomyces cerevisiae wild-type strain using the primers of SEQ ID NO: 15 (atactgcaga taatcgatta attttttttt cttc) and SEQ ID NO: 16 (atactgcaga agtagataat tacttcctt). This DNA fragment was digested with PstI, and inserted into pUC19-URA3 digested with PstI and treated with CIAP at the PstI site to obtain pUC19-ADH1p-URA3. It was confirmed that ADH1p was correctly inserted in the forward direction with respect to the URA3 gene by sequencing the neighboring region thereof. In a similar manner, the ADH1 promoter amplified by using the primers of SEQ ID NO: 17 (atagacgtct aattttttt tctttc) and SEQ ID NO: 18 (atagacgtct gttttatatt tgttgtaaa) was digested with AatII, and inserted into pUC19-ADH1p-URA digested with AatII and treated with CIAP at the AatII site to obtain pUC19-ADH1p-URA3-ADH1p. It was confirmed that ADH1p was correctly inserted in the forward direction with respect to the URA3 gene by sequencing the neighboring region thereof.

3) Introduction of ADH1 Promoter into GSH1 Gene on Chromosome

PCR was performed by using the primer of SEQ ID NO: 19 (TATTGCCCCAGIGTICCCTCAACAACCTTGG-TAGTIGGAGCGCAATTAGCGTATCCT GTACCAT-ACTAATTCTCTTCTGCTCTTAACCCAACTG-CACAGA), which has a GSH1 upstream sequence at the 5' end, the primer of SEQ ID NO: 20 (ATACCTTCATCCCT-TATGTGTTCATTGTACGTCCTAGACTCAAACCACT-GCAAAGGC GTGCCCAAAGCTAAGAGTCCCATTG-TATATGAGATAGTTGATT), which has a part of a sequence in ORF starting from the start codon of the GSH1 gene, and pUC19-ADH1p-URA3-ADH1p as the template (thermal denaturation: 94° C. for 10 seconds, annealing: 60° C. for 10 seconds, extension: 72° C. for 4 minutes) to prepare a DNA fragment having URA3 between ADHlp promoters. The ura3Δ0 strain was transformed with this DNA fragment, and plated on an SD plate medium to obtain transformants, and a strain in which the GSH1 promoter was replaced with the ADH1 promoter-URA3-ADH1 promoter was obtained from the transformants.

4) Elimination of URA3 Selective Marker and Substitution of Promoter for GSH1 Gene The strain in which the ADHlp promoter-URA3-ADH1 substitutes for the GSH1 promoter was cultured overnight in a uracil-supplemented SD medium, and an appropriate volume of the culture was applied to 5-FOA plate medium. From the grown colonies, a strain in which URA3 was removed, and the GSH1 promoter was replaced with the ADH1 promoter by homologous recombination between the introduced ADH1 promoters, AG1-ura3Δ0 strain, was obtained. Furthermore, by introducing a DNA amplified by using a wild-type genome as the template and the primers of SEQ ID NO: 21 (AGTTACAGCAATGAAAGAGCA-GAGCGAGAG) and SEQ ID NO: 22 (ATTACTGCTGCT-GTTCCAGCCCATATCCAA) into the above strain, a strain in which URA3 was returned to wild-type, and the GSH1 promoter was replaced with the ADH1 promoter, was obtained. This strain was designated AG1 strain. In a similar manner, by introducing a DNA amplified by using a wild-type genome as the template and the primers of SEQ ID NO: 23 (AGTTACAGCAATGAAAGAGCAGAGCGAGAG) and SEQ ID NO: 24 (ATTACTGCTGCTGTTCCAGC-CCATATCCAA) into the ura3Δ0 strain, AJ14956, a strain in which URA3 was returned to wild-type was obtained. This strain was designated Control strain.

5) Effect of Addition of Abu to Control Strain and AG1 Strain

Then, one loop each of the Control strain and the AG1 strain was inoculated into the SD medium (50 ml in a 500 ml-volume Sakaguchi flask), and cultivated at 30° C. for 24 hours with shaking at a velocity of 120 rpm. Absorbance of the obtained culture broth was measured, the culture broth was inoculated into the SD medium containing Abu at various concentrations (50 ml in a 500 ml-volume Sakaguchi flask) so that OD660 was 0.01 at the start of the culture, and the yeast cells were cultivated at 30° C. for 19 hours with shaking at a velocity of 120 rpm. Cells corresponding to 20 OD units were obtained from the resulting culture broth by centrifugation. Thereafter, an extract was obtained, and intracellular contents of the compounds were measured in the same manner as that of Example 3

As a result, as shown in the following tables, in the AG1 strain, the γ-Glu-Abu content markedly increased compared with the Control strain. On the basis of this result, it was revealed that GSH1 recognized Abu as a substrate also in the cells and produced γ-Glu-Abu from Abu. In addition, when the AG1 strain was cultivated in the SD medium not containing Abu, intracellular γ-Glu-Abu content was lower than the detection limit, and therefore it was also found that the intracellular γ-Glu-Abu content was not necessarily increased only by the enhancement of expression of GSH1, and supply of Abu was important.

TABLE 11

Effect of addition of Abu for Control strain

| | Abu (ppm) | γ-Glu-Abu (ppm) | γ-Glu-Abu-Gly (ppm) |
|---|---|---|---|
| SD medium | 33 | 32 | 5 |
| Medium containing Abu (10 ppm) | 119 | 83 | 51 |
| Medium containing Abu (50 ppm) | 636 | 556 | 240 |

TABLE 11-continued

Effect of addition of Abu for Control strain

|  | Abu (ppm) | γ-Glu-Abu (ppm) | γ-Glu-Abu-Gly (ppm) |
|---|---|---|---|
| Medium containing Abu (100 ppm) | 2442 | 1243 | 488 |

TABLE 12

Effect of addition of Abu for AG1 strain

|  | Abu (ppm) | γ-Glu-Abu (ppm) | γ-Glu-Abu-Gly (ppm) |
|---|---|---|---|
| SD medium | 21 | ND | ND |
| Medium containing Abu (10 ppm) | 110 | 3540 | 684 |
| Medium containing Abu (50 ppm) | 250 | 16012 | 1233 |
| Medium containing Abu (100 ppm) | 353 | 23380 | 1427 |

Example 10: Effect of Addition of Abu to GSH1 Expression-Enhanced Strain of Candida utilis Effect of addition of Abu to a GSH1 expression-enhanced strain of Candida utilis can also be confirmed in the same manner as that of Example 7. Specifically, by using Candida utilis NERC 0988 as a parent strain and the known Cre-loxP system, an uracil auxotrophic CUD4F strain in which the URA3 gene on the chromosome is deleted can be obtained (Shigeru Ikushima et al., 2009, Biosci. Biotechnolo. Biochem., 73(4), 879-884). Since information on the gene sequences required for the genetic manipulation is described in WO95/32289, the paper of U. Gueldener et al. (Nucleic Acids Research, 2002, Vol. 30, No. 6, e23), the paper of Gritz L. and Davis J. (Gene, 25, 179-188 (1983)), and so forth, various tools may be prepared on the basis of such sequence information.

A plasmid for expression of GSH1 of Candida utilis can be constructed by a known method as follows. The known plasmid pRI177 (Ryo Iwakiri et al., 2005, Yeast, 22, 1079-1087) can be digested with the restriction enzyme BamHI and purified in a conventional manner to obtain a linear plasmid. In addition, the method for preparing the plasmid YRpGAP, which is equivalent to the plasmid pR177, is also disclosed in Japanese Patent Laid-open (Kokai) No. 2006-75122.

Figure 3:
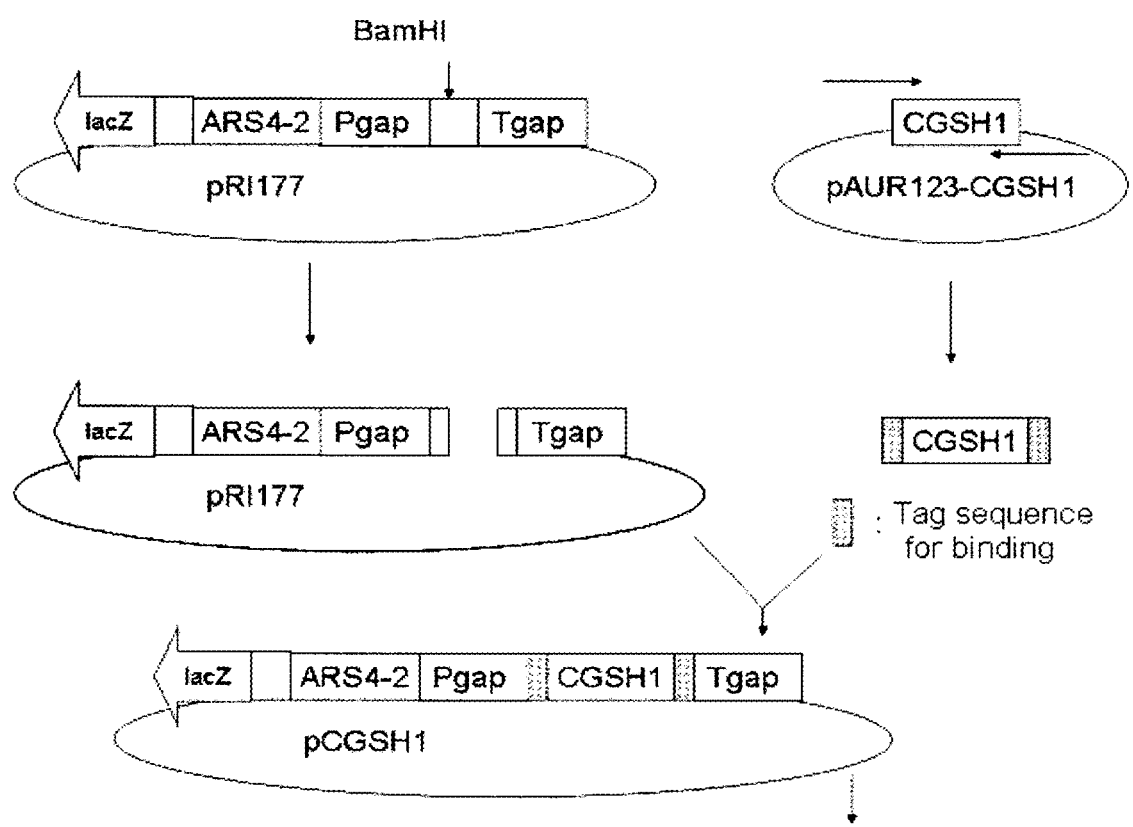
FIG. 3 shows the construction procedure of the plasmid pCGSH1 containing the GSH1 region of *Candida utilis*.

Further, the ORF region of GSH1 is amplified by PCR using the plasmid pAUR-GSH1 containing the sequence of GSH1 of Candida utilis, which was constructed in Example 9, as the template, as well as Primer S (SEQ ID NO: 25, GCAGCCCGGGGGATCATGG-GGCTGCTATCATT-AGG, 15 nucleotides of the 5' end is a sequence homologous to the terminal sequence of the linear plasmid obtained by digestion with the restriction enzyme BamHI) and Primer T (SEQ ID NO: 26, TAGAACTAGTGGATCTTAA-GC-CCTTTGGGTTGTTTATC, 15 nucleotides of the 5' end is a sequence homologous to the terminal sequence of the linear plasmid obtained by digestion with the restriction enzyme BamHI). For this PCR, sequences homologous to the terminal sequences produced by digestion of pR177 with the restriction enzyme BamHI are added to the terminuses of Primers S and T. The PCR product can be purified in a conventional manner, and the purified PCR product and the linear plasmid can be ligated by using In-Fusion Advantage PCR Cloning Kit (Takara Bio). By choosing a plasmid having the objective sequence, autonomously replicable plasmid pCGSH1 containing the GSH1 region of Candida utilis can be constructed. The construction procedure of pCGSH1 is shown in FIG. 3.

Figure 4:
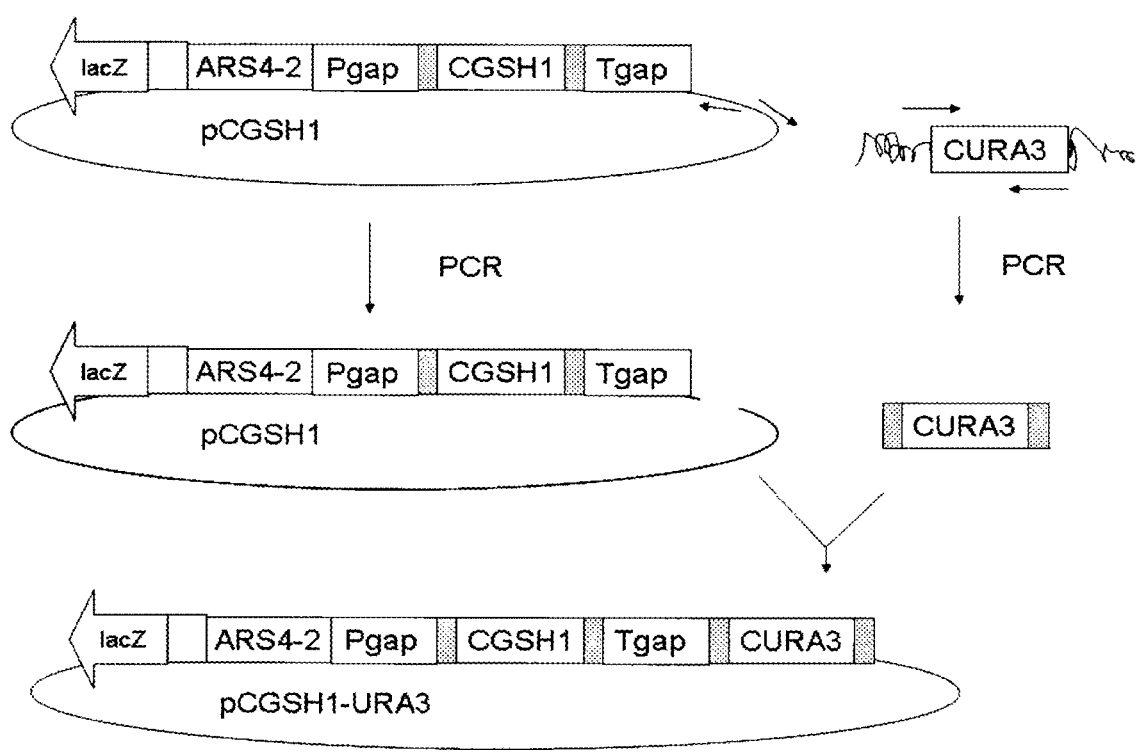
FIG. 4 shows the construction procedure of the vector pCGSH1-URA3 for expression of GSH1 having the URA3 gene.

Further, the URA3 gene as the selection marker can also be introduced into pCGSH1 mentioned above by using In-Fusion Advantage PCR Cloning Kit. Specifically, the full length of pCGSH1 is amplified by PCR using Primer U (SEQ ID NO: 27, TTACGCCAAGCGCGCAATTA) and Primer V (SEQ ID NO: 28, TCATGGTCATAGCT-GTTTCC) according to the protocol described in the attached manual. For this PCR, predetermined regions of the primers can be designed according to the protocol described in the attached manual, and a linear plasmid blunt-ended at a desired position can be prepared by using them. The URA3 gene to be introduced can be amplified by PCR using Primer W (SEQ ID NO: 29, GCGCGCTTGGCG-TAACAAATAGCTCTCTACTTGCT, 15 nucleotides of the 5' end constitute a sequence homologous to the terminal sequence of the linear plasmid), and Primer X (SEQ ID NO: 30, CAGCTATGACCATGAGCAATCTACAACTTC-GAAA, 15 nucleotides of the 5' end constitute a sequence homologous to the terminal sequence of the linear plasmid), which can be designed on the basis of the known sequence information (Luis Rodriguez et al., 1998, Yeast, 14, 1399-1406), as well as the genome of the NBRC 0988 strain as the template. In this PCR, by adding terminal sequence of the linear plasmid to the terminuses of the primers, the gene can be ligated with the plasmid by using In-Fusion Advantage PCR Cloning Kit. As described above, an autonomously replicable vector pCGSH1-URA3 for expression of GSH1 containing the URA3 gene as the selection marker can be constructed. Outline of the construction procedures of pCGSH1-URA3 is shown in FIG. 4.

Then, pCGSH1-URA3 is introduced into the CUD4F strain by the known electroporation method for Candida utilis (Shigeru Ikushima et al., 2009, Biosci. Biotechnolo. Biochem., 73(4), 879-884). By spreading the obtained transformants on the SD medium and selecting a transformant having the objective plasmid from the grown strains, a GSH1 expression-enhanced strain can be obtained. If this GSH1 expression-enhanced strain is cultivated in the SDP medium containing Abu in the same manner as that of Example 7, γ-Glu-Abu is accumulated in the cells.

Example 11: Analysis of Substrate Specificity of Yeast GSH2

Since it was found that a part of accumulated γ-Glu-Abu is metabolized into γ-Glu-Abu-Gly by a certain enzymatic reaction using γ-Glu-Abu as a substrate in yeast cells on the basis of the results of Examples 3, 4, and 5, possibility of side reaction of glutathione synthetase was investigated.
1) Construction of Plasmid pET-GSH2 for Expression of Glutathione Synthetase Gene (GSH2) Derived from Yeast An expression plasmid pET-GSH2 for the GSH2 gene coding for glutathione synthetase of the Saccharomyces cervisiae S288C strain was constructed by the following procedures, and introduced into Escherichia coli.
(1-1) Construction of Plasmid pAUR-GSH2 for Expression of Yeast GSH2

First, an expression plasmid pAUR-GSH2 for yeast was constructed by the following procedure. The construction was entrusted to Takara Bio.

By PCR using Primer A (SEQ ID NO: 33) and Primer B (SEQ ID NO: 34), which were produced on the basis of the nucleotide sequence (SEQ ID NO: 31) of the GSH2 gene of the *Saccharomyces cervisiae* S288C strain, as well as the chromosomal DNA of the S288C strain as the template, the sequence containing the GSH2 gene was amplified. Primer A consisted of a region containing the start codon of the GSH2 gene in the chromosomal DNA of the S288C strain, to which the KpnI recognition sequence and a partial sequence of the yeast expression plasmid pAUR123 (Takara Bio) were added at the 5' end. Primer B consisted of a nucleotide sequence complementary to the C-terminal nucleotide sequence of the GSH2 gene, to which a nucleotide sequence complementary to the sequence coding for the His-tag, a nucleotide sequence complementary to the stop codon (TAA), the XbaI recognition sequence, and a partial sequence of pAUR123 were added. PCR was performed by using PrimeSTAR Max DNA Polymerase (Takara Bio) according to the protocol described in the attached manual. The amplified fragment was introduced into the expression plasmid pAUR123 for yeast (Takara Bio) at the KpnI-XbaI site by using In-Fusion Advantage PCR Cloning Kit (Takara Bio) to construct the expression plasmid pAUR-GSH2 for expression of GSH2 in yeast.

(1-2) Construction of Plasmid pET-GSH2 for Expression of GSH2 in *Escherichia coli*

Then, a GSH2 expression plasmid pET-GSH2 for *Escherichia coli* was constructed by the following procedure.

Primer C (SEQ ID NO: 35) and Primer D (SEQ ID NO: 36) were purchased from Japan Bio Service, which were produced on the basis of on the nucleotide sequence of the GSH2 gene of the *Saccharomyces cervisiae* S288C strain. Primer C consisted of a region containing the start codon of the GSH2 gene in the chromosomal DNA of the *Saccharomyces cervisiae* S288C strain, to which a nucleotide sequence containing the NdeI recognition sequence was added at the 5' end. Primer D consisted of a nucleotide sequence complementary to the nucleotide sequence outside from the stop codon of the GSH2 gene in pAUR-GSH2 mentioned above, to which the XhoI recognition sequence was added at the 5' end.

By PCR using Primer C and Primer D, as well as the aforementioned pAUR-GSH2 as the template, the sequence containing the GSH2 gene was amplified. PCR was performed by preparing 50 μl of a reaction mixture containing the plasmid DNA, 0.2 μmol/L each of the primers, 1.25 units of PrimeSTAR HS DNA Polymerase (Takara Bio), 10 μL of the 5× PrimeSTAR buffer (Takara Bio), and 2.5 mmol/L each of dNTPs (dATP, dGTP, dCTP, and dTTP), and subjecting the reaction mixture to warming at 98° C. for 10 seconds, then 30 cycles of 98° C. for 10 seconds, 56° C. for 5 seconds and 72° C. for 2 minutes, and further warming at 72° C. for 1 minute.

The reaction mixture after PCR (3 μl) was subjected to agarose gel electrophoresis to confirm that a DNA fragment of about 1.5 kb corresponding to the GSH2 gene fragment was amplified, and then the DNA fragment was purified from the remaining reaction mixture by using Ethachinmate (NIPPON GENE), and dissolved in 25 μl of dH$_2$O. Then, the DNA fragment in the whole volume of the obtained DNA solution was digested with the restriction enzymes NdeI and XhoI, then purified by using MinElute Reaction Cleanup Kit (QIAGEN), and dissolved in 15 μl of Buffer EB (10 mM Tris-HCl, pH 8.5, QIAGEN).

The expression plasmid pET-21a(+) (1 μg, Novagen) was digested with the restriction enzymes NdeI and XhoI, then purified by using MinElute Reaction Cleanup Kit, and dissolved in 15 μl of Buffer EB. Then, the DNA fragment in the whole volume of the obtained DNA solution was dephosphorylated with an alkaline phosphatase (calf intestine alkaline phosphatase, CIAP), purified by using MinElute Reaction Cleanup Kit, and dissolved in 10 μl of Buffer EB.

The DNA fragment of about 1.5 kb containing the GSH2 gene obtained above, and the DNA fragment of about 5.4 kb of the expression plasmid pET-21a(+) obtained above were reacted at 16° C. for 30 minutes by using TaKaRa Ligation Kit Ver. 2.1 (Takara Bio), and thereby ligated. Competent cells of the *Escherichia coli* DH5a strain (Takara Bio) were transformed by the heat shock method using the above reaction mixture, and the transformants were applied on the LB [10 g/L of Bacto tryptone (Difco), 5 g/L of yeast extract (Difco), and 5 g/L of sodium chloride (Wako)] agar medium containing 50 μg/ml of ampicillin, and cultured overnight at 37° C.

From the grown colonies of the transformants, a plasmid was extracted by a known method, and the nucleotide sequence thereof was determined by a known method. The obtained plasmid was a plasmid consisting of the GSH2 gene derived from the *Saccharomyces* cervisiae S288C strain having the sequence coding for the His-tag at the 3' end, which was ligated to the T7 promoter on the downstream side, and this plasmid was designated pET-GSH2. The nucleotide sequence of the GSH2 gene derived from the *Saccharomyces cervisiae* S288C strain and the amino acid sequence encoded thereby are shown in SEQ ID NOS: 31 and 32, respectively.

Then, competent cells of the *Escherichia coli* BL21(DE3) strain (Novagen) were transformed with pET-GSH2 by the heat shock method, and the transformants were applied on the LB agar medium containing 50 μg/ml of ampicillin, and cultured overnight at 37° C. Plasmids were extracted from grown colonies of the transformants in a known manner, and the structures thereof were analyzed by using restriction enzymes to confirm that the transformants harbored pET-GSH2. The *Escherichia coli* BL21(DE3) strain harboring pET-GSH2 was designated *Escherichia coli* BL21(DE3)/pET-GSH2.

2) Purification of C-Terminus his-Tag-Added Recombinant Gsh2

*Escherichia coli* BL21(DE3)/pET-GSH2 obtained as described above was inoculated into 3 mL of the LB medium containing 100 μg/ml of ampicillin in a test tube, and cultured at 37° C. for 16 hours with shaking. The obtained culture broth (2 ml) was inoculated into 100 ml of the LB medium contained in a test tube. Culture was performed at 37° C. for 2 hours with shaking, then isopropyl-β-D-thiogalactopyranoside (IPTG) was added at a final concentration of 0.5 mmol/L, and culture was further continued at 30° C. for 4 hours. The culture broth was centrifuged to obtain wet cells.

The wet cells were suspended in 10 ml of a 100 mmol/L Tris-hydrochloric acid buffer (pH 8.0) containing 300 mM sodium chloride, the cells were disrupted by ultrasonication, and the suspension was centrifuged. From the obtained supernatant, His-tag-added recombinant Gsh2 was purified by using a His-tag-added protein purification kit, Ni Sepharose 6 Fast Flow (GE Healthcare), according to the protocol described in the attached manual, and then desalted by using PD-10 column (GE Healthcare) according to the protocol described in the attached manual. Then, this sample was concentrated by using a centrifugal filtration membrane of 10 kDa cutoff (Amicon Ultra-0.5 mL 10K (catalog number, UFC501096), MILLIPORE) according to the protocol described in the attached manual. This purified, desalted and concentrated Gsh2 was used for the following experiments as purified Gsh2.

3) Production of γ-Glu-Abu-Gly Using Purified Gsh2

By using the purified Gsh2 obtained above, possibility of production of γ-Glu-Abu-Gly using γ-Glu-Abu as the substrate was examined. A reaction mixture having the following composition was prepared, and the enzymatic reaction was performed at 30° C. for 22 hours.

| [Composition of reaction mixture] | |
| --- | --- |
| Purified Gsh2 | 300 μg/500 μl |
| Tris-HCl (pH 8.0) | 100 mmol/L |
| γ-Glu-Abu | 10 mmol/L |
| Glycine | 10 mmol/L |
| Adenosine triphosphate (ATP) | 10 mmol/L |
| MgCl$_2$ | 10 mmol/L |
| Dithiothreitol (DTT) | 0.1 mmol/L |

After completion of the reaction, the reaction product was analyzed by HPLC under the same conditions as those used in Example 8. As a result, the retention time of the peak of the reaction product agreed with that of a γ-Glu-Abu-Gly sample, and it was judged that the product was γ-Glu-Abu-Gly. As a result of quantification, γ-Glu-Abu-Gly concentration was found to be about 10 mM.

Example 12: Effect of Addition of Abu to GSH2-Disrupted Strain

The results of Example 11 revealed that γ-Glu-Abu served a substrate of glutathione synthetase of yeast to generate γ-Glu-Abu-Gly. On the other hand, the results of Examples 4 and 5 revealed that a part of intracellularly incorporated γ-Glu-Abu was converted into γ-Glu-Abu-Gly, but γ-Glu-Abu was also accumulated. On the basis of these results, it was considered that all of γ-Glu-Abu accumulated in the cells could not be metabolized into γ-Glu-Abu-Gly with the GSH2 activity of the yeast wild strain, but a lower activity thereof might provide larger accumulation of γ-Glu-Abu. Therefore, effect of addition of Abu to a GSH2-disrupted strain was investigated.

Specifically, Saccharomyces cervisiae S288C gsh2Δ0 strain was obtained by the following procedure. First, a region containing GSH2 including replacement with the kanamycin resistance gene cassette KanMX was amplified by using the primers of SEQ ID NO: 37 (CTAGTGAAAAACAAGAAGTA) and SEQ ID NO: 38 (GCCACATAGAAAAATCGATG) as well as the genome of GSH2-disrupted strain of YEAST KNOCK OUT STRAIN COLLECTION (Funakoshi, YCS1056) as the template. As for PCR conditions, a cycle consisting of thermal denaturation at 94° C. for 10 seconds, annealing at 55° C. for 10 seconds, and extension at 72° C. for 3 minutes was repeated 25 times. Then, the DNA fragment was purified by ethanol precipitation, and then used to transform the S288C strain, and the cells were applied to a YPD plate medium containing G418. From the obtained transformants, the gsh2Δ0 strain was obtained.

Then, effect of addition of Abu to this strain was investigated in the same manner as that used in Example 3. First, one loop of the gsh2Δ0 strain was inoculated into the SD medium (50 ml in 500 ml-volume Sakaguchi flask), and cultured at 30° C. for 48 hours with shaking at a velocity of 120 rpm. Absorbance of the obtained culture broth was measured, the culture broth was inoculated into the SD medium or the SD medium containing 100 ppm of Abu as a final concentration (400 ml in a 2 L-volume conical flask with baffle fins), so that OD660 was 0.01 at the start of the culture (absorbance was measured by using DU640 SPECTROPHTOMETER, BECKMAN COULTER), and culture was performed at 30° C. for 65.75 hours with shaking by rotation at a velocity of 120 rpm. From the obtained culture broth, an extract was obtained, and intracellular content of γ-Glu-Abu was measured in the same manner as that of Example 3.

As a result, when the strain was cultured in the SD medium, the intracellular γ-Glu-Abu content was 128 ppm, but when it was cultured in the medium containing 100 ppm of Abu, the intracellular γ-Glu-Abu content was 10333 ppm. Thus, this result also revealed that γ-Glu-Abu was not accumulated only by deficiency of the GSH2 gene, but supply of Abu was important.

Example 13: Effect of Addition of Abu to GSH2-Disrupted Strain (2)

By using a procedure using the cre-loxp system similar to that used for disruption of URA3 of Candida utilis in Example 10 with changing a part of the primer sequences, a GSH2-disrupted Candida utilis CUDF4 strain can be obtained.

Specifically, by using Primer N-59 (SEQ ID NO: 39, AAGTAGCCAATACAACCAGC, sequence of from the −57th to −38th region upstream of ORF of GSH2 of Candida utilis), Primer N60 (SEQ ID NO: 40, CTGCAGCGTACGAAGCTTCAGCTGGCGGGCCACTCACC-CACTCAACATCAC, 31 nucleotide from the 5' end constitute a direct repeat for overlap PCR), Primer N-295 (SEQ ID NO: 41, GCTGTTTTAGACTCGTTTGC, a region of the 244th to 263rd positions of ORF of GSH2 of Candida utilis), Primer N-296 (SEQ ID NO: 42, CTGCAGCGTACGAAGCTTCAGCTGGCGGCCAGAAGATTCAGACAC-CGGGA, 29 nucleotides from the 5' end constitute a direct repeat for overlap PCR), Primer N-61 (SEQ ID NO: 43, ATTAGGTGATATCAGATCCACTAGTGGCCTG-GTTTCTTAAGATCTATTCC, 30 nucleotides from the 5' end constitute a direct repeat for overlap PCR), and Primer N-62 (SEQ ID NO: 44, TAAATGCGGCTCCATCTATTG, region up to the nucleotide of the +18th position downstream of ORF of GSH2 of Candida utilis) instead of the primers IM-59, IM60, IM295, IM296, IM61, and IM-62 used for obtaining the CUDF4 strain described in Shigehito IKUSHIMA et al., Biosci. Biotechnol. Biochem., 73 (4), 879-884, 2009, respectively, a cassette for disruption of GSH2 of Candida utilis can be prepared. By using this cassette for disruption in the same manner as that described in the reference, GSH2 of the CUDF4 strain is disrupted. In addition, if 1 mM GSH and a required amount of uracil are added to the medium in the transformation step and the culture step, the acquisition rate of the strain may be improved. Whether a strain obtained as described above is the objective GSH2-disrupted strain can be confirmed by PCR. Further, by transforming such a GSH2-disrupted strain with pCGSH1-URA3 in the same manner as that of Example 10, a strain of which expression of GSH1 is enhanced, and GSH2 is disrupted can be obtained. If this strain is cultured in a medium containing Abu, a marked amount of γ-Glu-Abu is accumulated in the cells.

Example 14: Search of Intracellular Abu Synthesis Enzyme

Although the metabolic pathways of *Saccharomyces cerevisiae* have been well studied, any enzyme that biosynthesizes Abu is not known. However, the inventors of the present invention estimated that an enzyme reported as aminotransferase for another substrate might have the activity for converting AKB (α-ketobutyrate (α-ketobutyric acid)) into Abu, in view of the fact that substrate recognition of aminotransferases was comparatively ambiguous, which had been confirmed in researches using other microorganisms. Therefore, there were bred a strain highly expressing BAT1, reported to be responsible for the transamination reaction of BCAA (branched chain amino acid), and a strain highly expressing UGA1, reported to be responsible for the transamination reaction of GABA (γ-aminobutyric acid).

1) Construction of BAT1 and UGA1 Expression Vectors

First, in a conventional manner, a constitutive expression promoter of yeast, ADH1p, was introduced into the plasmid pYES2 (Invitrogen), which is a yeast-*Escherichia coli* shuttle vector. Specifically, by PCR using the genome prepared from a yeast wild strain as the template, as well as primers of SEQ ID NO: 45 (ATAACCGGTGGGTGTA-CAATATGGACTTC) and SEQ ID NO: 46 (ATAAAGCTTTGTATATGAGATAGTTGATT), the promoter region of ADH1 was amplified (a cycle consisting of thermal denaturation at 94° C. for 10 seconds, annealing at 50° C. for 10 seconds, and extension at 72° C. for 1 minute was repeated 25 times). The obtained DNA fragment was purified by ethanol precipitation, then digested with the restriction enzymes HindIII and AgeI, and inserted into the plasmid pYES2 at the HindIII-AgeI site to obtain pYES2-ADH1p.

Then, in order to insert ORF regions of the genes into this pYES2-ADH1p, amplification products of the genes were each subcloned into the pT7 vector. Specifically, by PCR using the genome prepared from a *Saccharomyces* cervisiae wild strain as the template, as well as the primers of SEQ ID NO: 47 (GGATCCATGTTGCAGAGACATTCC) and SEQ ID NO: 48 (TCTAGATTAGTTCAAGTCGGC), or the primers of SEQ ID NO: 49 (AAGCTTACAGA-CAAGAAACCGTC) and SEQ ID NO: 50 (TCTAGAGGC-CTCGCTAATATAC), the ORF regions of BAT1 and UGA1 were amplified, respectively. The obtained BAT1 amplification product was digested with the restriction enzymes BamHI and XbaI, and inserted into the pT7 vector at the BamHI-XbaI site to obtain pT7-BAT1. The UGA1 amplification product was digested with the restriction enzymes HindIII and XbaI, and inserted into the pT7 vector at the HindIII-XbaI site to obtain pT7-UGA1.

pT7-BAT1 obtained as described above was treated with the restriction enzymes BamHI and XbaI, and the DNA fragment of BAT1 was purified by separation based on electrophoresis and excision of the objective gene, and introduced into the plasmid pYES2-ADH1p at the BamHI-XbaI site. Further, pT7-UGA1 was treated with the restriction enzymes HindIII and XbaI, and the DNA fragment of UGA1 was purified by separation based on electrophoresis and excision of the objective gene, and introduced into the plasmid pYES2-ADH1p at the HindIII-XbaI site. As described above, a BAT1 high expression vector, pYES2-ADH1p-BAT1, and a UGA1 high expression vector, pYES2-ADH1p-UGA1, were prepared.

The nucleotide sequences of BAT1 and UGA1 are shown in SEQ ID NOS: 51 and 53, respectively. Further, the amino acid sequences encoded by these genes are shown in SEQ ID NOS: 52 and 54, respectively.

2) Breeding of S288Cura3Δ0 Strain

In the same manner as that of Example 9, there was bred S288Cura3Δ0 strain corresponding to the S288C strain in which the ORF region of the URA3 gene was deleted.

3) Breeding of Various Expression Strains

By transforming S288Cura3Δ0 bred in 2) with each of the expression vectors constructed in 1), strains highly expressing each of the genes were bred. Specifically, competent cells of S288Cura3Δ0 were prepared by using Frozen EZ Yeast Transformation II Kit of Zymo Research, and each of the expression vectors was introduced into the cells to obtain S288C/pYES2-ADH1p strain, S288C/pYES2-ADH1p-BAT1 strain, and S288C/pYES2-ADH1p-UGA1 strain.

4) Evaluation of Obtained Strains

The aforementioned strains were evaluated by culture in the SD medium in the same manner as that of Example 3. The results are shown in Table 13.

TABLE 13

| | Abu content | γ-Glu-Abu content | γ-Glu-Abu-Gly content |
|---|---|---|---|
| Control | 23 ppm | 114 ppm | 181 ppm |
| BAT1 high expression strain | 37 ppm | 197 ppm | 602 ppm |
| UGA1 high expression strain | 41 ppm | 116 ppm | 310 ppm |

As a result, increase of the intracellular Abu content was observed in the BAT1 high expression strain and the UGA1 high expression strain. Further, since Abu synthesized within the cells is used as a substrate for γ-Glu-Abu and γ-Glu-Abu-Gly, the total amounts of these three kinds of compounds were compared in terms of molar concentration. The total amounts were calculated to be 2.46 μmol/g-DCW for the control strain, 7.06 μmol/g-DCW for the BAT1 high expression strain, and 3.91 μmol/g-DCW for the UGA1 high expression strain, and thus it was revealed that the high expression of the various aminotransferases provided increase of amount of intracellular Abu-containing compounds, i.e., increase of Abu biosynthesis ability. Further, in the same manner as that used for obtaining the S288Cgsh2Δ0 strain from the S288Cura3Δ0 strain as a parent strain in Example 12, S288Cura3Δ0gsh2Δ0 strain was obtained. By preparing competent cells of this strain and introducing each of the expression vectors into the cells, S288Cgsh2Δ0/pYES2-ADH1p strain and S288Cgsh2Δ0/pYES2-ADH1p-BAT1 strain were obtained. If the latter strain is cultured in the SD medium, it accumulates γ-Glu-Abu.

Example 15: Effect of High Expression of GSH1 and High Expression of Aminotransferase Since the effect of increasing the intracellular Abu-containing compounds was provided by increase of the activity of aminotransferase, especially increase of the activity of BAT1, in the aforementioned investigation, effect of combination thereof with high expression of GSH1 was examined. The uracil auxotrophic strain obtained in Example 9, AG1-ura3Δ0, was transformed with pYES2-ADH1p-BAT1 prepared in Example 14 to breed a BAT1 and GSH1 high expression strain, AG1/pYES2-ADH1p-BAT1 strain. In the same manner as that of Example 3, this strain was cultured in the SD medium, and the γ-Glu-Abu content in the cells and the γ-Glu-Abu content in solid content of extract were calculated. As a result, the AG1/pYES2-ADH1p-BAT1 strain contained 1813 ppm of γ-Glu-Abu based on the dry cell weight, and the extract obtained from the cells of the strain contained about 4560 ppm of γ-Glu-Abu based on solid content.

Example 16: Yeast Extract Added with Abu and Treated with γ-glutamyltransferase A 1% aqueous solution of yeast extract containing regent GSH (Wako Pure Chemical Industries) having a GSH content of about 8% based on the solid content was prepared, and adjusted to pH 7.0 with NaOH. Powder Abu was added to this solution at a final concentration of 800 ppm, 1600 ppm, or 8000 ppm in the aqueous solution to prepare test samples. Further, the yeast extract aqueous solution not containing Abu was used as a control. γ-GTP (γ-glutamyl-transpeptidase from equine kidney; Sigma; code, G9270-100UN) was added to these test samples at 0.05 mg/ml, and the enzymatic reaction was allowed at 37° C. for 120 minutes. The reaction mixture was immediately cooled on ice after the reaction, and the γ-Glu-Abu content was measured. Further, the solid content was measured by using a part of the reaction mixture, and the content of γ-Glu-Abu produced by the enzymatic reaction based on the solid content was calculated.

Figure 5:
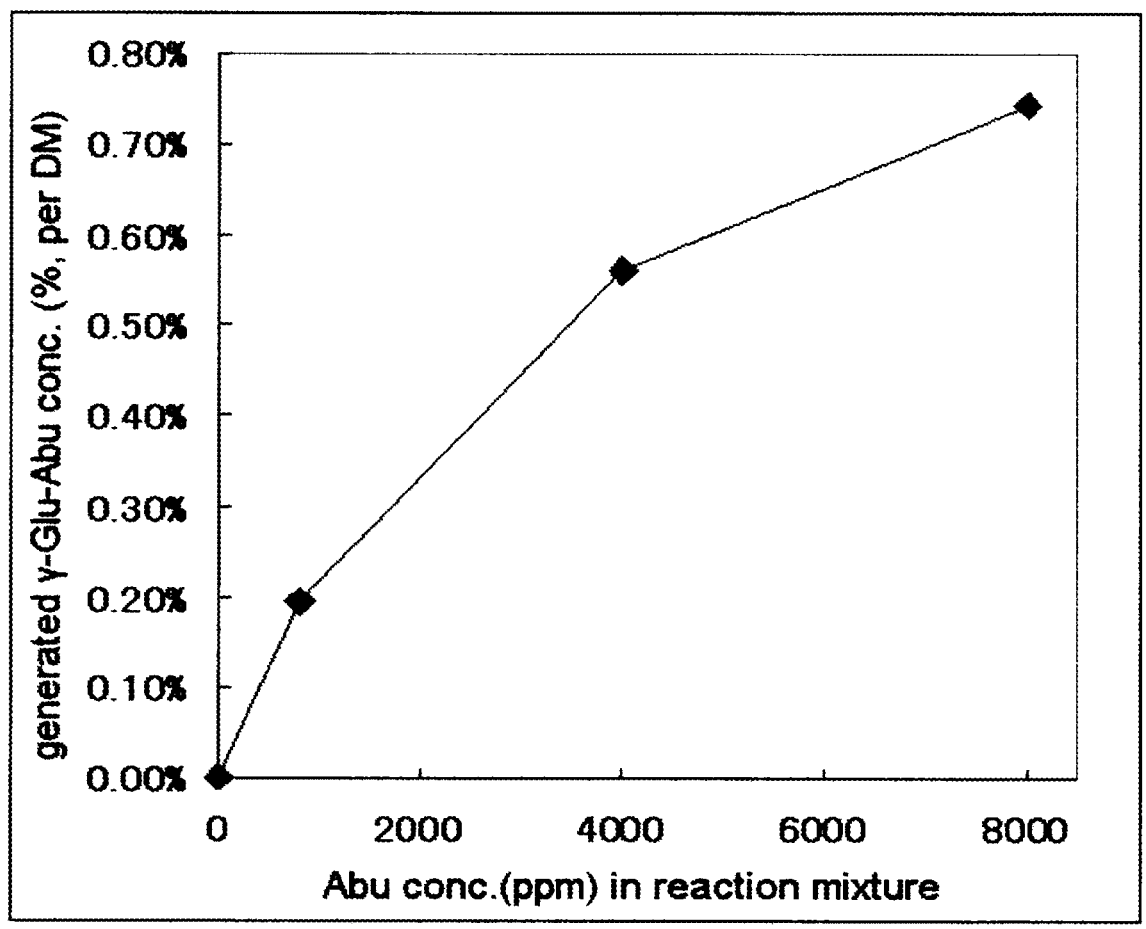
FIG. 5 shows the relation between added Abu concentration and γ-Glu-Abu production amount in the yeast extract on which γ-glutamyltransferase was made to act.

As a result, as shown in FIG. 5, γ-Glu-Abu was hardly produced in the no Abu addition experiment, but more γ-Glu-Abu was produced as the addition amount of Abu was increased.

Example 17: Organoleptic Evaluation of Yeast Extract Containing γ-Glu-Abu (1)

First, samples for organoleptic evaluation were prepared by the following procedure. In the same manner as that used in Example 4, one loop of the S288C strain was inoculated into the SD medium (50 ml in 500 ml-volume Sakaguchi flask), and cultivated at 30° C. for 24 hours with shaking at a velocity of 120 rpm. Absorbance of the obtained culture broth was measured, the culture broth was inoculated into the SD medium (400 ml in 2 L-volume conical flask with baffle fins, 4 flasks) or the SD medium containing 200 ppm of γ-Glu-Abu as a final concentration (400 ml in 2 L-volume conical flask with baffle fins, 4 flasks), so that OD660 was 0.01 at the start of the culture (absorbance was measured by using DU640 SPECTROPHTOMETER, BECKMAN COULTER), and the yeast cells were cultivated at 30° C. for 19 hours with shaking by rotation at a velocity of 120 rpm. In the same manner as that used in Example 4, an extract was obtained from the obtained cells, and the γ-Glu-Abu concentration in the extract, and the solid content of the extract were obtained. As a result, the γ-Glu-Abu concentration in the extract prepared in the γ-Glu-Abu addition experiment was about 1,000 ppm, and the solid content thereof was about 0.59% (Extract 1). On the other hand, the solid content of the extract prepared in the no addition experiment was about 1.00% (Extract 2).

Then, kokumi of the following samples was evaluated by six special panelists according to the following method.
Control sample: Aqueous solution containing 0.2% of MSG, and 0.5% of NaCl
Sample 1: Control sample to which Extract 1 is added so that γ-Glu-Abu content is about 40 ppm
Sample 2: Control sample to which Extract 2 is added so that solid content is the same as that of Extract 1 added to Sample 1

As a result, all the panelists evaluated that stronger kokumi of the initial taste was obtained with Sample 1. On the basis of this result, it was confirmed that γ-Glu-Abu exhibited the characteristic thereof, initial taste, even in yeast extract.

Example 18: Organoleptic Evaluation of Yeast Extract Containing γ-Glu-Abu (2)

One loop of the *Saccharomyces cervisiae* AJ14892 strain (Japanese Patent Laid-open (Kokai) No. 2008-61525) that accumulates γ-glutamylcysteine (γ-GC) was inoculated into the SD medium (50 ml in 500 ml-volume Sakaguchi flask, 4 flasks), and cultivated at 30° C. for 48 hours with shaking at a velocity of 120 rpm. Absorbance of the obtained culture broth was measured, the culture broth was inoculated into the SD medium (400 ml in a 2 L-volume conical flask with baffle fins, 4 flasks), so that OD660 was 0.01 at the start of the culture, and the yeast cells were cultivated at 30° C. with shaking by rotation at a velocity of 120 rpm. As for the culture time, residual sugar and absorbance were periodically measured, and the culture was performed for about 42 hours so that the absorbance became about 1.8, which is the absorbance obtained when the S288C strain was cultured in the SD medium for 19 hours. In the same manner as that used in Example 4, an extract was obtained from the cells, and the solid content of the extract were obtained. As a result, the solid content was found to be about 0.71% (Extract 3). The γ-GC content in Extract 3 was about 390 ppm. As described above, Extract 3 having a γ-GC content of about 5.5% based on the solid content was obtained.

Then, kokumi of the following samples was evaluated by six special panelists according to the following method.
Control sample: aqueous solution containing 0.2% of MSG, and 0.5% of NaCl
Sample 3: Control sample to which Extract 3 is added so that solid content is the same as that of Extract 1 added to Sample 1
Sample 4: Control sample to which marketed GSH-rich yeast extract (Aromild UG8, Kohjin Co., Ltd.) was added so that solid content is the same as that of Extract 1 added to Sample 1

For the evaluation, kokumi titer of the control sample was defined as 0.0, and kokumi titer of Sample 4 was defined as 3.0. As a result, as shown in the following table, it was found that the γ-Glu-Abu-containing yeast extract (Sample 1) showed an organoleptic profile different from those obtained with the sample similarly containing a dipeptide, the γ-GC-rich yeast extract (Sample 3), and the sample containing a tripeptide, the GSH-rich yeast extract (Sample 4), and gave a high kokumi titer for the initial taste.

TABLE 14

|  | Kokumi of initial taste | Kokumi of middle-aftertaste |
|---|---|---|
| Control | 0.0 | 0.0 |
| Sample 1 | 4.0 | 1.8 |
| Sample 3 | 1.8 | 2.2 |
| Sample 4 | 3.0 | 3.0 |

Example 19: Effect of Enhancement of α-Ketobutyric Acid-Producing Ability

Then, effect of enhancement of α-ketobutyric acid-producing ability was examined. Although it was not known so far that α-ketobutyric acid might serve as a precursor of Abu within yeast cells, whether enhancement of α-ketobutyric acid-producing ability could increase the Abu-producing ability in yeast cells was examined, since activation of aminotransferase increased the Abu-producing ability in yeast cells.

First, in order to insert the ORF region of CHA1 coding for serine (threonine) deaminase into pYES2-ADHlp prepared in Example 13, an amplification product of CHA1 was subcloned into the pT7 vector. Specifically, by PCR using the genome prepared from a Saccharomyces cervisiae wild strain as the template, and the primers of SEQ ID NO: 55 (ATAAAGCTTAACCAGCGAGATGTCG) and SEQ ID NO: 56 (CTCTCTAGAGGGCAAATTGATGCTTC), the ORF region of CHA1 was amplified. The obtained CHA1 amplification product was digested with the restriction enzymes HindIII and XbaI, and inserted into the pT7 vector at the HindIII-XbaI site to obtain pT7-CHA1.

pT7-CHA1 obtained as described above was treated with the restriction enzymes HindIII and XbaI, and the DNA fragment of CHA1 was purified by separation based on electrophoresis and excision of the objective gene, and introduced into the plasmid pYES2-ADH1p at the HindIII-XbaI site. A CHA1 high expression vector pYES2-ADH1p-CHA1 was prepared as described above.

The nucleotide sequence of CHA1 is shown in SEQ ID NO: 57. Further, the amino acid sequence encoded by this gene is shown in SEQ ID NO: 58.

Then, the promoter region of BAT1 in the uracil auxotrophic strain bred in Example 9, AG1-ura3Δ0, was replaced with the promoter region of PGK1 according to the method of Sofyanovich et al. (Olga A. Sofyanovich et al., A New Method for Repeated "Self-Cloning" Promoter Replacement in Saccharomyces cerevisiae, Mol. Biotechnol., 48, 218-227 (2011)). The DNA fragment for the replacement of the promoter was prepared by amplification based on PCR using the pPUP plasmid described in the reference and the primers for replacement of BAT1, SEQ ID NO: 59 (GCCAGGCG-GTTGATACTTTGTGCAGATTTCATACCGGCTGTCGC-TATTATTACTGAT GAATTGGCTCTCTTTTTGTT-TAATCTTAACCCAACTGCACAGA) and SEQ ID NO: 60 (TTGGATGCATCTAATGGGGCACCAGTAGCGAGT-GTTCTGATGGAGAATTTCCCCAAC TTCAAGGAAT-GTCTCTGCAACATTGTTTTATATTTGTTGTAAA). The GSH1- and BAT1-enhanced strain of the uracil auxotrophic strain constructed as described above, AGB-ura3Δ0 strain, was transformed with the CHA1 high expression vector to breed a strain highly expressing GSH1, BAT1 and CHA1. Specifically, in the same manner as that used in Example 14, competent cells of the AGB-ura3Δ0 strain were prepared by using Frozen EZ Yeast Transformation II Kit of Zymo Research, and pYES2-ADH1p-CHA1 was introduced into the cells to obtain AGB-ura3Δ0/pYES2-ADH1p-CHA1 strain.

The aforementioned strain was evaluated by culture in the SD medium in the same manner as that of Example 14. As a result, this strain contained 2024 ppm of γ-Glu-Abu based on the dry cell weight.

Example 20: Effect of Disruption of Peptidase

Then, effect of disruption of an enzyme gene DUG2, reported to be involved in the decomposition of GSH, was investigated. The nucleotide sequence of DUG2 is shown in SEQ ID NO: 61, and the amino acid sequence encoded by this gene is shown in SEQ ID NO: 62.

First, by using the primer of SEQ ID NO: 63 having 80 nucleotides upstream from the start codon of DUG2 (TTAAGTGAAAAACTATTTCGAGAAACCGAACAAC-CCTGTAAGGAAAAGTGAAAAACG AGGGCAGAAG-TAATTGTGAAATCGTTCATCATCTCATGGATCT), and the primer of SEQ ID NO: 64 having 80 nucleotides downstream from the stop codon of DUG2 (ACTAATTAT-CATTAGGTAGAGGCCTACATATGCAAATTGGG-TATATATTAAGCACTT TAAAATCAATTGTTTGTAGT-TGTAGATTCCCGGGTAATAACTG), the URA3 gene of a wild type strain was amplified. As for PCR conditions, a cycle consisting of thermal denaturation at 94° C. for 10 seconds, annealing at 50° C. for 10 seconds, and extension at 72° C. for 2 minutes was repeated 25 times. The AG1-ura3Δ0 strain was transformed with the obtained DNA fragment, and applied to the SD medium not containing uracil. A dug2Δ strain of the AG1-ura3Δ0 (henceforth referred to as AG1-dug2Δ0 strain) was obtained from the grown transformants. The AG1 strain and the AG1-dug2Δ0 strain were cultured in the SD medium containing 100 ppm of Abu in the same manner as that of Example 9. As a result, it was found that the AG1-dug2Δ0 strain contained a larger amount of γ-Glu-Abu. It was suggested that disruption of the enzyme that decomposed GSH was useful for accumulation of γ-Glu-Abu.

Table 15: Effect of Addition of Abu

TABLE 15

| Effect of addition of Abu | | | |
|---|---|---|---|
| | Abu (ppm) | γ-Glu-Abu (ppm) | γ-Glu-Abu-Gly (ppm) |
| AG1 strain | 998 | 30467 | 1020 |
| AG1-dug2Δ0 strain | 782 | 39989 | 1746 |

INDUSTRIAL APPLICABILITY

According to the present invention, a yeast containing γ-Glu-Abu and a yeast extract containing γ-Glu-Abu can be produced. The yeast extract containing the peptide has a superior effect of imparting kokumi, especially initial taste type kokumi.

The invention claimed is:

1. A method for producing a yeast extract comprising γ-Glu-Abu, comprising:
   culturing yeast cells in a medium comprising at least one of Abu and γ-Glu-Abu to produce cultured cells; and
   preparing a yeast extract from the cultured cells,
   wherein the medium comprises 10 ppm or more of Abu, 1 ppm or more of γ-Glu-Abu, or both and wherein the yeast extract comprises 0.2% or more of γ-Glu-Abu based on a dry weight of the yeast extract.

2. The method according to claim 1, wherein the yeast cells belong to the genus *Saccharomyces* or *Candida*.

3. The method according to claim 1, wherein the yeast cells belong to *Saccharomyces cervisiae* or *Candida utilis*.

4. The method according to claim 1, wherein the yeast cells have an increased activity of a γ-glutamylcysteine synthetase, an attenuated activity of a glutathione synthetase, or both.

5. The method according to claim 1, wherein, in the culturing, the at least one of Abu and γ-Glu-Abu is continuously added to the medium.

6. The method according to claim 1, further comprising:
   preculturing the yeast cells in a medium which is free of Abu and γ-Glu-Abu prior to the culturing.

7. The method according to claim 1, wherein the culturing comprises culturing the yeast cells such that the cultured cells contain γ-Glu-Abu in an amount of 0.04% or more, based on a dry weight of the cultured cells.

8. The method according to claim 1, wherein the culturing comprises culturing the yeast cells such that the cultured cells contain γ-Glu-Abu in an amount of 0.4% or more, based on a dry weight of the cultured cells.

9. The method according to claim 4, wherein the yeast cells further have an attenuated activity of a peptidase capable of decomposing an intracellular peptide.

10. The method according to claim 1, wherein the method consists essentially of the culturing and the preparing.

11. The method according to claim 7, wherein the method consists essentially of the culturing and the preparing.

12. The method according to claim 8, wherein the method consists essentially of the culturing and the preparing.

13. The method according to claim 1, wherein the medium comprises 50 ppm or more of Abu, 10 ppm or more of γ-Glu-Abu, or both.

14. The method according to claim 1, wherein the yeast extract comprises 2.0% or more of γ-Glu-Abu based on a dry weight of the yeast extract.

15. The method according to claim 1, further comprising, prior to the preparing of the yeast extract:
   separating the cultured cells from the medium.

* * * * *

SEQUENCE LISTING

```
<160> NUMBER OF SEQ ID NOS: 64

<210> SEQ ID NO 1
<211> LENGTH: 1995
<212> TYPE: DNA
<213> ORGANISM: Candida utilis
<220> FEATURE:
<221> NAME/KEY: CDS
<222> LOCATION: (1)..(1995)
```

<400> SEQUENCE: 1

```
atg ggg ctg cta tca tta ggg act ccg ctt cct tgg gaa cag aca agg      48
Met Gly Leu Leu Ser Leu Gly Thr Pro Leu Pro Trp Glu Gln Thr Arg
 1               5                  10                  15 gag tac gcg gag cac gtc cgc act gag ggt atc gaa cag ttg atc aag      96
Glu Tyr Ala Glu His Val Arg Thr Glu Gly Ile Glu Gln Leu Ile Lys
             20                  25                  30 atg ttc aag gct gca tat gca aga acc ggt gat ggc tat cta tgg gga     144
Met Phe Lys Ala Ala Tyr Ala Arg Thr Gly Asp Gly Tyr Leu Trp Gly
         35                  40                  45 gac gaa gtg gag tat acc ctg gtc aag ttt gat cat ggt cgt ggt ctt     192
Asp Glu Val Glu Tyr Thr Leu Val Lys Phe Asp His Gly Arg Gly Leu
     50                  55                  60 gct ctg ttg agt atc gat aag gac agc gta ttg gct gat ctc aac gag     240
Ala Leu Leu Ser Ile Asp Lys Asp Ser Val Leu Ala Asp Leu Asn Glu
 65                  70                  75                  80 ggc gga tca ctg gca cag ttg tct gtg gac aat gat ctc aac ttc cac     288
Gly Gly Ser Leu Ala Gln Leu Ser Val Asp Asn Asp Leu Asn Phe His
                 85                  90                  95 ccg gaa tat ggc cgc ttc atg ctg gag gcg aca ccg ctg gct ccg tac     336
Pro Glu Tyr Gly Arg Phe Met Leu Glu Ala Thr Pro Leu Ala Pro Tyr
            100                 105                 110 aac ggt gat tcg ctg gag aac tac ttg tac gtg gag agg aac atg aac     384
Asn Gly Asp Ser Leu Glu Asn Tyr Leu Tyr Val Glu Arg Asn Met Asn
        115                 120                 125 agc aga aga tca gtg gcg cag act gcg att gct gac ggc acc atc aag     432
Ser Arg Arg Ser Val Ala Gln Thr Ala Ile Ala Asp Gly Thr Ile Lys
    130                 135                 140 ccg ttg acc ata acg gtg tac cca ttg atg ggc atc aac acc ttc acc     480
Pro Leu Thr Ile Thr Val Tyr Pro Leu Met Gly Ile Asn Thr Phe Thr
145                 150                 155                 160 ttc cca tca gcg gtg gct aac ggc gag gca tca caa tcg ctg ttc tta     528
Phe Pro Ser Ala Val Ala Asn Gly Glu Ala Ser Gln Ser Leu Phe Leu
                165                 170                 175 ccg gat gag atc atc aac aga cat gcg aga ttc cca aca ttg acg gcc     576
Pro Asp Glu Ile Ile Asn Arg His Ala Arg Phe Pro Thr Leu Thr Ala
            180                 185                 190 aac att cgg aaa cgc cgt ggt gag aag gtg gcc atc aac gta ccg ctc     624
Asn Ile Arg Lys Arg Arg Gly Glu Lys Val Ala Ile Asn Val Pro Leu
        195                 200                 205 tac aag gat aca aat acg tta tcc att gac gag tca att cca aag gga     672
Tyr Lys Asp Thr Asn Thr Leu Ser Ile Asp Glu Ser Ile Pro Lys Gly
    210                 215                 220 cgc tcc ctg ttc aag cac gac gaa gaa cca gag ctc ggt gca gca ctg     720
Arg Ser Leu Phe Lys His Asp Glu Glu Pro Glu Leu Gly Ala Ala Leu
225                 230                 235                 240 cca ggg cat ata tac atg gac tcc atg gga ttc ggt atg gga tgc tca     768
Pro Gly His Ile Tyr Met Asp Ser Met Gly Phe Gly Met Gly Cys Ser
                245                 250                 255 tgt cta caa gta aca gtg caa gca cca aac ttg aac aga gct cgt tac     816
Cys Leu Gln Val Thr Val Gln Ala Pro Asn Leu Asn Arg Ala Arg Tyr
            260                 265                 270 ctc tat gat tca tgg gct aat ttt gca cca ttg ttc cta gca ttg acg     864
Leu Tyr Asp Ser Trp Ala Asn Phe Ala Pro Leu Phe Leu Ala Leu Thr
        275                 280                 285 gca gca gcg cca gtg ttc aaa ggc cac tta gct gac cag gat gtc aga     912
Ala Ala Ala Pro Val Phe Lys Gly His Leu Ala Asp Gln Asp Val Arg
    290                 295                 300
```

-continued

| | | |
|---|---|---|
| tgg aac gtc att tct ggt gct gtt gat gat cgt act gcc tac gag cgt<br>Trp Asn Val Ile Ser Gly Ala Val Asp Asp Arg Thr Ala Tyr Glu Arg<br>305                  310                315                320 | 960 |
| gat gtt aag cct ctg cat agc gat ggc gca ttt ggt gga atg aca gac<br>Asp Val Lys Pro Leu His Ser Asp Gly Ala Phe Gly Gly Met Thr Asp<br>                325                330                335 | 1008 |
| gaa gcc aaa gct cgg gct cag aag atc cct aaa tct cgt tac gat ggc<br>Glu Ala Lys Ala Arg Ala Gln Lys Ile Pro Lys Ser Arg Tyr Asp Gly<br>                340                345                350 | 1056 |
| atc gat tct ttc ctt ggt gat att cag aac gat ttc gca aaa gat ggg<br>Ile Asp Ser Phe Leu Gly Asp Ile Gln Asn Asp Phe Ala Lys Asp Gly<br>                355                360                365 | 1104 |
| gaa gca gtg ttc aag tac ttc tct cca gag ttg aac gac atc agc cct<br>Glu Ala Val Phe Lys Tyr Phe Ser Pro Glu Leu Asn Asp Ile Ser Pro<br>370                  375                380 | 1152 |
| cca atc aac gag agg acg cta cag aga ctc gca cag gaa cct cag ttc<br>Pro Ile Asn Glu Arg Thr Leu Gln Arg Leu Ala Gln Glu Pro Gln Phe<br>385                  390                395                400 | 1200 |
| gac cct gtc ctt gct cat cac ttt gca cac ttg tac gtt cgt gat cca<br>Asp Pro Val Leu Ala His His Phe Ala His Leu Tyr Val Arg Asp Pro<br>                405                410                415 | 1248 |
| att gtg ata ttc gaa gaa cgt ata cac caa gac aat gac gtt gaa acg<br>Ile Val Ile Phe Glu Glu Arg Ile His Gln Asp Asn Asp Val Glu Thr<br>                420                425                430 | 1296 |
| gat cac ttt gag aac att caa tcc act aat tgg cag acg ttg agg ttc<br>Asp His Phe Glu Asn Ile Gln Ser Thr Asn Trp Gln Thr Leu Arg Phe<br>435                  440                445 | 1344 |
| aag cca cca act caa cag gca aca ccg gat aac aaa tcc gtt cca gga<br>Lys Pro Pro Thr Gln Gln Ala Thr Pro Asp Asn Lys Ser Val Pro Gly<br>450                  455                460 | 1392 |
| tgg aga gtg gaa ttc aga aca atg gag atc cag ctc aca gat ttt gag<br>Trp Arg Val Glu Phe Arg Thr Met Glu Ile Gln Leu Thr Asp Phe Glu<br>465                  470                475                480 | 1440 |
| aat gct gct ttc tca atc ttc att gtt ctc ctg gga cag gca ata ctt<br>Asn Ala Ala Phe Ser Ile Phe Ile Val Leu Leu Gly Gln Ala Ile Leu<br>                485                490                495 | 1488 |
| gcg aca gat tcc aac tgg tac att cca atc tcc aag att gaa gat aac<br>Ala Thr Asp Ser Asn Trp Tyr Ile Pro Ile Ser Lys Ile Glu Asp Asn<br>                500                505                510 | 1536 |
| atg aaa cgt gca cat cac agg gac gca gta ttg aag gac aag ttc cat<br>Met Lys Arg Ala His His Arg Asp Ala Val Leu Lys Asp Lys Phe His<br>                515                520                525 | 1584 |
| ttc aaa gct gat atc agc tcg cca gca ttc gac acg gtg gag ctg tca<br>Phe Lys Ala Asp Ile Ser Ser Pro Ala Phe Asp Thr Val Glu Leu Ser<br>530                  535                540 | 1632 |
| ctg gac gag att gtc aat ggc tgc gat agc ttt atc gga ttg atg gca<br>Leu Asp Glu Ile Val Asn Gly Cys Asp Ser Phe Ile Gly Leu Met Ala<br>545                  550                555                560 | 1680 |
| ctt gtg aag aag cac ttg gaa tct cgc ttt gga att act ggt gac gac<br>Leu Val Lys Lys His Leu Glu Ser Arg Phe Gly Ile Thr Gly Asp Asp<br>                565                570                575 | 1728 |
| tta tcg cca aag ggt aca cac gct agg atc tac tac tac ttg gaa ttg<br>Leu Ser Pro Lys Gly Thr His Ala Arg Ile Tyr Tyr Tyr Leu Glu Leu<br>                580                585                590 | 1776 |
| atc tcc aag aga gcc agt ggc gag cta cca act gct gct aaa ttc ata<br>Ile Ser Lys Arg Ala Ser Gly Glu Leu Pro Thr Ala Ala Lys Phe Ile<br>                595                600                605 | 1824 |
| aga agg ttc ttg ctc gac cat aag gac tat caa cac gac tcc aaa ata<br>Arg Arg Phe Leu Leu Asp His Lys Asp Tyr Gln His Asp Ser Lys Ile<br>610                  615                620 | 1872 |

```
act gct aga atg aat tac gat ttg ttg aac aag ttg aat agc att tca     1920
Thr Ala Arg Met Asn Tyr Asp Leu Leu Asn Lys Leu Asn Ser Ile Ser
625                 630                 635                 640 gaa ctt ggc gaa gat gtt aga cag ttg ttg ggt gat gac att ggc aac     1968
Glu Leu Gly Glu Asp Val Arg Gln Leu Leu Gly Asp Asp Ile Gly Asn
                645                 650                 655 tac ttg ata aac aac cca aag gct taa                                 1995
Tyr Leu Ile Asn Asn Pro Lys Ala
            660
```

<210> SEQ ID NO 2
<211> LENGTH: 664
<212> TYPE: PRT
<213> ORGANISM: Candida utilis

<400> SEQUENCE: 2

```
Met Gly Leu Leu Ser Leu Gly Thr Pro Leu Pro Trp Glu Gln Thr Arg
1               5                   10                  15

Glu Tyr Ala Glu His Val Arg Thr Glu Gly Ile Glu Gln Leu Ile Lys
            20                  25                  30

Met Phe Lys Ala Ala Tyr Ala Arg Thr Gly Asp Gly Tyr Leu Trp Gly
        35                  40                  45

Asp Glu Val Glu Tyr Thr Leu Val Lys Phe Asp His Gly Arg Gly Leu
    50                  55                  60

Ala Leu Leu Ser Ile Asp Lys Asp Ser Val Leu Ala Asp Leu Asn Glu
65                  70                  75                  80

Gly Gly Ser Leu Ala Gln Leu Ser Val Asp Asn Asp Leu Asn Phe His
                85                  90                  95

Pro Glu Tyr Gly Arg Phe Met Leu Glu Ala Thr Pro Leu Ala Pro Tyr
            100                 105                 110

Asn Gly Asp Ser Leu Glu Asn Tyr Leu Tyr Val Glu Arg Asn Met Asn
        115                 120                 125

Ser Arg Arg Ser Val Ala Gln Thr Ala Ile Ala Asp Gly Thr Ile Lys
    130                 135                 140

Pro Leu Thr Ile Thr Val Tyr Pro Leu Met Gly Ile Asn Thr Phe Thr
145                 150                 155                 160

Phe Pro Ser Ala Val Ala Asn Gly Glu Ala Ser Gln Ser Leu Phe Leu
                165                 170                 175

Pro Asp Glu Ile Ile Asn Arg His Ala Arg Phe Pro Thr Leu Thr Ala
            180                 185                 190

Asn Ile Arg Lys Arg Gly Glu Lys Val Ala Ile Asn Val Pro Leu
        195                 200                 205

Tyr Lys Asp Thr Asn Thr Leu Ser Ile Asp Glu Ser Ile Pro Lys Gly
    210                 215                 220

Arg Ser Leu Phe Lys His Asp Glu Glu Pro Glu Leu Gly Ala Ala Leu
225                 230                 235                 240

Pro Gly His Ile Tyr Met Asp Ser Met Gly Phe Gly Met Gly Cys Ser
                245                 250                 255

Cys Leu Gln Val Thr Val Gln Ala Pro Asn Leu Asn Arg Ala Arg Tyr
            260                 265                 270

Leu Tyr Asp Ser Trp Ala Asn Phe Ala Pro Leu Phe Leu Ala Leu Thr
        275                 280                 285

Ala Ala Ala Pro Val Phe Lys Gly His Leu Ala Asp Gln Asp Val Arg
    290                 295                 300

Trp Asn Val Ile Ser Gly Ala Val Asp Asp Arg Thr Ala Tyr Glu Arg
```

```
            305                 310                 315                 320
Asp Val Lys Pro Leu His Ser Asp Gly Ala Phe Gly Gly Met Thr Asp
                325                 330                 335

Glu Ala Lys Ala Arg Ala Gln Lys Ile Pro Lys Ser Arg Tyr Asp Gly
                340                 345                 350

Ile Asp Ser Phe Leu Gly Asp Ile Gln Asn Asp Phe Ala Lys Asp Gly
                355                 360                 365

Glu Ala Val Phe Lys Tyr Phe Ser Pro Glu Leu Asn Asp Ile Ser Pro
                370                 375                 380

Pro Ile Asn Glu Arg Thr Leu Gln Arg Leu Ala Gln Glu Pro Gln Phe
385                 390                 395                 400

Asp Pro Val Leu Ala His His Phe Ala His Leu Tyr Val Arg Asp Pro
                405                 410                 415

Ile Val Ile Phe Glu Glu Arg Ile His Gln Asn Asp Val Glu Thr
                420                 425                 430

Asp His Phe Glu Asn Ile Gln Ser Thr Asn Trp Gln Thr Leu Arg Phe
                435                 440                 445

Lys Pro Pro Thr Gln Gln Ala Thr Pro Asp Asn Lys Ser Val Pro Gly
                450                 455                 460

Trp Arg Val Glu Phe Arg Thr Met Glu Ile Gln Leu Thr Asp Phe Glu
465                 470                 475                 480

Asn Ala Ala Phe Ser Ile Phe Ile Val Leu Leu Gly Gln Ala Ile Leu
                485                 490                 495

Ala Thr Asp Ser Asn Trp Tyr Ile Pro Ile Ser Lys Ile Glu Asp Asn
                500                 505                 510

Met Lys Arg Ala His His Arg Asp Ala Val Leu Lys Asp Lys Phe His
                515                 520                 525

Phe Lys Ala Asp Ile Ser Ser Pro Ala Phe Asp Thr Val Glu Leu Ser
                530                 535                 540

Leu Asp Glu Ile Val Asn Gly Cys Asp Ser Phe Ile Gly Leu Met Ala
545                 550                 555                 560

Leu Val Lys Lys His Leu Glu Ser Arg Phe Gly Ile Thr Gly Asp Asp
                565                 570                 575

Leu Ser Pro Lys Gly Thr His Ala Arg Ile Tyr Tyr Leu Glu Leu
                580                 585                 590

Ile Ser Lys Arg Ala Ser Gly Glu Leu Pro Thr Ala Ala Lys Phe Ile
                595                 600                 605

Arg Arg Phe Leu Leu Asp His Lys Asp Tyr Gln His Asp Ser Lys Ile
610                 615                 620

Thr Ala Arg Met Asn Tyr Asp Leu Leu Asn Lys Leu Asn Ser Ile Ser
625                 630                 635                 640

Glu Leu Gly Glu Asp Val Arg Gln Leu Leu Gly Asp Asp Ile Gly Asn
                645                 650                 655

Tyr Leu Ile Asn Asn Pro Lys Ala
                660
```

<210> SEQ ID NO 3
<211> LENGTH: 41
<212> TYPE: DNA
<213> ORGANISM: Artificial Sequence
<220> FEATURE:
<223> OTHER INFORMATION: primer

<400> SEQUENCE: 3
agcatacaat caactggtac catggggctg ctatcattag g        41

```
<210> SEQ ID NO 4
<211> LENGTH: 62
<212> TYPE: DNA
<213> ORGANISM: Artificial Sequence
<220> FEATURE:
<223> OTHER INFORMATION: primer

<400> SEQUENCE: 4
ttcgcttagt taacctctag attaatgatg atgatgatga tgagcctttg ggttgtttat    60
ca                                                                  62

<210> SEQ ID NO 5
<211> LENGTH: 34
<212> TYPE: DNA
<213> ORGANISM: Artificial Sequence
<220> FEATURE:
<223> OTHER INFORMATION: primer

<400> SEQUENCE: 5
aatcaactgc tagcgggctg ctatcattag ggac                               34

<210> SEQ ID NO 6
<211> LENGTH: 38
<212> TYPE: DNA
<213> ORGANISM: Artificial Sequence
<220> FEATURE:
<223> OTHER INFORMATION: primer

<400> SEQUENCE: 6
tcataaatct cgaggaaatt cgcttagtta acctctag                           38

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
gataaggaga atccatacaa                                               20

<210> SEQ ID NO 8
<211> LENGTH: 60
<212> TYPE: DNA
<213> ORGANISM: Artificial Sequence
<220> FEATURE:
<223> OTHER INFORMATION: primer

<400> SEQUENCE: 8
gtgagtttag tatacatgca tttacttata atacagtttt gatttatctt cgtttcctgc   60

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
aaaactgtat tataagtaaa                                               20

<210> SEQ ID NO 10
<211> LENGTH: 20
<212> TYPE: DNA
```

```
<213> ORGANISM: Artificial Sequence
<220> FEATURE:
<223> OTHER INFORMATION: primer

<400> SEQUENCE: 10
cacttatttg cgatacagaa                                               20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
gataaggaga atccatacaa                                               20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
cacttatttg cgatacagaa                                               20

<210> SEQ ID NO 13
<211> LENGTH: 29
<212> TYPE: DNA
<213> ORGANISM: Artificial Sequence
<220> FEATURE:
<223> OTHER INFORMATION: primer

<400> SEQUENCE: 13
atagcatgct cataaaattg ataaggaga                                     29

<210> SEQ ID NO 14
<211> LENGTH: 29
<212> TYPE: DNA
<213> ORGANISM: Artificial Sequence
<220> FEATURE:
<223> OTHER INFORMATION: primer

<400> SEQUENCE: 14
atagaattca ggacgtcatt agtggcgaa                                     29

<210> SEQ ID NO 15
<211> LENGTH: 35
<212> TYPE: DNA
<213> ORGANISM: Artificial Sequence
<220> FEATURE:
<223> OTHER INFORMATION: primer

<400> SEQUENCE: 15
atactgcaga taatcgatta attttttttt ctttc                              35

<210> SEQ ID NO 16
<211> LENGTH: 29
<212> TYPE: DNA
<213> ORGANISM: Artificial Sequence
<220> FEATURE:
<223> OTHER INFORMATION: primer

<400> SEQUENCE: 16
atactgcaga agtagataat tacttccctt                                    29
```

```
<210> SEQ ID NO 17
<211> LENGTH: 26
<212> TYPE: DNA
<213> ORGANISM: Artificial Sequence
<220> FEATURE:
<223> OTHER INFORMATION: primer

<400> SEQUENCE: 17
atagacgtct aatttttttt tctttc                                           26

<210> SEQ ID NO 18
<211> LENGTH: 29
<212> TYPE: DNA
<213> ORGANISM: Artificial Sequence
<220> FEATURE:
<223> OTHER INFORMATION: primer

<400> SEQUENCE: 18
atagacgtct gttttatatt tgttgtaaa                                        29

<210> SEQ ID NO 19
<211> LENGTH: 100
<212> TYPE: DNA
<213> ORGANISM: Artificial Sequence
<220> FEATURE:
<223> OTHER INFORMATION: primer

<400> SEQUENCE: 19
tattgcccca gtgttccctc aacaaccttg gtagttggag cgcaattagc gtatcctgta      60
ccatactaat tctcttctgc tcttaaccca actgcacaga                           100

<210> SEQ ID NO 20
<211> LENGTH: 100
<212> TYPE: DNA
<213> ORGANISM: Artificial Sequence
<220> FEATURE:
<223> OTHER INFORMATION: primer

<400> SEQUENCE: 20
ataccttcat cccttatgtg ttcattgtac gtcctagact caaaccactg caaaggcgtg      60
cccaaagcta agagtcccat tgtatatgag atagttgatt                           100

<210> SEQ ID NO 21
<211> LENGTH: 30
<212> TYPE: DNA
<213> ORGANISM: Artificial Sequence
<220> FEATURE:
<223> OTHER INFORMATION: primer

<400> SEQUENCE: 21
agttacagca atgaaagagc agagcgagag                                       30

<210> SEQ ID NO 22
<211> LENGTH: 30
<212> TYPE: DNA
<213> ORGANISM: Artificial Sequence
<220> FEATURE:
<223> OTHER INFORMATION: primer

<400> SEQUENCE: 22
attactgctg ctgttccagc ccatatccaa                                       30

<210> SEQ ID NO 23
```

```
<211> LENGTH: 30
<212> TYPE: DNA
<213> ORGANISM: Artificial Sequence
<220> FEATURE:
<223> OTHER INFORMATION: primer

<400> SEQUENCE: 23
agttacagca atgaaagagc agagcgagag                                      30

<210> SEQ ID NO 24
<211> LENGTH: 30
<212> TYPE: DNA
<213> ORGANISM: Artificial Sequence
<220> FEATURE:
<223> OTHER INFORMATION: primer

<400> SEQUENCE: 24
attactgctg ctgttccagc ccatatccaa                                      30

<210> SEQ ID NO 25
<211> LENGTH: 35
<212> TYPE: DNA
<213> ORGANISM: Artificial Sequence
<220> FEATURE:
<223> OTHER INFORMATION: primer

<400> SEQUENCE: 25
gcagcccggg ggatcatggg gctgctatca ttagg                                35

<210> SEQ ID NO 26
<211> LENGTH: 38
<212> TYPE: DNA
<213> ORGANISM: Artificial Sequence
<220> FEATURE:
<223> OTHER INFORMATION: primer

<400> SEQUENCE: 26
tagaactagt ggatcttaag ccctttgggt tgtttatc                             38

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
ttacgccaag cgcgcaatta                                                 20

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
tcatggtcat agctgtttcc                                                 20

<210> SEQ ID NO 29
<211> LENGTH: 35
<212> TYPE: DNA
<213> ORGANISM: Artificial Sequence
<220> FEATURE:
<223> OTHER INFORMATION: primer

<400> SEQUENCE: 29
```

```
gcgcgcttgg cgtaacaaat agctctctac ttgct                                35
```

<210> SEQ ID NO 30
<211> LENGTH: 34
<212> TYPE: DNA
<213> ORGANISM: Artificial Sequence
<220> FEATURE:
<223> OTHER INFORMATION: primer

<400> SEQUENCE: 30

```
cagctatgac catgagcaat ctacaacttc gaaa                                 34
```

<210> SEQ ID NO 31
<211> LENGTH: 1476
<212> TYPE: DNA
<213> ORGANISM: Saccharomyces cerevisiae
<220> FEATURE:
<221> NAME/KEY: CDS
<222> LOCATION: (1)..(1476)

<400> SEQUENCE: 31

```
atg gca cac tat cca cct tcc aag gat caa ttg aat gaa ttg atc cag       48
Met Ala His Tyr Pro Pro Ser Lys Asp Gln Leu Asn Glu Leu Ile Gln
1               5                   10                  15 gaa gtt aac caa tgg gct atc act aat gga tta tcc atg tat cct cct       96
Glu Val Asn Gln Trp Ala Ile Thr Asn Gly Leu Ser Met Tyr Pro Pro
            20                  25                  30 aaa ttc gag gag aac cca tca aat gca tcg gtg tca cca gta act atc      144
Lys Phe Glu Glu Asn Pro Ser Asn Ala Ser Val Ser Pro Val Thr Ile
        35                  40                  45 tat cca acc cca att cct agg aaa tgt ttt gat gag gcc gtt caa ata      192
Tyr Pro Thr Pro Ile Pro Arg Lys Cys Phe Asp Glu Ala Val Gln Ile
    50                  55                  60 caa ccg gta ttc aat gaa tta tac gcc cgt att acc caa gat atg gcc      240
Gln Pro Val Phe Asn Glu Leu Tyr Ala Arg Ile Thr Gln Asp Met Ala
65                  70                  75                  80 caa cct gat tct tat tta cat aaa aca act gaa gcg tta gct cta tca      288
Gln Pro Asp Ser Tyr Leu His Lys Thr Thr Glu Ala Leu Ala Leu Ser
                85                  90                  95 gat tcc gag ttt act gga aaa ctg tgg tct cta tac ctt gct acc tta      336
Asp Ser Glu Phe Thr Gly Lys Leu Trp Ser Leu Tyr Leu Ala Thr Leu
            100                 105                 110 aaa tct gca cag tac aaa aag cag aat ttt agg cta ggt ata ttt aga      384
Lys Ser Ala Gln Tyr Lys Lys Gln Asn Phe Arg Leu Gly Ile Phe Arg
        115                 120                 125 tca gat tat ttg att gat aag aaa aag ggt act gaa cag att aag caa      432
Ser Asp Tyr Leu Ile Asp Lys Lys Lys Gly Thr Glu Gln Ile Lys Gln
    130                 135                 140 gtc gag ttt aat aca gtg tca gtg tca ttt gca ggc ctt agc gag aaa      480
Val Glu Phe Asn Thr Val Ser Val Ser Phe Ala Gly Leu Ser Glu Lys
145                 150                 155                 160 gtt gat aga ttg cac tct tat tta aat agg gca aac aag tac gat cct      528
Val Asp Arg Leu His Ser Tyr Leu Asn Arg Ala Asn Lys Tyr Asp Pro
                165                 170                 175 aaa gga cca att tat aat gat caa aat atg gtc att tct gat tca gga      576
Lys Gly Pro Ile Tyr Asn Asp Gln Asn Met Val Ile Ser Asp Ser Gly
            180                 185                 190 tac ctt ttg tct aag gca ttg gcc aaa gct gtg gaa tcg tat aag tca      624
Tyr Leu Leu Ser Lys Ala Leu Ala Lys Ala Val Glu Ser Tyr Lys Ser
        195                 200                 205 caa caa agt tct tct aca act agt gat cct att gtc gca ttc att gtg      672
Gln Gln Ser Ser Ser Thr Thr Ser Asp Pro Ile Val Ala Phe Ile Val
```

| | | | | | | | | | | | | | |
|---|---|---|---|---|---|---|---|---|---|---|---|---|---|
| Gln | Gln | Ser | Ser | Ser | Thr | Thr | Ser | Asp | Pro | Ile | Val | Ala | Phe | Ile | Val |
| 210 | | | | | 215 | | | | | 220 | | | | |

```
caa aga aac gag aga aat gtg ttt gat caa aag gtc ttg gaa ttg aat      720
Gln Arg Asn Glu Arg Asn Val Phe Asp Gln Lys Val Leu Glu Leu Asn
225                 230                 235                 240 ctg ttg gaa aaa ttc ggt acc aaa tct gtt agg ttg acg ttt gat gat      768
Leu Leu Glu Lys Phe Gly Thr Lys Ser Val Arg Leu Thr Phe Asp Asp
                245                 250                 255 gtt aac gat aaa ttg ttc att gat gat aaa acg gga aag ctt ttc att      816
Val Asn Asp Lys Leu Phe Ile Asp Asp Lys Thr Gly Lys Leu Phe Ile
            260                 265                 270 agg gac aca gag cag gaa ata gcg gtg gtt tat tac aga acg ggt tac      864
Arg Asp Thr Glu Gln Glu Ile Ala Val Val Tyr Tyr Arg Thr Gly Tyr
        275                 280                 285 aca acc act gat tac acg tcc gaa aag gac tgg gag gca aga cta ttc      912
Thr Thr Thr Asp Tyr Thr Ser Glu Lys Asp Trp Glu Ala Arg Leu Phe
    290                 295                 300 ctc gaa aaa agt ttc gca ata aag gcc cca gat tta ctc act caa tta      960
Leu Glu Lys Ser Phe Ala Ile Lys Ala Pro Asp Leu Leu Thr Gln Leu
305                 310                 315                 320 tct ggc tcc aag aaa att cag caa ttg ttg aca gat gag ggc gta tta     1008
Ser Gly Ser Lys Lys Ile Gln Gln Leu Leu Thr Asp Glu Gly Val Leu
                325                 330                 335 ggt aaa tac atc tcc gat gct gag aaa aag agt agt ttg tta aaa act     1056
Gly Lys Tyr Ile Ser Asp Ala Glu Lys Lys Ser Ser Leu Leu Lys Thr
            340                 345                 350 ttt gtc aaa ata tat ccc ttg gat gat acg aag ctt ggc agg gaa ggc     1104
Phe Val Lys Ile Tyr Pro Leu Asp Asp Thr Lys Leu Gly Arg Glu Gly
        355                 360                 365 aag agg ctg gca tta agt gag ccc tct aaa tac gtg tta aaa cca cag     1152
Lys Arg Leu Ala Leu Ser Glu Pro Ser Lys Tyr Val Leu Lys Pro Gln
    370                 375                 380 cgg gaa ggt ggc gga aac aat gtt tat aaa gaa aat att cct aat ttt     1200
Arg Glu Gly Gly Gly Asn Asn Val Tyr Lys Glu Asn Ile Pro Asn Phe
385                 390                 395                 400 ttg aaa ggt atc gaa gaa cgt cac tgg gat gca tat att ctc atg gag     1248
Leu Lys Gly Ile Glu Glu Arg His Trp Asp Ala Tyr Ile Leu Met Glu
                405                 410                 415 ttg att gaa cca gag ttg aat gaa aat aat att ata tta cgt gat aac     1296
Leu Ile Glu Pro Glu Leu Asn Glu Asn Asn Ile Ile Leu Arg Asp Asn
            420                 425                 430 aaa tct tac aac gaa cca atc atc agt gaa cta gga att tat ggt tgc     1344
Lys Ser Tyr Asn Glu Pro Ile Ile Ser Glu Leu Gly Ile Tyr Gly Cys
        435                 440                 445 gtt cta ttt aac gac gag caa gtt tta tcg aac gaa ttt agt ggc tca     1392
Val Leu Phe Asn Asp Glu Gln Val Leu Ser Asn Glu Phe Ser Gly Ser
    450                 455                 460 tta cta aga tcc aaa ttt aat act tca aat gaa ggt gga gtg gcg gca     1440
Leu Leu Arg Ser Lys Phe Asn Thr Ser Asn Glu Gly Gly Val Ala Ala
465                 470                 475                 480 gga ttc gga tgt ttg gac agt att att ctt tac tag                     1476
Gly Phe Gly Cys Leu Asp Ser Ile Ile Leu Tyr
                485                 490
```

<210> SEQ ID NO 32
<211> LENGTH: 491
<212> TYPE: PRT
<213> ORGANISM: Saccharomyces cerevisiae

<400> SEQUENCE: 32

```
Met Ala His Tyr Pro Pro Ser Lys Asp Gln Leu Asn Glu Leu Ile Gln
1               5                   10                  15

Glu Val Asn Gln Trp Ala Ile Thr Asn Gly Leu Ser Met Tyr Pro Pro
            20                  25                  30

Lys Phe Glu Glu Asn Pro Ser Asn Ala Ser Val Ser Pro Val Thr Ile
        35                  40                  45

Tyr Pro Thr Pro Ile Pro Arg Lys Cys Phe Asp Glu Ala Val Gln Ile
50                  55                  60

Gln Pro Val Phe Asn Glu Leu Tyr Ala Arg Ile Thr Gln Asp Met Ala
65                  70                  75                  80

Gln Pro Asp Ser Tyr Leu His Lys Thr Thr Glu Ala Leu Ala Leu Ser
                85                  90                  95

Asp Ser Glu Phe Thr Gly Lys Leu Trp Ser Leu Tyr Leu Ala Thr Leu
            100                 105                 110

Lys Ser Ala Gln Tyr Lys Lys Gln Asn Phe Arg Leu Gly Ile Phe Arg
        115                 120                 125

Ser Asp Tyr Leu Ile Asp Lys Lys Lys Gly Thr Glu Gln Ile Lys Gln
130                 135                 140

Val Glu Phe Asn Thr Val Ser Val Ser Phe Ala Gly Leu Ser Glu Lys
145                 150                 155                 160

Val Asp Arg Leu His Ser Tyr Leu Asn Arg Ala Asn Lys Tyr Asp Pro
                165                 170                 175

Lys Gly Pro Ile Tyr Asn Asp Gln Asn Met Val Ile Ser Asp Ser Gly
            180                 185                 190

Tyr Leu Leu Ser Lys Ala Leu Ala Lys Ala Val Glu Ser Tyr Lys Ser
        195                 200                 205

Gln Gln Ser Ser Thr Thr Ser Asp Pro Ile Val Ala Phe Ile Val
210                 215                 220

Gln Arg Asn Glu Arg Asn Val Phe Asp Gln Lys Val Leu Glu Leu Asn
225                 230                 235                 240

Leu Leu Glu Lys Phe Gly Thr Lys Ser Val Arg Leu Thr Phe Asp Asp
            245                 250                 255

Val Asn Asp Lys Leu Phe Ile Asp Asp Lys Thr Gly Lys Leu Phe Ile
        260                 265                 270

Arg Asp Thr Glu Gln Glu Ile Ala Val Val Tyr Tyr Arg Thr Gly Tyr
275                 280                 285

Thr Thr Thr Asp Tyr Thr Ser Glu Lys Asp Trp Glu Ala Arg Leu Phe
290                 295                 300

Leu Glu Lys Ser Phe Ala Ile Lys Ala Pro Asp Leu Leu Thr Gln Leu
305                 310                 315                 320

Ser Gly Ser Lys Lys Ile Gln Gln Leu Leu Thr Asp Glu Gly Val Leu
            325                 330                 335

Gly Lys Tyr Ile Ser Asp Ala Glu Lys Lys Ser Ser Leu Leu Lys Thr
        340                 345                 350

Phe Val Lys Ile Tyr Pro Leu Asp Asp Thr Lys Leu Gly Arg Glu Gly
355                 360                 365

Lys Arg Leu Ala Leu Ser Glu Pro Ser Lys Tyr Val Leu Lys Pro Gln
370                 375                 380

Arg Glu Gly Gly Gly Asn Val Tyr Lys Glu Asn Ile Pro Asn Phe
385                 390                 395                 400

Leu Lys Gly Ile Glu Glu Arg His Trp Asp Ala Tyr Ile Leu Met Glu
            405                 410                 415

Leu Ile Glu Pro Glu Leu Asn Glu Asn Asn Ile Ile Leu Arg Asp Asn
```

```
            420                 425                 430
Lys Ser Tyr Asn Glu Pro Ile Ile Ser Glu Leu Gly Ile Tyr Gly Cys
            435                 440                 445

Val Leu Phe Asn Asp Glu Gln Val Leu Ser Asn Glu Phe Ser Gly Ser
        450                 455                 460

Leu Leu Arg Ser Lys Phe Asn Thr Ser Asn Glu Gly Gly Val Ala Ala
465                 470                 475                 480

Gly Phe Gly Cys Leu Asp Ser Ile Ile Leu Tyr
                485                 490
```

<210> SEQ ID NO 33
<211> LENGTH: 41
<212> TYPE: DNA
<213> ORGANISM: Artificial Sequence
<220> FEATURE:
<223> OTHER INFORMATION: primer

<400> SEQUENCE: 33
agcatacaat caactggtac catggcacac tatccacctt c    41

<210> SEQ ID NO 34
<211> LENGTH: 62
<212> TYPE: DNA
<213> ORGANISM: Artificial Sequence
<220> FEATURE:
<223> OTHER INFORMATION: primer

<400> SEQUENCE: 34
ttcgcttagt taacctctag actaatgatg atgatgatga tggtaaagaa taatactgtc    60
ca    62

<210> SEQ ID NO 35
<211> LENGTH: 34
<212> TYPE: DNA
<213> ORGANISM: Artificial Sequence
<220> FEATURE:
<223> OTHER INFORMATION: primer

<400> SEQUENCE: 35
aatcaactca tatgatggca cactatccac cttc    34

<210> SEQ ID NO 36
<211> LENGTH: 38
<212> TYPE: DNA
<213> ORGANISM: Artificial Sequence
<220> FEATURE:
<223> OTHER INFORMATION: primer

<400> SEQUENCE: 36
tcataaatct cgaggaaatt cgcttagtta acctctag    38

<210> SEQ ID NO 37
<211> LENGTH: 20
<212> TYPE: DNA
<213> ORGANISM: Artificial Sequence
<220> FEATURE:
<223> OTHER INFORMATION: primer

<400> SEQUENCE: 37
ctagtgaaaa acaagaagta    20

<210> SEQ ID NO 38
<211> LENGTH: 20

<212> TYPE: DNA
<213> ORGANISM: Artificial Sequence
<220> FEATURE:
<223> OTHER INFORMATION: primer

<400> SEQUENCE: 38
gccacataga aaaatcgatg                                                  20

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
aagtagccaa tacaaccagc                                                  20

<210> SEQ ID NO 40
<211> LENGTH: 51
<212> TYPE: DNA
<213> ORGANISM: Artificial Sequence
<220> FEATURE:
<223> OTHER INFORMATION: primer

<400> SEQUENCE: 40
ctgcagcgta cgaagcttca gctggcgggc cactcaccca ctcaacatca c               51

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
gctgttttag actcgtttgc                                                  20

<210> SEQ ID NO 42
<211> LENGTH: 50
<212> TYPE: DNA
<213> ORGANISM: Artificial Sequence
<220> FEATURE:
<223> OTHER INFORMATION: primer

<400> SEQUENCE: 42
ctgcagcgta cgaagcttca gctggcggcc agaagattca gacaccggga                 50

<210> SEQ ID NO 43
<211> LENGTH: 50
<212> TYPE: DNA
<213> ORGANISM: Artificial Sequence
<220> FEATURE:
<223> OTHER INFORMATION: primer

<400> SEQUENCE: 43
attaggtgat atcagatcca ctagtggcct ggtttcttaa gatctattcc                 50

<210> SEQ ID NO 44
<211> LENGTH: 21
<212> TYPE: DNA
<213> ORGANISM: Artificial Sequence
<220> FEATURE:
<223> OTHER INFORMATION: primer

<400> SEQUENCE: 44
taaatgcggc tccatctatt g                                               21

<210> SEQ ID NO 45
<211> LENGTH: 29
<212> TYPE: DNA
<213> ORGANISM: Artificial Sequence
<220> FEATURE:
<223> OTHER INFORMATION: primer

<400> SEQUENCE: 45
ataaccggtg ggtgtacaat atggacttc                                       29

<210> SEQ ID NO 46
<211> LENGTH: 29
<212> TYPE: DNA
<213> ORGANISM: Artificial Sequence
<220> FEATURE:
<223> OTHER INFORMATION: primer

<400> SEQUENCE: 46
ataaagcttt gtatatgaga tagttgatt                                       29

<210> SEQ ID NO 47
<211> LENGTH: 24
<212> TYPE: DNA
<213> ORGANISM: Artificial Sequence
<220> FEATURE:
<223> OTHER INFORMATION: primer

<400> SEQUENCE: 47
ggatccatgt tgcagagaca ttcc                                            24

<210> SEQ ID NO 48
<211> LENGTH: 21
<212> TYPE: DNA
<213> ORGANISM: Artificial Sequence
<220> FEATURE:
<223> OTHER INFORMATION: primer

<400> SEQUENCE: 48
tctagattag ttcaagtcgg c                                               21

<210> SEQ ID NO 49
<211> LENGTH: 22
<212> TYPE: DNA
<213> ORGANISM: Artificial Sequence
<220> FEATURE:
<223> OTHER INFORMATION: primer

<400> SEQUENCE: 49
aagcttggcc tcgctaatat ac                                              22

<210> SEQ ID NO 50
<211> LENGTH: 23
<212> TYPE: DNA
<213> ORGANISM: Artificial Sequence
<220> FEATURE:
<223> OTHER INFORMATION: primer

<400> SEQUENCE: 50
tctagaacag acaagaaacc gtc                                             23

<210> SEQ ID NO 51
<211> LENGTH: 2182
<212> TYPE: DNA
<213> ORGANISM: Saccharomyces cerevisiae

<220> FEATURE:
<221> NAME/KEY: CDS
<222> LOCATION: (501)..(1682)

<400> SEQUENCE: 51

```
gaaatgcgca ccacaagctt gatggcattt ccttctgcac ttctcaaatt gatagcattg      60
ccttgcgagc agtagataat ttagataaag tgtatcttgc cagggccttc ccaggcatta     120
actagataat gtgttctttt ttagctgaac tgtaaagcgt aaatgttaac gctggataag     180
taccgcgtgt acggttgatt gaatgatctt actgatagag gccaggcggt tgatactttg     240
tgcagatttc ataccggctg tcgctattat tactgatgaa ttggctctct ttttgtttaa     300
tggcccatcc gatccatatt gccttcttat gactcaaaat tctattgtgt ttgccggtac     360
cggcctttaa gctttgaaaa aaaaaagca tctgaaaaaa atggcactat aaagagagct     420
agtggtaaca actacatgtt ttcgttagaa taaatcaccc tataaacgca aaatcagcta     480
gaaccttagc atactaaaac atg ttg cag aga cat tcc ttg aag ttg ggg aaa   533
                       Met Leu Gln Arg His Ser Leu Lys Leu Gly Lys
                         1               5                  10 ttc tcc atc aga aca ctc gct act ggt gcc cca tta gat gca tcc aaa     581
Phe Ser Ile Arg Thr Leu Ala Thr Gly Ala Pro Leu Asp Ala Ser Lys
         15                  20                  25 cta aaa att act aga aac cca aat cca tcc aag cca aga cca aat gaa     629
Leu Lys Ile Thr Arg Asn Pro Asn Pro Ser Lys Pro Arg Pro Asn Glu
 30                  35                  40 gaa tta gtg ttc ggc cag aca ttc acc gat cat atg ttg acc att cct     677
Glu Leu Val Phe Gly Gln Thr Phe Thr Asp His Met Leu Thr Ile Pro
 45                  50                  55 tgg tca gcc aaa gaa ggg tgg ggc act cca cac atc aag cct tac ggt     725
Trp Ser Ala Lys Glu Gly Trp Gly Thr Pro His Ile Lys Pro Tyr Gly
 60                  65                  70                  75 aat ctt tct ctt gac cca tct gct tgt gta ttc cat tat gca ttt gaa     773
Asn Leu Ser Leu Asp Pro Ser Ala Cys Val Phe His Tyr Ala Phe Glu
                 80                  85                  90 tta ttt gaa ggt ttg aaa gcc tac aga act cct caa aat act atc acc     821
Leu Phe Glu Gly Leu Lys Ala Tyr Arg Thr Pro Gln Asn Thr Ile Thr
         95                 100                 105 atg ttc cgt ccg gat aag aac atg gcc cgt atg aac aag tct gcc gct     869
Met Phe Arg Pro Asp Lys Asn Met Ala Arg Met Asn Lys Ser Ala Ala
            110                 115                 120 aga att tgt ttg cca act ttc gaa tct gaa gaa ttg atc aaa ctt acc     917
Arg Ile Cys Leu Pro Thr Phe Glu Ser Glu Glu Leu Ile Lys Leu Thr
125                 130                 135 ggg aaa ttg atc gaa caa gat aaa cac ttg gtt cct caa ggt aat ggt     965
Gly Lys Leu Ile Glu Gln Asp Lys His Leu Val Pro Gln Gly Asn Gly
140                 145                 150                 155 tac tca tta tac atc aga cca aca atg att ggt aca tcc aag ggt tta    1013
Tyr Ser Leu Tyr Ile Arg Pro Thr Met Ile Gly Thr Ser Lys Gly Leu
                160                 165                 170 ggt gtt ggc act ccc tcc gag gct ctt ctt tat gtt att act tct cca    1061
Gly Val Gly Thr Pro Ser Glu Ala Leu Leu Tyr Val Ile Thr Ser Pro
        175                 180                 185 gtc ggt cct tat tat aag act ggt ttc aaa gcc gta cgt ctt gaa gca    1109
Val Gly Pro Tyr Tyr Lys Thr Gly Phe Lys Ala Val Arg Leu Glu Ala
            190                 195                 200 aca gac tat gct aca aga gct tgg cca ggt ggt gtt ggc gac aaa aaa    1157
Thr Asp Tyr Ala Thr Arg Ala Trp Pro Gly Gly Val Gly Asp Lys Lys
205                 210                 215 ttg ggt gct aac tat gcc cca tgc atc tta cct caa cta caa gct gcc    1205
Leu Gly Ala Asn Tyr Ala Pro Cys Ile Leu Pro Gln Leu Gln Ala Ala
```

| | | | | | | | | | | | | | | | |
|---|---|---|---|---|---|---|---|---|---|---|---|---|---|---|---|
| Leu | Gly | Ala | Asn | Tyr | Ala | Pro | Cys | Ile | Leu | Pro | Gln | Leu | Gln | Ala | Ala |
| 220 | | | | 225 | | | | | 230 | | | | | 235 | |

```
aaa aga ggg tac caa caa aat cta tgg ttg ttc ggc cca gaa aag aac       1253
Lys Arg Gly Tyr Gln Gln Asn Leu Trp Leu Phe Gly Pro Glu Lys Asn
            240                 245                 250 atc act gag gtt ggt act atg aac gtg ttc ttc gtt ttc ctc aac aaa       1301
Ile Thr Glu Val Gly Thr Met Asn Val Phe Phe Val Phe Leu Asn Lys
                255                 260                 265 gtc act ggc aag aag gaa ttg gtt acc gct cca tta gat ggt acc att       1349
Val Thr Gly Lys Lys Glu Leu Val Thr Ala Pro Leu Asp Gly Thr Ile
            270                 275                 280 tta gaa ggt gtt acc aga gac tct gtt tta aca ttg gct cgt gac aaa       1397
Leu Glu Gly Val Thr Arg Asp Ser Val Leu Thr Leu Ala Arg Asp Lys
        285                 290                 295 cta gat cct caa gaa tgg gac atc aac gag cgt tat tac act att act       1445
Leu Asp Pro Gln Glu Trp Asp Ile Asn Glu Arg Tyr Tyr Thr Ile Thr
300                 305                 310                 315 gaa gtc gcc act aga gca aaa caa ggt gaa cta tta gaa gcc ttc ggt       1493
Glu Val Ala Thr Arg Ala Lys Gln Gly Glu Leu Leu Glu Ala Phe Gly
                320                 325                 330 tct ggt act gct gct gtc gtt tca cct atc aag gaa att ggc tgg aac       1541
Ser Gly Thr Ala Ala Val Val Ser Pro Ile Lys Glu Ile Gly Trp Asn
            335                 340                 345 aac gaa gat att cat gtt cca cta ttg cct ggt gaa caa tgt ggt gca       1589
Asn Glu Asp Ile His Val Pro Leu Leu Pro Gly Glu Gln Cys Gly Ala
        350                 355                 360 ttg acc aag caa gtt gct caa tgg att gct gat atc caa tac ggt aga       1637
Leu Thr Lys Gln Val Ala Gln Trp Ile Ala Asp Ile Gln Tyr Gly Arg
365                 370                 375 gtc aat tat ggt aac tgg tca aaa act gtt gcc gac ttg aac taa          1682
Val Asn Tyr Gly Asn Trp Ser Lys Thr Val Ala Asp Leu Asn
                380                 385                 390 tgataatgaa ggtaaacatc ccctccccccc ccaaaaaaaa aaaacgagaa ttcctctcag    1742
aggatctgtt tttctctcac tttattcaca tagatacata cttttttaca attcctgttg    1802
agtttattta ttataagaaa tattggatta ctattattat tatagcttat gcaagccatt    1862
gtgcggcttc ttacgctttt tgaaattgtt gacctaacaa cttggcacat tattgaattt    1922
catagagact gcttgtaatt tagttgccaa ggtatctcgc tggactttac atgtaaaatg    1982
aatgcggcaa gatacccaag agagttgatt atgccaaaaa aaaaaaatct ataaggatat    2042
ccctggtatt ttctgaagaa taaattctag cgtagttcag aagaggtgca agtacagtat    2102
gaataatggt atgccttcca tcatcgtggc atacaggttc aggcatgaag agatgattat    2162
gttccctcac cggtccataa                                                2182

<210> SEQ ID NO 52
<211> LENGTH: 393
<212> TYPE: PRT
<213> ORGANISM: Saccharomyces cerevisiae

<400> SEQUENCE: 52
```

| | | | | | | | | | | | | | | | |
|---|---|---|---|---|---|---|---|---|---|---|---|---|---|---|---|
| Met | Leu | Gln | Arg | His | Ser | Leu | Lys | Leu | Gly | Lys | Phe | Ser | Ile | Arg | Thr |
| 1 | | | | 5 | | | | | 10 | | | | | 15 | |

| | | | | | | | | | | | | | | | |
|---|---|---|---|---|---|---|---|---|---|---|---|---|---|---|---|
| Leu | Ala | Thr | Gly | Ala | Pro | Leu | Asp | Ala | Ser | Lys | Leu | Lys | Ile | Thr | Arg |
| | | | 20 | | | | | 25 | | | | | 30 | | |

| | | | | | | | | | | | | | | | |
|---|---|---|---|---|---|---|---|---|---|---|---|---|---|---|---|
| Asn | Pro | Asn | Pro | Ser | Lys | Pro | Arg | Pro | Asn | Glu | Glu | Leu | Val | Phe | Gly |
| | | 35 | | | | | 40 | | | | | 45 | | | |

| | | | | | | | | | | | | | | | |
|---|---|---|---|---|---|---|---|---|---|---|---|---|---|---|---|
| Gln | Thr | Phe | Thr | Asp | His | Met | Leu | Thr | Ile | Pro | Trp | Ser | Ala | Lys | Glu |

```
            50                 55                 60
Gly Trp Gly Thr Pro His Ile Lys Pro Tyr Gly Asn Leu Ser Leu Asp
 65                 70                  75                  80

Pro Ser Ala Cys Val Phe His Tyr Ala Phe Glu Leu Phe Glu Gly Leu
                 85                  90                  95

Lys Ala Tyr Arg Thr Pro Gln Asn Thr Ile Thr Met Phe Arg Pro Asp
                100                 105                 110

Lys Asn Met Ala Arg Met Asn Lys Ser Ala Ala Arg Ile Cys Leu Pro
            115                 120                 125

Thr Phe Glu Ser Glu Glu Leu Ile Lys Leu Thr Gly Lys Leu Ile Glu
            130                 135                 140

Gln Asp Lys His Leu Val Pro Gln Gly Asn Gly Tyr Ser Leu Tyr Ile
145                 150                 155                 160

Arg Pro Thr Met Ile Gly Thr Ser Lys Gly Leu Gly Val Gly Thr Pro
                165                 170                 175

Ser Glu Ala Leu Leu Tyr Val Ile Thr Ser Pro Val Gly Pro Tyr Tyr
                180                 185                 190

Lys Thr Gly Phe Lys Ala Val Arg Leu Glu Ala Thr Asp Tyr Ala Thr
                195                 200                 205

Arg Ala Trp Pro Gly Gly Val Gly Asp Lys Lys Leu Gly Ala Asn Tyr
210                 215                 220

Ala Pro Cys Ile Leu Pro Gln Leu Gln Ala Ala Lys Arg Gly Tyr Gln
225                 230                 235                 240

Gln Asn Leu Trp Leu Phe Gly Pro Glu Lys Asn Ile Thr Glu Val Gly
                245                 250                 255

Thr Met Asn Val Phe Phe Val Phe Leu Asn Lys Val Thr Gly Lys Lys
                260                 265                 270

Glu Leu Val Thr Ala Pro Leu Asp Gly Thr Ile Leu Glu Gly Val Thr
                275                 280                 285

Arg Asp Ser Val Leu Thr Leu Ala Arg Asp Lys Leu Asp Pro Gln Glu
290                 295                 300

Trp Asp Ile Asn Glu Arg Tyr Tyr Thr Ile Thr Glu Val Ala Thr Arg
305                 310                 315                 320

Ala Lys Gln Gly Glu Leu Leu Glu Ala Phe Gly Ser Gly Thr Ala Ala
                325                 330                 335

Val Val Ser Pro Ile Lys Glu Ile Gly Trp Asn Asn Glu Asp Ile His
                340                 345                 350

Val Pro Leu Leu Pro Gly Glu Gln Cys Gly Ala Leu Thr Lys Gln Val
                355                 360                 365

Ala Gln Trp Ile Ala Asp Ile Gln Tyr Gly Arg Val Asn Tyr Gly Asn
                370                 375                 380

Trp Ser Lys Thr Val Ala Asp Leu Asn
385                 390
```

<210> SEQ ID NO 53
<211> LENGTH: 2416
<212> TYPE: DNA
<213> ORGANISM: Saccharomyces cerevisiae
<220> FEATURE:
<221> NAME/KEY: CDS
<222> LOCATION: (501)..(1916)

<400> SEQUENCE: 53
ttcgcgctat ctcgatttct acctatatag ttaatctctg tacaaaaaca atctttccaa      60
ctatccatta atcatagtat attatcagcg tcggcgattt taccacgctt gacaaaagcc     120

```
gcgggcggga ttcctgtggg tagtggcacc ggcagttaat ctaatcaaag gcgcttgaag      180
gaagagatag ataatagaac aaagcaatcg ccgctttgga cggcaaatat gtttatccat      240
tggtgcggtg attggatatg atttgtctcc agtagtataa gcaagcgcca gatctgttta      300
ctgtaaaatt aagtgagtaa tctcgcggga tgtaatgatt taagggaatc tggttcaggt      360
tttcacatat atttgtatat aaggccattt gtaatttcaa tagttttagg attttttcctt     420 ctcccaaaat actcacttac tgtgttacat tacagaaaga acagacaaga aaccgtcaat      480
aagaaatata actaagaaca atg tct att tgt gaa caa tac tac cca gaa gag      533
                       Met Ser Ile Cys Glu Gln Tyr Tyr Pro Glu Glu
                        1               5                      10 cca acc aaa cca act gtt aag acc gag tcc att cct ggt cct gaa tcc      581
Pro Thr Lys Pro Thr Val Lys Thr Glu Ser Ile Pro Gly Pro Glu Ser
            15                  20                  25 cag aag cag tta aag gaa ctg ggt gaa gtt ttt gac aca aga cca gca      629
Gln Lys Gln Leu Lys Glu Leu Gly Glu Val Phe Asp Thr Arg Pro Ala
        30                  35                  40 tat ttt ttg gct gat tat gag aaa tct tta ggt aac tat atc act gat      677
Tyr Phe Leu Ala Asp Tyr Glu Lys Ser Leu Gly Asn Tyr Ile Thr Asp
    45                  50                  55 gtg gat ggg aac aca tat ttg gat ttg tat gcc caa atc tct tca att      725
Val Asp Gly Asn Thr Tyr Leu Asp Leu Tyr Ala Gln Ile Ser Ser Ile
60                  65                  70                  75 gca ctt ggt tat aac aac cct gct ttg atc aag gca gca caa tca cca      773
Ala Leu Gly Tyr Asn Asn Pro Ala Leu Ile Lys Ala Ala Gln Ser Pro
                80                  85                  90 gaa atg atc cgt gct ttg gtc gac cgt cct gcc tta ggt aac ttc cca      821
Glu Met Ile Arg Ala Leu Val Asp Arg Pro Ala Leu Gly Asn Phe Pro
            95                 100                 105 tct aag gat tta gac aag ata ttg aag caa ata ttg aaa tct gcg cca      869
Ser Lys Asp Leu Asp Lys Ile Leu Lys Gln Ile Leu Lys Ser Ala Pro
        110                 115                 120 aag ggt caa gat cac gtc tgg tca ggg ctt tcc ggt gca gat gcc aat      917
Lys Gly Gln Asp His Val Trp Ser Gly Leu Ser Gly Ala Asp Ala Asn
    125                 130                 135 gaa tta gcg ttc aag gct gcc ttt att tat tac cgt gcc aaa caa agg      965
Glu Leu Ala Phe Lys Ala Ala Phe Ile Tyr Tyr Arg Ala Lys Gln Arg
140                 145                 150                 155 ggc tat gat gcc gat ttt tct gaa aag gaa aac ttg tct gtc atg gac      1013
Gly Tyr Asp Ala Asp Phe Ser Glu Lys Glu Asn Leu Ser Val Met Asp
                160                 165                 170 aat gac gcc cct ggc gcc cct cat ctt gcc gta cta tcg ttc aag aga      1061
Asn Asp Ala Pro Gly Ala Pro His Leu Ala Val Leu Ser Phe Lys Arg
            175                 180                 185 gcg ttc cac ggt aga ttg ttt gcc tcc ggt tcc aca act tgt tct aaa      1109
Ala Phe His Gly Arg Leu Phe Ala Ser Gly Ser Thr Thr Cys Ser Lys
        190                 195                 200 cca att cac aag ttg gat ttc cca gcc ttc cac tgg cct cat gct gag      1157
Pro Ile His Lys Leu Asp Phe Pro Ala Phe His Trp Pro His Ala Glu
    205                 210                 215 tat cca tct tac caa tac cca tta gat gaa aat tct gat gca aac cgt      1205
Tyr Pro Ser Tyr Gln Tyr Pro Leu Asp Glu Asn Ser Asp Ala Asn Arg
220                 225                 230                 235 aaa gag gat gac cat tgc ttg gcc att gtt gaa gaa tta atc aaa acc      1253
Lys Glu Asp Asp His Cys Leu Ala Ile Val Glu Glu Leu Ile Lys Thr
                240                 245                 250 tgg tct att cca gtt gct gcc tta atc atc gaa cca att caa tct gag      1301
Trp Ser Ile Pro Val Ala Ala Leu Ile Ile Glu Pro Ile Gln Ser Glu
```

```
                   255                 260                 265
gga ggt gat aac cac gct tct aag tat ttc tta caa aag cta aga gac    1349
Gly Gly Asp Asn His Ala Ser Lys Tyr Phe Leu Gln Lys Leu Arg Asp
            270                 275                 280 att acc ttg aag tat aac gtt gtc tac atc ata gat gaa gtg caa aca    1397
Ile Thr Leu Lys Tyr Asn Val Val Tyr Ile Ile Asp Glu Val Gln Thr
        285                 290                 295 ggt gtc gga gcc acc ggt aag cta tgg tgt cat gag tac gcc gat att    1445
Gly Val Gly Ala Thr Gly Lys Leu Trp Cys His Glu Tyr Ala Asp Ile
300                 305                 310                 315 caa cca cct gtg gat tta gtg acc ttt tcc aag aaa ttc caa agt gca    1493
Gln Pro Pro Val Asp Leu Val Thr Phe Ser Lys Lys Phe Gln Ser Ala
                320                 325                 330 gga tat ttc ttc cac gac cct aaa ttc att cca aac aaa cca tac aga    1541
Gly Tyr Phe Phe His Asp Pro Lys Phe Ile Pro Asn Lys Pro Tyr Arg
            335                 340                 345 caa ttc aac aca tgg tgt ggt gaa cct gca aga atg atc att gca ggt    1589
Gln Phe Asn Thr Trp Cys Gly Glu Pro Ala Arg Met Ile Ile Ala Gly
        350                 355                 360 gcc att gga cag gaa atc tcc gac aag aag ttg act gaa caa tgt tca    1637
Ala Ile Gly Gln Glu Ile Ser Asp Lys Lys Leu Thr Glu Gln Cys Ser
365                 370                 375 aga gta ggt gat tat ttg ttc aag aaa ttg gag ggt ttg cag aag aaa    1685
Arg Val Gly Asp Tyr Leu Phe Lys Lys Leu Glu Gly Leu Gln Lys Lys
380                 385                 390                 395 tac cct gaa aac ttt caa aac ttg aga ggt aaa gga aga ggc aca ttc    1733
Tyr Pro Glu Asn Phe Gln Asn Leu Arg Gly Lys Gly Arg Gly Thr Phe
                400                 405                 410 att gcc tgg gat ttg cct act ggt gag aag aga gac tta cta ttg aag    1781
Ile Ala Trp Asp Leu Pro Thr Gly Glu Lys Arg Asp Leu Leu Leu Lys
            415                 420                 425 aaa ttg aag ttg aat ggt tgc aac gtt ggt gga tgt gca gtc cat gca    1829
Lys Leu Lys Leu Asn Gly Cys Asn Val Gly Gly Cys Ala Val His Ala
        430                 435                 440 gtg aga tta aga cct tca tta aca ttc gag gag aag cat gct gat atc    1877
Val Arg Leu Arg Pro Ser Leu Thr Phe Glu Glu Lys His Ala Asp Ile
445                 450                 455 ttt att gaa gca tta gcc aaa tca gtt aat gaa tta tga ttgtatatta    1926
Phe Ile Glu Ala Leu Ala Lys Ser Val Asn Glu Leu
460                 465                 470 gcgaggccgt gtcacgttcc cttttttggt ctttatatat gtgtatcttg ttataatttt    1986
aaagaaaagt tttatattac tcatcagttg tgtgtgaaaa atatgggcgg gtattcacaa    2046
taggaaaaaa aaaatgggtt tggtgactgc agtaaagacg tgctaaaaaa aaaaaagttg    2106
tttttatctg aaccttaaat atatcattta tgagtgtata tattatacaa acgcaataac    2166
agtggctccc gccctccacc tccgcctgct actagtaatc taccagtaat tgtgtttgtt    2226
ttgggaaaga tcgttcgctt actcaccgaa caactttctg actctcttca atacagagtc    2286
cttttcaggg tcgtagggat gatctttaga tggaattct aaaatagcag ggaacgcatt    2346
ggtgaaggag tccactctag ctcttatgtt ttccgcgata tgttggttga ttagaaggat    2406
ggcaatatcg                                                           2416

<210> SEQ ID NO 54
<211> LENGTH: 471
<212> TYPE: PRT
<213> ORGANISM: Saccharomyces cerevisiae

<400> SEQUENCE: 54
```

-continued

```
Met Ser Ile Cys Glu Gln Tyr Pro Glu Pro Thr Lys Pro Thr
1               5                   10                  15

Val Lys Thr Glu Ser Ile Pro Gly Pro Glu Ser Gln Lys Gln Leu Lys
            20                  25                  30

Glu Leu Gly Glu Val Phe Asp Thr Arg Pro Ala Tyr Phe Leu Ala Asp
            35                  40                  45

Tyr Glu Lys Ser Leu Gly Asn Tyr Ile Thr Asp Val Asp Gly Asn Thr
50                  55                  60

Tyr Leu Asp Leu Tyr Ala Gln Ile Ser Ser Ile Ala Leu Gly Tyr Asn
65                  70                  75                  80

Asn Pro Ala Leu Ile Lys Ala Ala Gln Ser Pro Glu Met Ile Arg Ala
                85                  90                  95

Leu Val Asp Arg Pro Ala Leu Gly Asn Phe Pro Ser Lys Asp Leu Asp
                100                 105                 110

Lys Ile Leu Lys Gln Ile Leu Lys Ser Ala Pro Lys Gly Gln Asp His
                115                 120                 125

Val Trp Ser Gly Leu Ser Gly Ala Asp Ala Asn Glu Leu Ala Phe Lys
            130                 135                 140

Ala Ala Phe Ile Tyr Tyr Arg Ala Lys Gln Arg Gly Tyr Asp Ala Asp
145                 150                 155                 160

Phe Ser Glu Lys Glu Asn Leu Ser Val Met Asp Asn Asp Ala Pro Gly
                165                 170                 175

Ala Pro His Leu Ala Val Leu Ser Phe Lys Arg Ala Phe His Gly Arg
                180                 185                 190

Leu Phe Ala Ser Gly Ser Thr Thr Cys Ser Lys Pro Ile His Lys Leu
                195                 200                 205

Asp Phe Pro Ala Phe His Trp Pro His Ala Glu Tyr Pro Ser Tyr Gln
            210                 215                 220

Tyr Pro Leu Asp Glu Asn Ser Asp Ala Asn Arg Lys Glu Asp Asp His
225                 230                 235                 240

Cys Leu Ala Ile Val Glu Glu Leu Ile Lys Thr Trp Ser Ile Pro Val
                245                 250                 255

Ala Ala Leu Ile Ile Glu Pro Ile Gln Ser Gly Gly Asp Asn His
                260                 265                 270

Ala Ser Lys Tyr Phe Leu Gln Lys Leu Arg Asp Ile Thr Leu Lys Tyr
            275                 280                 285

Asn Val Val Tyr Ile Ile Asp Glu Val Gln Thr Gly Val Gly Ala Thr
            290                 295                 300

Gly Lys Leu Trp Cys His Glu Tyr Ala Asp Ile Gln Pro Pro Val Asp
305                 310                 315                 320

Leu Val Thr Phe Ser Lys Lys Phe Gln Ser Ala Gly Tyr Phe Phe His
                325                 330                 335

Asp Pro Lys Phe Ile Pro Asn Lys Pro Tyr Arg Gln Phe Asn Thr Trp
                340                 345                 350

Cys Gly Glu Pro Ala Arg Met Ile Ala Gly Ala Ile Gly Gln Glu
            355                 360                 365

Ile Ser Asp Lys Lys Leu Thr Glu Gln Cys Ser Arg Val Gly Asp Tyr
            370                 375                 380

Leu Phe Lys Lys Leu Glu Gly Leu Gln Lys Lys Tyr Pro Glu Asn Phe
385                 390                 395                 400

Gln Asn Leu Arg Gly Lys Gly Arg Gly Thr Phe Ile Ala Trp Asp Leu
                405                 410                 415
```

```
Pro Thr Gly Glu Lys Arg Asp Leu Leu Leu Lys Lys Leu Lys Leu Asn
            420                 425                 430
Gly Cys Asn Val Gly Cys Ala Val His Ala Val Arg Leu Arg Pro
        435                 440                 445
Ser Leu Thr Phe Glu Glu Lys His Ala Asp Ile Phe Ile Glu Ala Leu
    450                 455                 460
Ala Lys Ser Val Asn Glu Leu
465                 470

<210> SEQ ID NO 55
<211> LENGTH: 25
<212> TYPE: DNA
<213> ORGANISM: Artificial Sequence
<220> FEATURE:
<223> OTHER INFORMATION: primer

<400> SEQUENCE: 55
ataaagctta accagcgaga tgtcg                                        25

<210> SEQ ID NO 56
<211> LENGTH: 26
<212> TYPE: DNA
<213> ORGANISM: Artificial Sequence
<220> FEATURE:
<223> OTHER INFORMATION: primer

<400> SEQUENCE: 56
ctctctagag ggcaaattga tgcttc                                       26

<210> SEQ ID NO 57
<211> LENGTH: 1083
<212> TYPE: DNA
<213> ORGANISM: Saccharomyces cerevisiae
<220> FEATURE:
<221> NAME/KEY: CDS
<222> LOCATION: (1)..(1083)

<400> SEQUENCE: 57 atg tcg ata gtc tac aat aaa aca cca tta tta cgt caa ttc ttc ccc    48
Met Ser Ile Val Tyr Asn Lys Thr Pro Leu Leu Arg Gln Phe Phe Pro
1               5                   10                  15 gga aag gct tct gca caa ttt ttc ttg aaa tat gaa tgc ctt caa cca    96
Gly Lys Ala Ser Ala Gln Phe Phe Leu Lys Tyr Glu Cys Leu Gln Pro
            20                  25                  30 agt ggc tcc ttc aaa agt aga gga atc ggt aat ctc atc atg aaa agt   144
Ser Gly Ser Phe Lys Ser Arg Gly Ile Gly Asn Leu Ile Met Lys Ser
        35                  40                  45 gcc att cga att caa aag gac ggt aaa aga tct cct cag gtt ttc gct   192
Ala Ile Arg Ile Gln Lys Asp Gly Lys Arg Ser Pro Gln Val Phe Ala
    50                  55                  60 agt tct ggc ggt aat gcc ggt ttt gct gct gca aca gca tgt caa aga   240
Ser Ser Gly Gly Asn Ala Gly Phe Ala Ala Ala Thr Ala Cys Gln Arg
65                  70                  75                  80 ctg tct cta cca tgt aca gtc gtg gtt cct aca gcg aca aag aag aga   288
Leu Ser Leu Pro Cys Thr Val Val Val Pro Thr Ala Thr Lys Lys Arg
                85                  90                  95 atg gta gat aaa atc agg aac acc ggt gcc cag gtt atc gtg agt ggt   336
Met Val Asp Lys Ile Arg Asn Thr Gly Ala Gln Val Ile Val Ser Gly
            100                 105                 110 gcc tac tgg aaa gaa gca gat act ttt tta aaa aca aat gtc atg aat   384
Ala Tyr Trp Lys Glu Ala Asp Thr Phe Leu Lys Thr Asn Val Met Asn
        115                 120                 125
```

| | | |
|---|---|---|
| aaa ata gac tct cag gtc att gag ccc att tat gtt cat ccc ttc gat<br>Lys Ile Asp Ser Gln Val Ile Glu Pro Ile Tyr Val His Pro Phe Asp<br>130                      135                      140 | | 432 |
| aat ccg gat att tgg gaa gga cat tca tct atg ata gat gaa ata gta<br>Asn Pro Asp Ile Trp Glu Gly His Ser Ser Met Ile Asp Glu Ile Val<br>145                  150                    155                    160 | | 480 |
| caa gat ttg aaa tcg caa cat att tcc gtg aat aag gtt aaa ggc ata<br>Gln Asp Leu Lys Ser Gln His Ile Ser Val Asn Lys Val Lys Gly Ile<br>                    165                    170                    175 | | 528 |
| gta tgc agc gtt ggt gga ggt ggt tta tac aat ggt att att caa ggt<br>Val Cys Ser Val Gly Gly Gly Gly Leu Tyr Asn Gly Ile Ile Gln Gly<br>                  180                    185                    190 | | 576 |
| ttg gaa agg tat ggt tta gct gat agg atc cct att gtg ggg gtg gaa<br>Leu Glu Arg Tyr Gly Leu Ala Asp Arg Ile Pro Ile Val Gly Val Glu<br>                    195                    200                    205 | | 624 |
| acg aat gga tgt cat gtt ttc aat act tct ttg aaa ata ggc caa cca<br>Thr Asn Gly Cys His Val Phe Asn Thr Ser Leu Lys Ile Gly Gln Pro<br>210                      215                    220 | | 672 |
| gtt caa ttc aag aag ata aca agt att gct act tct cta gga acg gcc<br>Val Gln Phe Lys Lys Ile Thr Ser Ile Ala Thr Ser Leu Gly Thr Ala<br>225                  230                    235                    240 | | 720 |
| gtg atc tct aat caa act ttc gaa tac gct cgc aaa tac aac acc aga<br>Val Ile Ser Asn Gln Thr Phe Glu Tyr Ala Arg Lys Tyr Asn Thr Arg<br>                    245                    250                    255 | | 768 |
| tcc gtt gta ata gag gac aaa gat gtt att gaa acc tgt ctt aaa tat<br>Ser Val Val Ile Glu Asp Lys Asp Val Ile Glu Thr Cys Leu Lys Tyr<br>                  260                    265                    270 | | 816 |
| aca cat caa ttc aat atg gtg att gaa ccg gca tgt ggc gcc gca ttg<br>Thr His Gln Phe Asn Met Val Ile Glu Pro Ala Cys Gly Ala Ala Leu<br>                  275                    280                    285 | | 864 |
| cat ttg ggt tac aac act aag atc cta gaa aat gca ctg ggc tca aaa<br>His Leu Gly Tyr Asn Thr Lys Ile Leu Glu Asn Ala Leu Gly Ser Lys<br>                  290                    295                    300 | | 912 |
| tta gct gcg gat gac att gtg ata att att gct tgt ggc ggc tcc tct<br>Leu Ala Ala Asp Asp Ile Val Ile Ile Ile Ala Cys Gly Gly Ser Ser<br>305                  310                    315                    320 | | 960 |
| aat act ata aag gac ttg gaa gaa gcg ttg gat agc atg aga aaa aaa<br>Asn Thr Ile Lys Asp Leu Glu Glu Ala Leu Asp Ser Met Arg Lys Lys<br>                  325                    330                    335 | | 1008 |
| gac act cct gta ata gaa gtc gct gac aat ttc ata ttt cca gaa aaa<br>Asp Thr Pro Val Ile Glu Val Ala Asp Asn Phe Ile Phe Pro Glu Lys<br>                  340                    345                    350 | | 1056 |
| aat att gtg aat tta aaa agt gct tga<br>Asn Ile Val Asn Leu Lys Ser Ala<br>                  355                    360 | | 1083 |

<210> SEQ ID NO 58
<211> LENGTH: 360
<212> TYPE: PRT
<213> ORGANISM: Saccharomyces cerevisiae

<400> SEQUENCE: 58

Met Ser Ile Val Tyr Asn Lys Thr Pro Leu Leu Arg Gln Phe Phe Pro
1                  5                        10                        15

Gly Lys Ala Ser Ala Gln Phe Phe Leu Lys Tyr Glu Cys Leu Gln Pro
                    20                        25                        30

Ser Gly Ser Phe Lys Ser Arg Gly Ile Gly Asn Leu Ile Met Lys Ser
                        35                        40                        45

Ala Ile Arg Ile Gln Lys Asp Gly Lys Arg Ser Pro Gln Val Phe Ala
                  50                        55                        60

Ser Ser Gly Gly Asn Ala Gly Phe Ala Ala Ala Thr Ala Cys Gln Arg
65                  70                  75                  80

Leu Ser Leu Pro Cys Thr Val Val Pro Thr Ala Thr Lys Lys Arg
            85                  90                  95

Met Val Asp Lys Ile Arg Asn Thr Gly Ala Gln Val Ile Val Ser Gly
            100                 105                 110

Ala Tyr Trp Lys Glu Ala Asp Thr Phe Leu Lys Thr Asn Val Met Asn
            115                 120                 125

Lys Ile Asp Ser Gln Val Ile Glu Pro Ile Tyr Val His Pro Phe Asp
130                 135                 140

Asn Pro Asp Ile Trp Glu Gly His Ser Ser Met Ile Asp Glu Ile Val
145                 150                 155                 160

Gln Asp Leu Lys Ser Gln His Ile Ser Val Asn Lys Val Lys Gly Ile
                165                 170                 175

Val Cys Ser Val Gly Gly Gly Leu Tyr Asn Gly Ile Ile Gln Gly
            180                 185                 190

Leu Glu Arg Tyr Gly Leu Ala Asp Arg Ile Pro Ile Val Gly Val Glu
            195                 200                 205

Thr Asn Gly Cys His Val Phe Asn Thr Ser Leu Lys Ile Gly Gln Pro
210                 215                 220

Val Gln Phe Lys Lys Ile Thr Ser Ile Ala Thr Ser Leu Gly Thr Ala
225                 230                 235                 240

Val Ile Ser Asn Gln Thr Phe Glu Tyr Ala Arg Lys Tyr Asn Thr Arg
                245                 250                 255

Ser Val Val Ile Glu Asp Lys Asp Val Ile Glu Thr Cys Leu Lys Tyr
            260                 265                 270

Thr His Gln Phe Asn Met Val Ile Glu Pro Ala Cys Gly Ala Ala Leu
            275                 280                 285

His Leu Gly Tyr Asn Thr Lys Ile Leu Glu Asn Ala Leu Gly Ser Lys
        290                 295                 300

Leu Ala Ala Asp Asp Ile Val Ile Ile Ala Cys Gly Gly Ser Ser
305                 310                 315                 320

Asn Thr Ile Lys Asp Leu Glu Glu Ala Leu Asp Ser Met Arg Lys Lys
                325                 330                 335

Asp Thr Pro Val Ile Glu Val Ala Asp Asn Phe Ile Phe Pro Glu Lys
            340                 345                 350

Asn Ile Val Asn Leu Lys Ser Ala
        355                 360

<210> SEQ ID NO 59
<211> LENGTH: 100
<212> TYPE: DNA
<213> ORGANISM: Artificial Sequence
<220> FEATURE:
<223> OTHER INFORMATION: primer

<400> SEQUENCE: 59
gccaggcggt tgatactttg tgcagatttc ataccggctg tcgctattat tactgatgaa    60
ttggctctct ttttgtttaa tcttaaccca actgcacaga                         100

<210> SEQ ID NO 60
<211> LENGTH: 100
<212> TYPE: DNA
<213> ORGANISM: Artificial Sequence
<220> FEATURE:
<223> OTHER INFORMATION: primer

<400> SEQUENCE: 60
ttggatgcat ctaatggggc accagtagcg agtgttctga tggagaattt ccccaacttc    60
aaggaatgtc tctgcaacat tgttttatat ttgttgtaaa    100

<210> SEQ ID NO 61
<211> LENGTH: 2637
<212> TYPE: DNA
<213> ORGANISM: Saccharomyces cerevisiae
<220> FEATURE:
<221> NAME/KEY: CDS
<222> LOCATION: (1)..(2637)

<400> SEQUENCE: 61

| | | | | | | | | | | | | | | | | |
|---|---|---|---|---|---|---|---|---|---|---|---|---|---|---|---|---|
| atg | tac | gat | agc | agg | ggt | gtc | gca | ttg | cac | tct | gaa | cta | att | cat | agg | 48 |
| Met | Tyr | Asp | Ser | Arg | Gly | Val | Ala | Leu | His | Ser | Glu | Leu | Ile | His | Arg | |
| 1 | | | | 5 | | | | | 10 | | | | | 15 | | |
| tgg | aat | cac | gct | ttt | tcc | atc | tta | tcc | att | gtt | gca | ttt | cca | aaa | aaa | 96 |
| Trp | Asn | His | Ala | Phe | Ser | Ile | Leu | Ser | Ile | Val | Ala | Phe | Pro | Lys | Lys | |
| | | | 20 | | | | | 25 | | | | | 30 | | | |
| aga | ttg | ttg | ttt | gct | ggt | agc | caa | gac | tcc | aag | ata | ttg | gtt | ttt | gat | 144 |
| Arg | Leu | Leu | Phe | Ala | Gly | Ser | Gln | Asp | Ser | Lys | Ile | Leu | Val | Phe | Asp | |
| | 35 | | | | | 40 | | | | | 45 | | | | | |
| ctt | ccc | aca | tat | aat | cta | ata | cat | acg | att | aga | cta | ggc | gaa | tca | caa | 192 |
| Leu | Pro | Thr | Tyr | Asn | Leu | Ile | His | Thr | Ile | Arg | Leu | Gly | Glu | Ser | Gln | |
| 50 | | | | | 55 | | | | | 60 | | | | | | |
| gag | gaa | acg | cat | acc | aga | tct | tcg | gtt | ttg | tgc | tta | aca | gga | tca | gaa | 240 |
| Glu | Glu | Thr | His | Thr | Arg | Ser | Ser | Val | Leu | Cys | Leu | Thr | Gly | Ser | Glu | |
| 65 | | | | | 70 | | | | | 75 | | | | | 80 | |
| gat | gaa | aac | ttt | tta | ttt | tca | ggc | ggc | gca | gat | tct | ttg | gtg | aga | att | 288 |
| Asp | Glu | Asn | Phe | Leu | Phe | Ser | Gly | Gly | Ala | Asp | Ser | Leu | Val | Arg | Ile | |
| | | | | 85 | | | | | 90 | | | | | 95 | | |
| tgg | tcc | att | ggc | gaa | aag | acc | att | aga | gat | gac | ttt | cta | cct | gtt | act | 336 |
| Trp | Ser | Ile | Gly | Glu | Lys | Thr | Ile | Arg | Asp | Asp | Phe | Leu | Pro | Val | Thr | |
| | | | 100 | | | | | 105 | | | | | 110 | | | |
| gaa | ata | gcc | act | gtt | tac | tca | gtg | acc | gat | att | ggt | gat | att | ttc | tca | 384 |
| Glu | Ile | Ala | Thr | Val | Tyr | Ser | Val | Thr | Asp | Ile | Gly | Asp | Ile | Phe | Ser | |
| | 115 | | | | | 120 | | | | | 125 | | | | | |
| ttg | gca | tat | ttg | gat | tcg | ttg | gaa | act | att | gtc | ttt | ggc | tgt | caa | aat | 432 |
| Leu | Ala | Tyr | Leu | Asp | Ser | Leu | Glu | Thr | Ile | Val | Phe | Gly | Cys | Gln | Asn | |
| 130 | | | | | 135 | | | | | 140 | | | | | | |
| gca | agc | tta | cta | tat | gtt | gag | aac | ttg | att | cag | aag | att | gaa | aaa | aaa | 480 |
| Ala | Ser | Leu | Leu | Tyr | Val | Glu | Asn | Leu | Ile | Gln | Lys | Ile | Glu | Lys | Lys | |
| 145 | | | | | 150 | | | | | 155 | | | | | 160 | |
| tcc | tct | gat | gga | gta | gaa | aat | atc | aat | aaa | tta | ccg | cat | aga | aga | tat | 528 |
| Ser | Ser | Asp | Gly | Val | Glu | Asn | Ile | Asn | Lys | Leu | Pro | His | Arg | Arg | Tyr | |
| | | | | 165 | | | | | 170 | | | | | 175 | | |
| gat | aag | ttc | ttt | gat | tcg | tta | ggt | ccg | act | gga | tat | agt | tca | aat | tca | 576 |
| Asp | Lys | Phe | Phe | Asp | Ser | Leu | Gly | Pro | Thr | Gly | Tyr | Ser | Ser | Asn | Ser | |
| | | | 180 | | | | | 185 | | | | | 190 | | | |
| tta | tct | caa | act | tca | ttg | acc | tct | cta | caa | gaa | aac | tgt | ggc | gct | gcc | 624 |
| Leu | Ser | Gln | Thr | Ser | Leu | Thr | Ser | Leu | Gln | Glu | Asn | Cys | Gly | Ala | Ala | |
| | 195 | | | | | 200 | | | | | 205 | | | | | |
| atc | ata | gag | gtt | ccc | tcc | gaa | aac | att | att | aaa | tat | gca | cat | tat | ggg | 672 |
| Ile | Ile | Glu | Val | Pro | Ser | Glu | Asn | Ile | Ile | Lys | Tyr | Ala | His | Tyr | Gly | |
| 210 | | | | | 215 | | | | | 220 | | | | | | |
| ttt | att | tat | tct | att | aat | aaa | ttg | tgt | ccc | agg | ttt | aat | cag | tta | ttg | 720 |
| Phe | Ile | Tyr | Ser | Ile | Asn | Lys | Leu | Cys | Pro | Arg | Phe | Asn | Gln | Leu | Leu | |
| 225 | | | | | 230 | | | | | 235 | | | | | 240 | |
| gaa | aaa | agc | tca | cga | act | tct | ggt | gca | gag | cac | ata | att | tca | tcc | gct | 768 |

```
      Glu Lys Ser Ser Arg Thr Ser Gly Ala Glu His Ile Ile Ser Ser Ala
                      245                 250                 255 ggt gat gga ata agc aag ctt tgg gag ttc tct aaa gat aaa ggg caa          816
Gly Asp Gly Ile Ser Lys Leu Trp Glu Phe Ser Lys Asp Lys Gly Gln
            260                 265                 270 aac act gtt aaa atc tcc ttg ata aac gat aaa atc gac aat gaa gat          864
Asn Thr Val Lys Ile Ser Leu Ile Asn Asp Lys Ile Asp Asn Glu Asp
                275                 280                 285 agc gtc ata tcc caa act att gag ttc cca ttt tta tat tgc ggg ttg          912
Ser Val Ile Ser Gln Thr Ile Glu Phe Pro Phe Leu Tyr Cys Gly Leu
            290                 295                 300 act gac ggg att ata aaa atc tgg gac tta aat act cag caa ata atc          960
Thr Asp Gly Ile Ile Lys Ile Trp Asp Leu Asn Thr Gln Gln Ile Ile
305                 310                 315                 320 tca act ctg aaa aca aag cat gaa tcg gac gtc att tca ata tca gtt         1008
Ser Thr Leu Lys Thr Lys His Glu Ser Asp Val Ile Ser Ile Ser Val
                325                 330                 335 tat atg gac cat gta ttt gcc att gat gaa tca ggc atc acg cat ttt         1056
Tyr Met Asp His Val Phe Ala Ile Asp Glu Ser Gly Ile Thr His Phe
            340                 345                 350 tac cag aac caa gtt aac cat tgg aac cct caa caa gga aaa ata tta         1104
Tyr Gln Asn Gln Val Asn His Trp Asn Pro Gln Gln Gly Lys Ile Leu
        355                 360                 365 agc tca gag att ttc agt aaa tca aat gct gga tct gtt agt tta tta         1152
Ser Ser Glu Ile Phe Ser Lys Ser Asn Ala Gly Ser Val Ser Leu Leu
370                 375                 380 acg ggt ggt agc gat ggg tca ttg act ctc tgg gat ata acc tca tta         1200
Thr Gly Gly Ser Asp Gly Ser Leu Thr Leu Trp Asp Ile Thr Ser Leu
385                 390                 395                 400 tta tct gcg gtg cct ctg tca agc aac tca ccc atc aat gca tca tct         1248
Leu Ser Ala Val Pro Leu Ser Ser Asn Ser Pro Ile Asn Ala Ser Ser
                405                 410                 415 aca tta caa acc acc aat tta tgg gcc gcc tat caa tct gcc tct cta         1296
Thr Leu Gln Thr Thr Asn Leu Trp Ala Ala Tyr Gln Ser Ala Ser Leu
            420                 425                 430 aat aac gag gag atg tta aac aca ctg aga gaa ctt att tct ttc cag         1344
Asn Asn Glu Glu Met Leu Asn Thr Leu Arg Glu Leu Ile Ser Phe Gln
        435                 440                 445 aca gtg tct caa agc aaa gac act act aat act ttg tca tta agg cgt         1392
Thr Val Ser Gln Ser Lys Asp Thr Thr Asn Thr Leu Ser Leu Arg Arg
450                 455                 460 tgt gca atc tac ctg caa caa tta ttc ttg aag ttt gga gct aca aac         1440
Cys Ala Ile Tyr Leu Gln Gln Leu Phe Leu Lys Phe Gly Ala Thr Asn
465                 470                 475                 480 tcc caa tta ttt cca ttg cct gat ggt ggt aat cct gtt gta ttc gca         1488
Ser Gln Leu Phe Pro Leu Pro Asp Gly Gly Asn Pro Val Val Phe Ala
                485                 490                 495 tat ttt caa ggg aat ggg aaa gtt tca cag gtg aag ggt gcc aag aaa         1536
Tyr Phe Gln Gly Asn Gly Lys Val Ser Gln Val Lys Gly Ala Lys Lys
            500                 505                 510 aag cgt att cta tgg tat ggg cat tat gac gtt ata tcg tct gga aat         1584
Lys Arg Ile Leu Trp Tyr Gly His Tyr Asp Val Ile Ser Ser Gly Asn
        515                 520                 525 act ttc aac tgg aat acc gac cca ttt act tta act tgt gaa aac gga         1632
Thr Phe Asn Trp Asn Thr Asp Pro Phe Thr Leu Thr Cys Glu Asn Gly
530                 535                 540 tac tta aaa ggt cga gga gta tca gat aat aaa ggg cca ttg gtg agc         1680
Tyr Leu Lys Gly Arg Gly Val Ser Asp Asn Lys Gly Pro Leu Val Ser
545                 550                 555                 560
```

```
                                                    -continued gct att cat agt gtg gcg tat ttg ttt caa cag gga gaa ttg gtg aac     1728
Ala Ile His Ser Val Ala Tyr Leu Phe Gln Gln Gly Glu Leu Val Asn
            565                 570                 575 gat gtc gta ttt ttg gtg gaa gga agt gaa gaa atc gga tct gct agt     1776
Asp Val Val Phe Leu Val Glu Gly Ser Glu Glu Ile Gly Ser Ala Ser
        580                 585                 590 ttg aag caa gtt tgt gaa aag tac cat gat att att gga aaa gat att     1824
Leu Lys Gln Val Cys Glu Lys Tyr His Asp Ile Ile Gly Lys Asp Ile
    595                 600                 605 gac tgg att tta tta agt aat tct act tgg gtt gat caa gaa cat cca     1872
Asp Trp Ile Leu Leu Ser Asn Ser Thr Trp Val Asp Gln Glu His Pro
610                 615                 620 tgc ttg aat tat gga ttg aga ggt gtt att aat gcc caa ata aaa gtc     1920
Cys Leu Asn Tyr Gly Leu Arg Gly Val Ile Asn Ala Gln Ile Lys Val
625                 630                 635                 640 tgg agc gat aag cct gac gga cat tct ggt ctt aac ggt ggt gtt tat     1968
Trp Ser Asp Lys Pro Asp Gly His Ser Gly Leu Asn Gly Gly Val Tyr
        645                 650                 655 gat gaa cct atg gtt aat tta gtg aaa atc gtg tcc aaa cta caa aac     2016
Asp Glu Pro Met Val Asn Leu Val Lys Ile Val Ser Lys Leu Gln Asn
    660                 665                 670 gaa caa aat gaa att atg att cca aat ttt tat tca cca ttg aaa gat     2064
Glu Gln Asn Glu Ile Met Ile Pro Asn Phe Tyr Ser Pro Leu Lys Asp
675                 680                 685 ctg act gaa gaa gaa tat caa agg ttt cag aaa att acc gag ctt gca     2112
Leu Thr Glu Glu Glu Tyr Gln Arg Phe Gln Lys Ile Thr Glu Leu Ala
690                 695                 700 aat atc gac gaa aat act act gtt caa gat tta att acc aac tgg act     2160
Asn Ile Asp Glu Asn Thr Thr Val Gln Asp Leu Ile Thr Asn Trp Thr
705                 710                 715                 720 aag cct tcc ttg tct atg aca aca gtc aag ttt agc ggt cct ggt aac     2208
Lys Pro Ser Leu Ser Met Thr Thr Val Lys Phe Ser Gly Pro Gly Asn
            725                 730                 735 ata aca gtt att cca aaa agt gtc acc atg ggt atc tcc atc agg tta     2256
Ile Thr Val Ile Pro Lys Ser Val Thr Met Gly Ile Ser Ile Arg Leu
        740                 745                 750 gta cct gag caa agt gta gaa caa gtc aag aga gat ctc aaa gcg tat     2304
Val Pro Glu Gln Ser Val Glu Gln Val Lys Arg Asp Leu Lys Ala Tyr
    755                 760                 765 tta gaa gaa agt ttc aag caa ttg aaa tct caa aat cat cta gaa att     2352
Leu Glu Glu Ser Phe Lys Gln Leu Lys Ser Gln Asn His Leu Glu Ile
770                 775                 780 aaa gtt tta aac gaa gca gaa ggt tgg ttg ggt gac cca aca aat cat     2400
Lys Val Leu Asn Glu Ala Glu Gly Trp Leu Gly Asp Pro Thr Asn His
785                 790                 795                 800 gca tac caa ata tta aag gac gaa att act act gca tgg gac gta gaa     2448
Ala Tyr Gln Ile Leu Lys Asp Glu Ile Thr Thr Ala Trp Asp Val Glu
            805                 810                 815 cca ttg cta gta aga gaa gga ggt tct att tca tgt ttg aga atg ttg     2496
Pro Leu Leu Val Arg Glu Gly Gly Ser Ile Ser Cys Leu Arg Met Leu
        820                 825                 830 gaa aga ata ttc gac gcg cca gct gtt caa ata cca tgt ggc caa tcc     2544
Glu Arg Ile Phe Asp Ala Pro Ala Val Gln Ile Pro Cys Gly Gln Ser
    835                 840                 845 act gac aat ggc cat tta gcc aac gaa aat ctc aga atc aaa aat tgg     2592
Thr Asp Asn Gly His Leu Ala Asn Glu Asn Leu Arg Ile Lys Asn Trp
850                 855                 860 tct aat ttg act gag att ttg tct aaa gta ttc aat agg tta taa        2637
Ser Asn Leu Thr Glu Ile Leu Ser Lys Val Phe Asn Arg Leu
865                 870                 875
```

<210> SEQ ID NO 62
<211> LENGTH: 878
<212> TYPE: PRT
<213> ORGANISM: Saccharomyces cerevisiae

<400> SEQUENCE: 62

Met Tyr Asp Ser Arg Gly Val Ala Leu His Ser Glu Leu Ile His Arg
1               5                   10                  15

Trp Asn His Ala Phe Ser Ile Leu Ser Ile Val Ala Phe Pro Lys Lys
            20                  25                  30

Arg Leu Leu Phe Ala Gly Ser Gln Asp Ser Lys Ile Leu Val Phe Asp
        35                  40                  45

Leu Pro Thr Tyr Asn Leu Ile His Thr Ile Arg Leu Gly Glu Ser Gln
    50                  55                  60

Glu Glu Thr His Thr Arg Ser Ser Val Leu Cys Leu Thr Gly Ser Glu
65                  70                  75                  80

Asp Glu Asn Phe Leu Phe Ser Gly Gly Ala Asp Ser Leu Val Arg Ile
                85                  90                  95

Trp Ser Ile Gly Glu Lys Thr Ile Arg Asp Asp Phe Leu Pro Val Thr
            100                 105                 110

Glu Ile Ala Thr Val Tyr Ser Val Thr Asp Ile Gly Asp Ile Phe Ser
        115                 120                 125

Leu Ala Tyr Leu Asp Ser Leu Glu Thr Ile Val Phe Gly Cys Gln Asn
    130                 135                 140

Ala Ser Leu Leu Tyr Val Glu Asn Leu Ile Gln Lys Ile Glu Lys Lys
145                 150                 155                 160

Ser Ser Asp Gly Val Glu Asn Ile Asn Lys Leu Pro His Arg Arg Tyr
                165                 170                 175

Asp Lys Phe Phe Asp Ser Leu Gly Pro Thr Gly Tyr Ser Ser Asn Ser
            180                 185                 190

Leu Ser Gln Thr Ser Leu Thr Ser Leu Gln Glu Asn Cys Gly Ala Ala
        195                 200                 205

Ile Ile Glu Val Pro Ser Glu Asn Ile Ile Lys Tyr Ala His Tyr Gly
    210                 215                 220

Phe Ile Tyr Ser Ile Asn Lys Leu Cys Pro Arg Phe Asn Gln Leu Leu
225                 230                 235                 240

Glu Lys Ser Ser Arg Thr Ser Gly Ala Glu His Ile Ile Ser Ser Ala
                245                 250                 255

Gly Asp Gly Ile Ser Lys Leu Trp Glu Phe Ser Lys Asp Lys Gly Gln
            260                 265                 270

Asn Thr Val Lys Ile Ser Leu Ile Asn Asp Lys Ile Asp Asn Glu Asp
        275                 280                 285

Ser Val Ile Ser Gln Thr Ile Glu Phe Pro Phe Leu Tyr Cys Gly Leu
    290                 295                 300

Thr Asp Gly Ile Ile Lys Ile Trp Asp Leu Asn Thr Gln Gln Ile Ile
305                 310                 315                 320

Ser Thr Leu Lys Thr Lys His Glu Ser Asp Val Ile Ser Ile Ser Val
                325                 330                 335

Tyr Met Asp His Val Phe Ala Ile Asp Glu Ser Gly Ile Thr His Phe
            340                 345                 350

Tyr Gln Asn Gln Val Asn His Trp Asn Pro Gln Gln Gly Lys Ile Leu
        355                 360                 365

Ser Ser Glu Ile Phe Ser Lys Ser Asn Ala Gly Ser Val Ser Leu Leu

-continued

```
            370                 375                 380
Thr Gly Ser Asp Gly Ser Leu Thr Leu Trp Asp Ile Thr Ser Leu
385                 390                 395                 400

Leu Ser Ala Val Pro Leu Ser Ser Asn Ser Pro Ile Asn Ala Ser Ser
                405                 410                 415

Thr Leu Gln Thr Thr Asn Leu Trp Ala Ala Tyr Gln Ser Ala Ser Leu
            420                 425                 430

Asn Asn Glu Glu Met Leu Asn Thr Leu Arg Glu Leu Ile Ser Phe Gln
                435                 440                 445

Thr Val Ser Gln Ser Lys Asp Thr Thr Asn Thr Leu Ser Leu Arg Arg
            450                 455                 460

Cys Ala Ile Tyr Leu Gln Gln Leu Phe Leu Lys Phe Gly Ala Thr Asn
465                 470                 475                 480

Ser Gln Leu Phe Pro Leu Pro Asp Gly Gly Asn Pro Val Val Phe Ala
                485                 490                 495

Tyr Phe Gln Gly Asn Gly Lys Val Ser Gln Val Lys Gly Ala Lys Lys
                500                 505                 510

Lys Arg Ile Leu Trp Tyr Gly His Tyr Asp Val Ile Ser Ser Gly Asn
            515                 520                 525

Thr Phe Asn Trp Asn Thr Asp Pro Phe Thr Leu Thr Cys Glu Asn Gly
            530                 535                 540

Tyr Leu Lys Gly Arg Gly Val Ser Asp Asn Lys Gly Pro Leu Val Ser
545                 550                 555                 560

Ala Ile His Ser Val Ala Tyr Leu Phe Gln Gln Gly Glu Leu Val Asn
                565                 570                 575

Asp Val Val Phe Leu Val Glu Gly Ser Glu Glu Ile Gly Ser Ala Ser
                580                 585                 590

Leu Lys Gln Val Cys Glu Lys Tyr His Asp Ile Ile Gly Lys Asp Ile
            595                 600                 605

Asp Trp Ile Leu Leu Ser Asn Ser Thr Trp Val Asp Gln Glu His Pro
            610                 615                 620

Cys Leu Asn Tyr Gly Leu Arg Gly Val Ile Asn Ala Gln Ile Lys Val
625                 630                 635                 640

Trp Ser Asp Lys Pro Asp Gly His Ser Gly Leu Asn Gly Val Tyr
                645                 650                 655

Asp Glu Pro Met Val Asn Leu Val Lys Ile Val Ser Lys Leu Gln Asn
                660                 665                 670

Glu Gln Asn Glu Ile Met Ile Pro Asn Phe Tyr Ser Pro Leu Lys Asp
            675                 680                 685

Leu Thr Glu Glu Glu Tyr Gln Arg Phe Gln Lys Ile Thr Glu Leu Ala
            690                 695                 700

Asn Ile Asp Glu Asn Thr Val Gln Asp Leu Ile Thr Asn Trp Thr
705                 710                 715                 720

Lys Pro Ser Leu Ser Met Thr Thr Val Lys Phe Ser Gly Pro Gly Asn
                725                 730                 735

Ile Thr Val Ile Pro Lys Ser Val Thr Met Gly Ile Ser Ile Arg Leu
                740                 745                 750

Val Pro Glu Gln Ser Val Glu Gln Val Lys Arg Asp Leu Lys Ala Tyr
                755                 760                 765

Leu Glu Glu Ser Phe Lys Gln Leu Lys Ser Gln Asn His Leu Glu Ile
            770                 775                 780

Lys Val Leu Asn Glu Ala Glu Gly Trp Leu Gly Asp Pro Thr Asn His
785                 790                 795                 800
```

```
Ala Tyr Gln Ile Leu Lys Asp Glu Ile Thr Thr Ala Trp Asp Val Glu
            805                 810                 815

Pro Leu Leu Val Arg Glu Gly Gly Ser Ile Ser Cys Leu Arg Met Leu
            820                 825                 830

Glu Arg Ile Phe Asp Ala Pro Ala Val Gln Ile Pro Cys Gly Gln Ser
            835                 840                 845

Thr Asp Asn Gly His Leu Ala Asn Glu Asn Leu Arg Ile Lys Asn Trp
        850                 855                 860

Ser Asn Leu Thr Glu Ile Leu Ser Lys Val Phe Asn Arg Leu
865                 870                 875

<210> SEQ ID NO 63
<211> LENGTH: 100
<212> TYPE: DNA
<213> ORGANISM: Artificial Sequence
<220> FEATURE:
<223> OTHER INFORMATION: primer

<400> SEQUENCE: 63
ttaagtgaaa aactatttcg agaaaccgaa caaccctgta aggaaaagtg aaaaacgagg      60
gcagaagtaa ttgtgaaatc gttcatcatc tcatggatct                          100

<210> SEQ ID NO 64
<211> LENGTH: 100
<212> TYPE: DNA
<213> ORGANISM: Artificial Sequence
<220> FEATURE:
<223> OTHER INFORMATION: primer

<400> SEQUENCE: 64
actaattatc attaggtaga ggcctacata tgcaaattgg gtatatatta agcactttaa      60
aatcaattgt ttgtagttgt agattcccgg gtaataactg                          100
```